US012755821B2

(12) United States Patent
Hori et al.

(10) Patent No.: US 12,755,821 B2
(45) Date of Patent: Oct. 6, 2026

(54) INFORMATION PROCESSING APPARATUS, INFORMATION PROCESSING METHOD, ENDOSCOPE SYSTEM, AND REPORT CREATION SUPPORT DEVICE

(71) Applicant: FUJIFILM Corporation, Tokyo (JP)

(72) Inventors: Yuma Hori, Kanagawa (JP); Yuya Kimura, Kanagawa (JP); Tatsuya Kobayashi, Kanagawa (JP); Kenichi Harada, Kanagawa (JP); Goro Miura, Kanagawa (JP); Shungo Asano, Kanagawa (JP); Hiromu Shimpo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 137 days.

(21) Appl. No.: 18/402,765

(22) Filed: Jan. 3, 2024

(65) Prior Publication Data

US 2024/0136034 A1 Apr. 25, 2024
US 2024/0233896 A9 Jul. 11, 2024

Related U.S. Application Data

(63) Continuation of application No. PCT/JP2022/025953, filed on Jun. 29, 2022.

(30) Foreign Application Priority Data

Jul. 7, 2021 (JP) ................................ 2021-113089

(51) Int. Cl.
*G06F 3/0482* (2013.01)
*G06F 40/174* (2020.01)
(Continued)

(52) U.S. Cl.
CPC ........... *G16H 15/00* (2018.01); *G06F 3/0482* (2013.01); *G06F 40/174* (2020.01); *G06V 20/60* (2022.01); *G06V 2201/034* (2022.01)

(58) Field of Classification Search
CPC .............. G06V 2201/034; G15H 15/00; G06F 3/048-05
See application file for complete search history.

(56) References Cited

U.S. PATENT DOCUMENTS

2003/0128400 A1* 7/2003 Watai .................... G16H 30/20 382/128
2012/0069394 A1* 3/2012 Ono ..................... G06F 3/1288 358/1.15
(Continued)

FOREIGN PATENT DOCUMENTS

JP 2016021216 2/2016
JP 2016062488 4/2016
(Continued)

OTHER PUBLICATIONS

English Translation of JP 2016062488 A published on Apr. 25, 2016 (Year: 2016).*
(Continued)

*Primary Examiner* — Daniel Rodriguez
(74) *Attorney, Agent, or Firm* — JCIPRNET

(57) ABSTRACT

There are provided an information processing apparatus, an information processing method, an endoscope system, and a report creation support device which can efficiently input information on a treatment name. The information processing apparatus includes a first processor. The first processor acquires an image captured using an endoscope, displays the acquired image in a first region on a screen of a first display unit, detects a treatment tool from the acquired image, chooses a plurality of treatment names corresponding to the detected treatment tool, displays the plurality of chosen treatment names in a second region on the screen of the first display unit, and accepts selection of one treatment name from among the plurality of displayed treatment names.

32 Claims, 37 Drawing Sheets

(51) Int. Cl.
*G06V 20/60* (2022.01)
*G16H 15/00* (2018.01)

(56) References Cited

U.S. PATENT DOCUMENTS

| | | | | |
|---|---|---|---|---|
| 2012/0296858 | A1* | 11/2012 | Guyan | G06Q 40/08 706/47 |
| 2020/0143538 | A1* | 5/2020 | Kamon | A61B 1/000094 |
| 2020/0143936 | A1* | 5/2020 | Kamon | G16H 15/00 |
| 2021/0177248 | A1 | 6/2021 | Usuda | |
| 2022/0139545 | A1* | 5/2022 | Liu | A61N 1/3993 705/3 |
| 2023/0285080 | A1* | 9/2023 | Hladio | A61B 5/4528 |
| 2025/0104396 | A1* | 3/2025 | Bronicki | G06Q 30/0633 |

FOREIGN PATENT DOCUMENTS

| | | | | |
|---|---|---|---|---|
| JP | 2016062488 | A * | 4/2016 | |
| JP | 2016158752 | | 9/2016 | |
| WO | 2020036224 | | 2/2020 | |
| WO | WO-2021045996 | A1 * | 3/2021 | G06F 40/169 |

OTHER PUBLICATIONS

"International Search Report (Form PCT/ISA/210) of PCT/JP2022/025953," mailed on Sep. 13, 2022, with English translation thereof, pp. 1-5.

"Written Opinion of the International Searching Authority (Form PCT/ISA/237) of PCT/JP2022/025953," mailed on Sep. 13, 2022, with English translation thereof, pp. 1-10.

"Notice of Reasons for Refusal of Japan Counterpart Application", issued on May 12, 2026, with English translation thereof, p. 1-p. 12.

* cited by examiner

FIG. 18

| TREATMENT TOOL | TREATMENT NAME TO BE DISPLAYED | DISPLAY RANK | DEFAULT OPTION |
|---|---|---|---|
| BIOPSY FORCEPS | CFP | 1 | CSP |
| | Biopsy | 2 | |
| SNARE | Polypectomy | 1 | Polypectomy |
| | EMR | 2 | |
| | Cold Polypectomy | 3 | |

FIG. 37

90

| AV DISTANCE |
| --- |
| LESS THAN 10 cm |
| 10 TO 20 cm |
| 20 TO 30 cm |
| 30 TO 40 cm |
| 40 cm OR MORE |

FIG. 38

92

| SIZE |
| --- |
| 0 TO 5 mm |
| 5 TO 10 mm |
| 10 TO 15 mm |
| 15 TO 20 mm |
| 20 mm OR MORE |

INFORMATION PROCESSING APPARATUS, INFORMATION PROCESSING METHOD, ENDOSCOPE SYSTEM, AND REPORT CREATION SUPPORT DEVICE

CROSS-REFERENCE TO RELATED APPLICATIONS

The present application is a Continuation of PCT International Application No. PCT/JP2022/025953 filed on Jun. 29, 2022 claiming priority under 35 U.S.C. § 119(a) to Japanese Patent Application No. 2021-113089 filed on Jul. 7, 2021. Each of the above applications is hereby expressly incorporated by reference, in its entirety, into the present application.

BACKGROUND OF THE INVENTION

1. Field of the Invention

The present invention relates to an information processing apparatus, an information processing method, an endoscope system, and a report creation support device, and particularly relates to an information processing apparatus, an information processing method, an endoscope system, and a report creation support device which process information on an examination (including an observation) by an endoscope.

2. Description of the Related Art

In an examination using an endoscope, a report in which findings and the like are described after the examination has ended is created. JP2016-21216A discloses a technique of inputting information necessary for generating a report in real time during the examination. In JP2016-21216A, in a case where a site of a hollow organ is designated by a user during the examination, a disease name selection screen and a characteristic selection screen are displayed in order on a display unit, and information on the disease name and information on the characteristic selected on each selection screen are recorded in a storage unit in association with information on the designated site of the hollow organ. Further, in JP2016-21216A, in a case where a treatment is performed during the examination, the treatment name is also input. The input of the treatment name is performed on the characteristic selection screen. In this case, selectable candidates for the treatment name are displayed corresponding to the previously selected disease name.

SUMMARY OF THE INVENTION

There are many treatments that can be executed by an endoscope, and it is difficult to narrow down the candidates on the basis of the disease name. As a result, in the method of JP2016-21216A, in order to select the treatment name, it is necessary to display many candidates, and thus, there is a disadvantage in that the user cannot efficiently select the treatment name.

The present invention is made in view of such circumstances, and an object thereof is to provide an information processing apparatus, an information processing method, an endoscope system, and a report creation support device which can efficiently input information on a treatment name.

(1) An information processing apparatus including a first processor, in which the first processor is configured to acquire an image captured using an endoscope, display the acquired image in a first region on a screen of a first display unit, detect a treatment tool from the acquired image, choose a plurality of treatment names corresponding to the detected treatment tool, display the plurality of chosen treatment names in a second region on the screen of the first display unit, and accept selection of one treatment name from among the plurality of displayed treatment names.

(2) The information processing apparatus described in (1), in which the first processor displays the plurality of treatment names in the second region in a state where one treatment name is selected in advance.

(3) The information processing apparatus described in (2), in which the first processor chooses the plurality of treatment names by referring to a table in which the plurality of treatment names are associated for each treatment tool.

(4) The information processing apparatus described in (3), in which, in the table, information on the treatment name to be selected by default is further associated for each treatment tool, and the first processor displays the plurality of treatment names in the second region in a state where one treatment name is selected in advance by referring to the table.

(5) The information processing apparatus described in (3) or (4), in which, in the table, information on a display order of the plurality of treatment names is further associated for each treatment tool, and the first processor displays the plurality of treatment names in the display order corresponding to the detected treatment tool in the second region by referring to the table.

(6) The information processing apparatus described in (5), in which the first processor is configured to record a history of selection of the treatment name, and correct the information on the display order of the treatment names registered in the table in a descending order of selection frequency on the basis of the history of the selection of the treatment name.

(7) The information processing apparatus described in (5), in which the first processor corrects the information on the display order of the treatment names registered in the table in an order of newest selection.

(8) The information processing apparatus described in any one of (3) to (7), in which, in a case where the number of the treatment names of treatments executable by the treatment tool exceeds a specified number, the treatment names corresponding to the specified number or less are registered in the table.

(9) The information processing apparatus described in (8), in which the specified number is set to a number smaller than the number of the treatment names selectable in an input field for the treatment name in a report creation support device that supports creation of a report in which at least the treatment name is to be entered.

(10) The information processing apparatus described in any one of (1) to (9), in which the first processor is configured to detect a plurality of types of treatment tools, choose, in a case where a specific treatment tool among the plurality of types of the treatment tools is detected, a plurality of treatment names corresponding to the detected specific treatment tool, display the plurality of chosen treatment names in the second region, and accept selection of one treatment name from among the plurality of displayed treatment names.

(11) The information processing apparatus described in any one of (1) to (10), in which the first processor displays items of no treatment and/or post-selection as selectable items in addition to the plurality of chosen treatment names, in the second region.

(12) The information processing apparatus described in any one of (1) to (11), in which the first processor displays the plurality of treatment names in the second region after a first time has elapsed from disappearance of the treatment tool from the image.

(13) The information processing apparatus described in any one of (1) to (12), in which the first processor is configured to accept selection until a second time elapses from start of display of the plurality of treatment names in the second region, and confirm the selection after the second time has elapsed.

(14) The information processing apparatus described in (13), in which, in a case where the selection is accepted until the second time elapses, the first processor extends a period for acceptance until the second time elapses from the acceptance of the selection.

(15) The information processing apparatus described in (13) or (14), in which, in a case where the acceptance of the selection is started, the first processor displays display indicating a remaining time until end of the acceptance, in a third region on the screen of the first display unit.

(16) The information processing apparatus described in (15), in which the first processor displays information on the treatment name of which the selection is confirmed, in the third region.

(17) The information processing apparatus described in any one of (1) to (16), in which, in a case where the treatment tool is detected from the image, the first processor displays a figure or a symbol indicating detection of the treatment tool, in a fourth region on the screen of the first display unit.

(18) The information processing apparatus described in (17), in which the first processor displays the figure or the symbol corresponding to the detected treatment tool in the fourth region.

(19) The information processing apparatus described in any one of (1) to (18), in which the second region is set in a vicinity of a position where a treatment tool appears within the image displayed in the first region.

(20) The information processing apparatus described in any one of (1) to (19), in which the first processor is configured to acquire information on a site, and record information on the selected treatment name in association with the acquired information on the site.

(21) The information processing apparatus described in any one of (1) to (20), in which the first processor displays a list box in which the plurality of treatment names are displayed in a list, in the second region.

(22) The information processing apparatus described in any one of (1) to (21), in which the first processor records a static image captured during a treatment, in association with information on the selected treatment name.

(23) The information processing apparatus described in (22), in which the first processor records, as a candidate for an image to be used in a report or a diagnosis, the static image captured during the treatment, in association with the information on the selected treatment name.

(24) The information processing apparatus described in (23), in which the first processor acquires, as the candidate for the image to be used in the report or the diagnosis, a most recent static image in terms of time among static images captured before a time point when selection of the treatment name is accepted, or an oldest static image in terms of time among static images captured after the time point when the selection of the treatment name is accepted.

(25) The information processing apparatus described in any one of (1) to (24), in which the first processor is configured to display the plurality of treatment names in the second region, display a plurality of options regarding a treatment target in a fifth region on the screen of the first display unit before selection of the treatment name is accepted or after the selection of the treatment name is accepted, and accept one selection from among the plurality of options displayed in the fifth region.

(26) The information processing apparatus described in (25), in which the plurality of options regarding the treatment target are a plurality of options for a detailed site or a size of the treatment target.

(27) A report creation support device that supports creation of a report, including a second processor, in which the second processor is configured to display a report creation screen with at least an input field for a treatment name, on a second display unit, acquire information on the treatment name selected in the information processing apparatus described in any one of (1) to (26), automatically input the acquired information on the treatment name to the input field for the treatment name, and accept correction of the automatically input information of the input field for the treatment name.

(28) The report creation support device described in (27), in which, in a case where an instruction to correct the information on the treatment name is given, the second processor is configured to display the plurality of treatment names on the second display unit, and accept the correction of the information on the treatment name via selection.

(29) The report creation support device described in (28), in which the number of the selectable treatment names is greater than the number of the treatment names selectable in the information processing apparatus.

(30) The report creation support device described in any one of (27) to (29), in which the second processor displays the input field for the treatment name such that the input field for the treatment name is distinguishable from other input fields on the report creation screen.

(31) A report creation support device that supports creation of a report, including a second processor, in which the second processor is configured to display a report creation screen with at least input fields for a treatment name and a static image, on a second display unit, acquire information on the treatment name and the static image selected in the information processing apparatus according to any one of claims 22 to 24, automatically input the acquired information on the treatment name to the input field for the treatment name, automatically input the acquired static image to the input field for the static image, and accept correction of the automatically input information of the input field for the treatment name and the automatically input static image of the input field for the static image.

(32) An endoscope system including an endoscope; the information processing apparatus described in any one of (1) to (26); and an input device.

(33) An information processing method including a step of acquiring an image captured using an endoscope; a step of displaying the acquired image in a first region on a screen of a first display unit; a step of detecting a treatment tool from the acquired image; a step of choosing a plurality of treatment names corresponding to the detected treatment tool; a step of displaying the plurality of chosen treatment names in a second region on the screen of the first display unit; and a step of accepting selection of one treatment name from among the plurality of displayed treatment names.

According to the present invention, it is possible to efficiently input information on a treatment name.

BRIEF DESCRIPTION OF THE DRAWINGS

FIG. 18 is a diagram illustrating an example of a table.

FIG. 37 is a diagram illustrating an example of a detailed site selection box.

FIG. 38 is a diagram illustrating an example of a size selection box.

DESCRIPTION OF THE PREFERRED EMBODIMENTS

Hereinafter, preferred embodiments of the present invention will be described in detail with reference to the accompanying drawings.

First Embodiment

[Endoscopic Image Diagnosis Support System]

Here, a case where the present invention is applied to an endoscopic image diagnosis support system will be described as an example. The endoscopic image diagnosis support system is a system that supports detection and discrimination of a lesion or the like in an endoscopy. In the following, an example of application to an endoscopic image diagnosis support system that supports detection and discrimination of a lesion and the like in a lower digestive tract endoscopy (large intestine examination) will be described.

Figure 1:
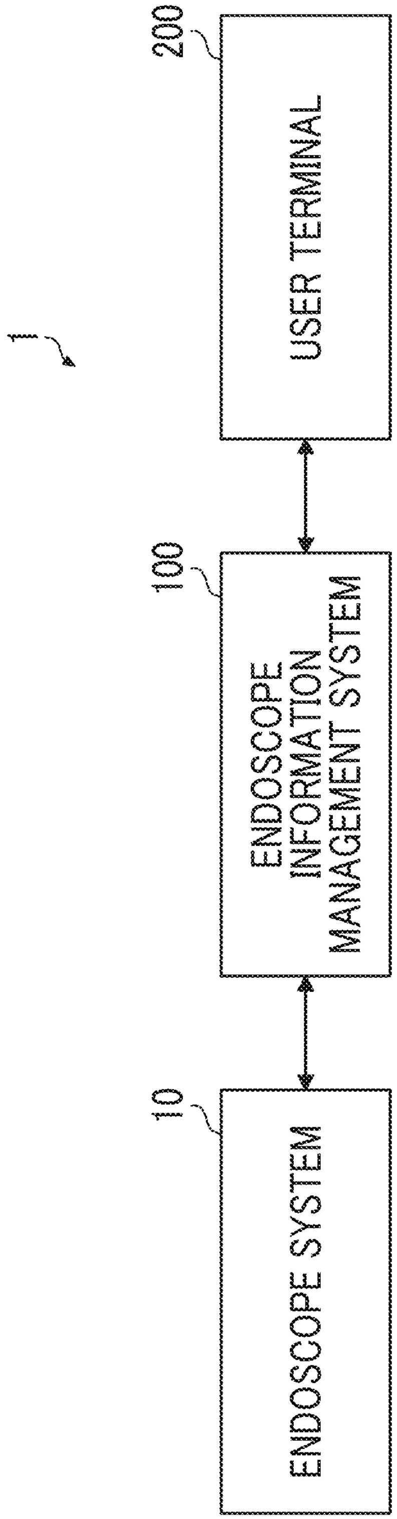
FIG. 1 is a block diagram illustrating an example of a system configuration of an endoscopic image diagnosis support system.

FIG. 1 is a block diagram illustrating an example of a system configuration of the endoscopic image diagnosis support system.

As illustrated in the figure, an endoscopic image diagnosis support system 1 of the present embodiment has an endoscope system 10, an endoscope information management system 100, and a user terminal 200.

[Endoscope System]

Figure 2:
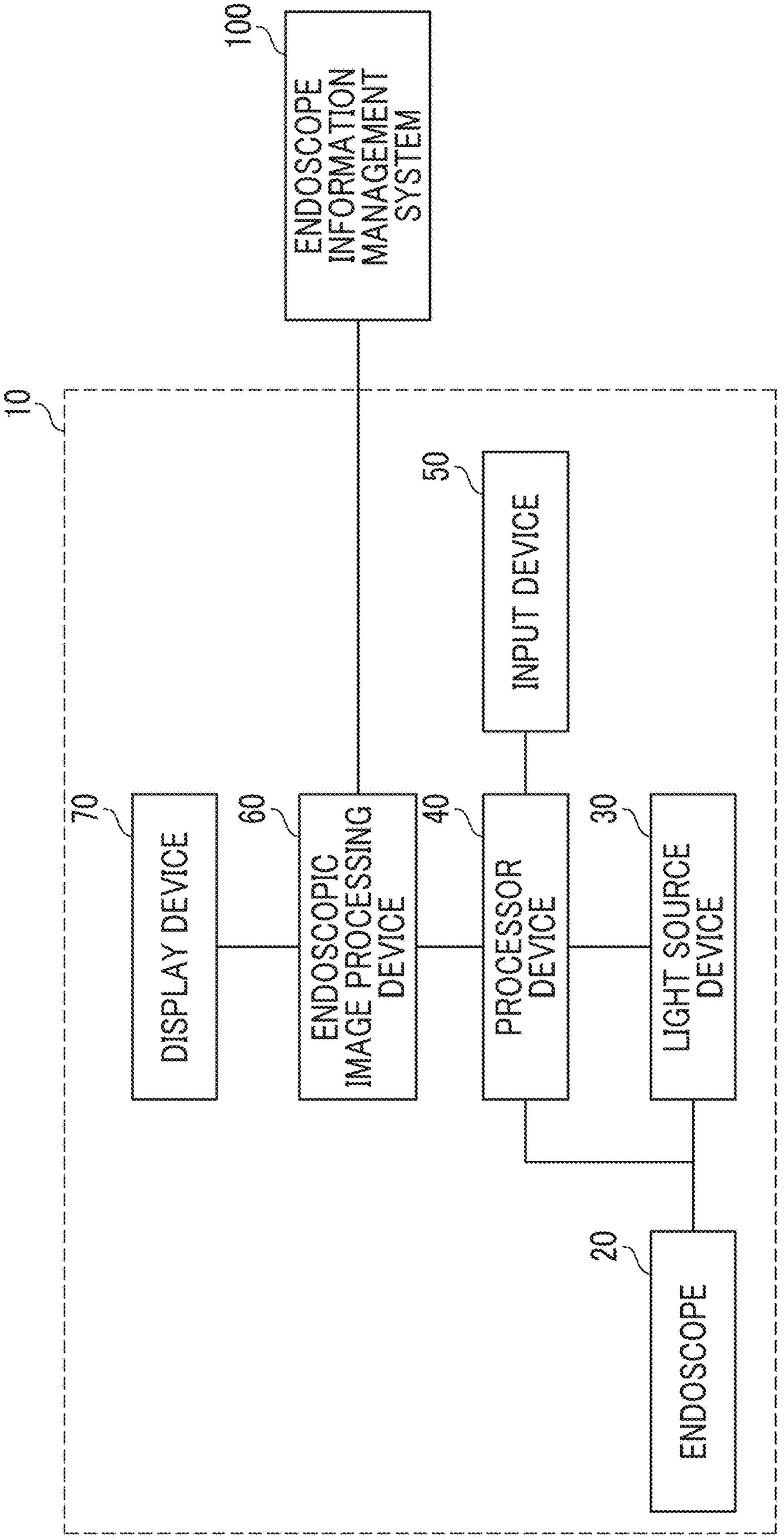
FIG. 2 is a block diagram illustrating an example of a system configuration of an endoscope system.

FIG. 2 is a block diagram illustrating an example of a system configuration of the endoscope system.

The endoscope system 10 of the present embodiment is configured as a system capable of an observation using special light (special light observation) in addition to an observation using white light (white light observation). In the special light observation, a narrow-band light observation is included. In the narrow-band light observation, a blue laser imaging observation (BLI observation), a narrow band imaging observation (NBI observation), a linked color imaging observation (LCI observation), and the like are included. Note that the special light observation itself is a well-known technique, so detailed description thereof will be omitted.

As illustrated in FIG. 2, the endoscope system 10 of the present embodiment has an endoscope 20, a light source device 30, a processor device 40, an input device 50, an endoscopic image processing device 60, a display device 70, and the like.

[Endoscope]

Figure 3:
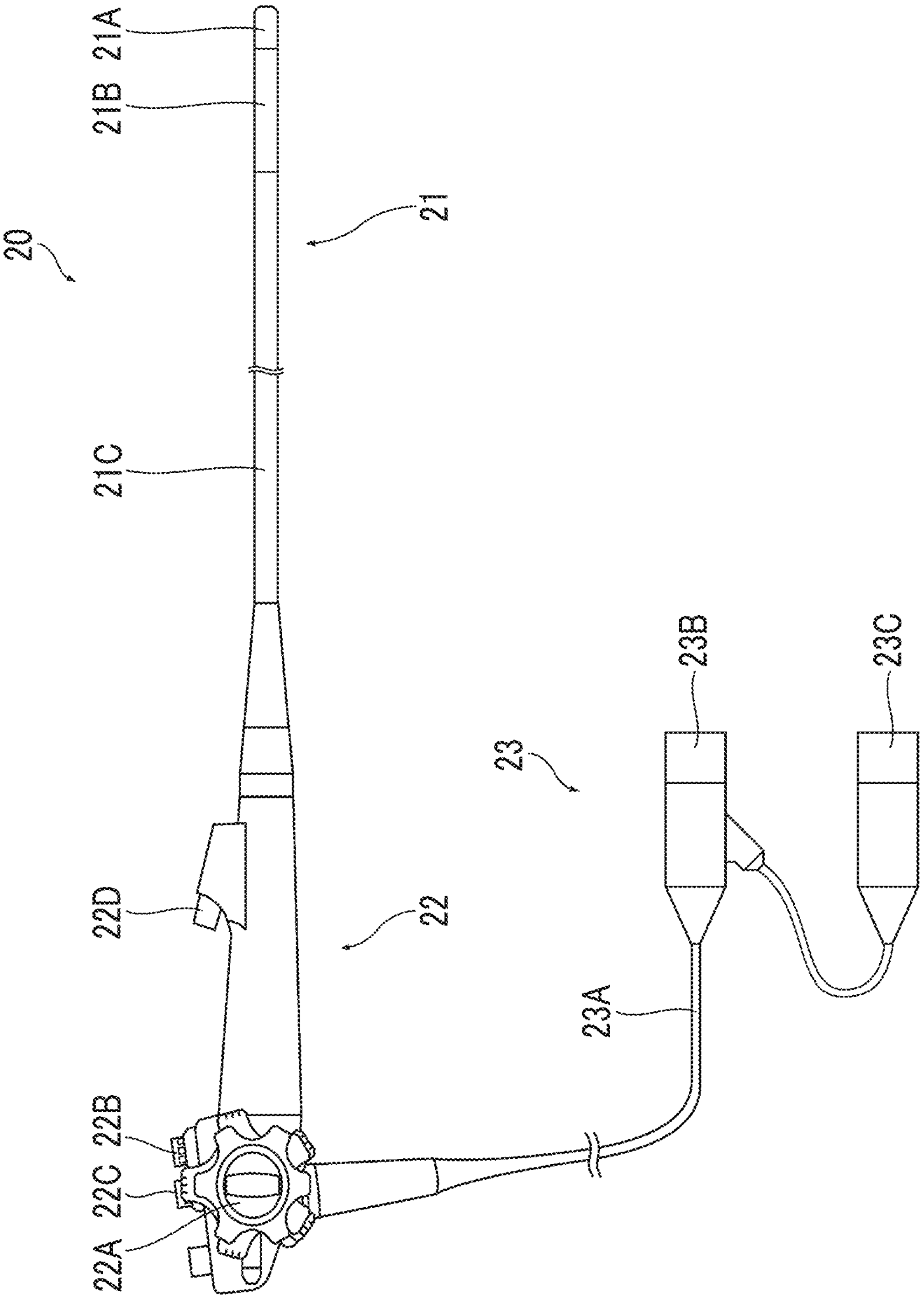
FIG. 3 is a block diagram illustrating a schematic configuration of an endoscope.

FIG. 3 is a diagram illustrating a schematic configuration of the endoscope.

The endoscope 20 of the present embodiment is an endoscope for a lower digestive organ. As illustrated in FIG. 3, the endoscope 20 is a flexible endoscope (electronic endoscope), and has an insertion part 21, an operation part 22, and a connection part 23.

The insertion part 21 is a part to be inserted into a hollow organ (large intestine in the present embodiment). The insertion part 21 includes a distal end portion 21A, a bendable portion 21B, and a soft portion 21C in order from a distal end.

Figure 4:
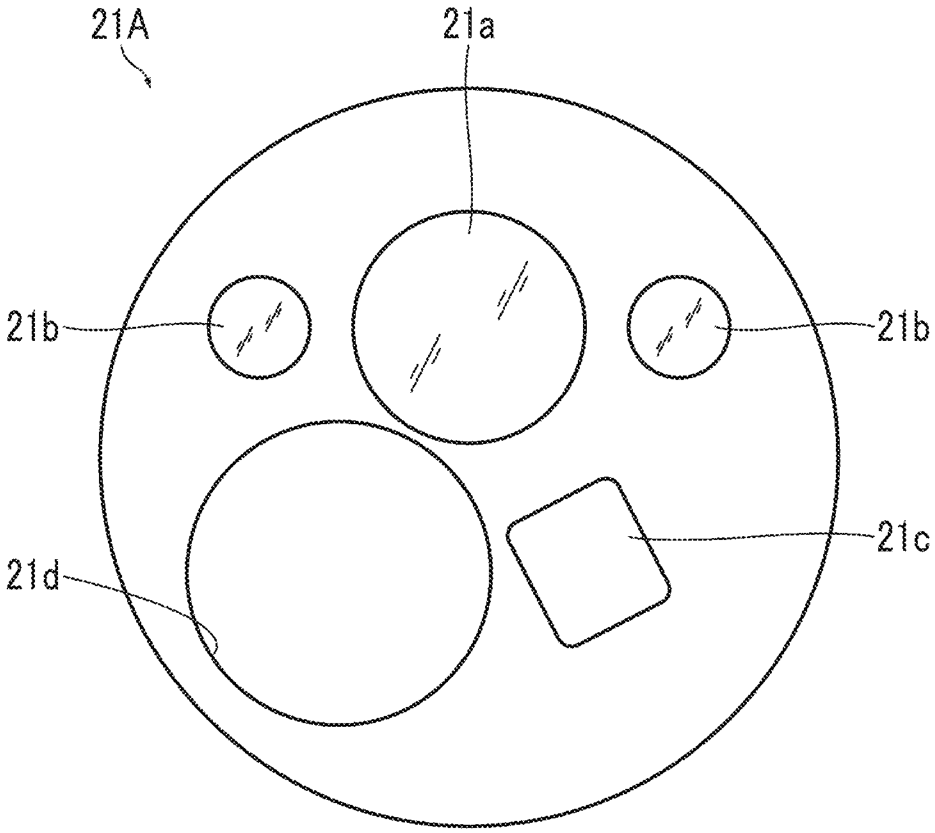
FIG. 4 is a diagram illustrating an example of a configuration of an end face of a distal end portion.

FIG. 4 is a diagram illustrating an example of a configuration of an end face of the distal end portion.

As illustrated in the figure, in the end face of the distal end portion 21A, an observation window 21*a*, illumination windows 21*b*, an air/water supply nozzle 21*c*, a forceps outlet 21*d*, and the like are provided. The observation window 21*a* is a window for an observation. The inside of the hollow organ is imaged through the observation window 21*a*. Imaging is performed via an optical system and an image sensor (not illustrated) built in the distal end portion 21A. As the image sensor, for example, a complementary metal-oxide-semiconductor image sensor (CMOS image sensor), a charge-coupled device image sensor (CCD image sensor), or the like is used. The illumination windows 21*b* are windows for illumination. The inside of the hollow organ is irradiated with illumination light via the illumination windows 21*b*. The air/water supply nozzle 21*c* is a nozzle for cleaning. A cleaning liquid and a drying gas are sprayed from the air/water supply nozzle 21*c* toward the observation window 21*a*. The forceps outlet 21*d* is an outlet for a treatment tool such as forceps. The forceps outlet 21*d* functions as a suction port for sucking body fluids and the like.

Figure 5:
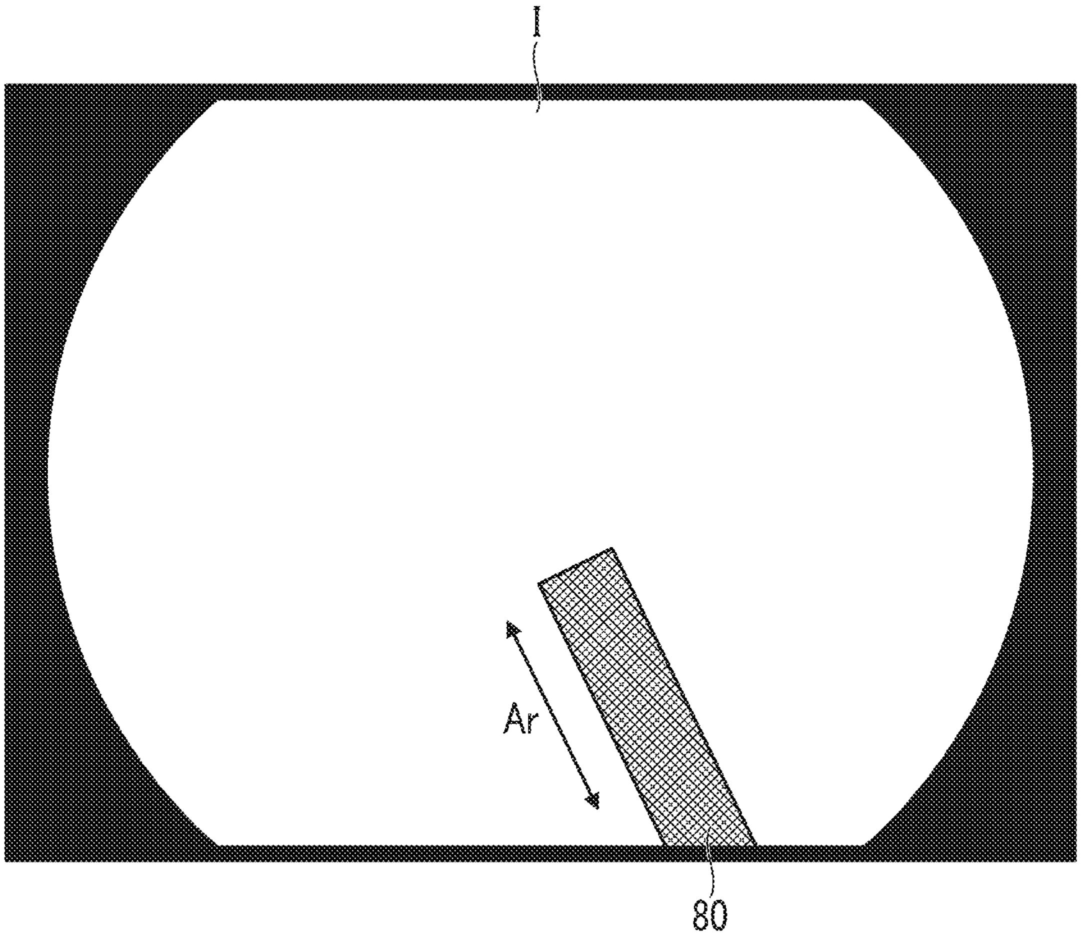
FIG. 5 is a diagram illustrating an example of an endoscopic image in a case where a treatment tool is used.

FIG. 5 is a diagram illustrating an example of an endoscopic image in a case where a treatment tool is used.

A position of the forceps outlet 21*d* is fixed with respect to a position of the observation window 21*a*. Therefore, in a case where a treatment tool is used, the treatment tool always appears from a certain position in the image, and is taken in and out along a certain direction. FIG. 5 illustrates an example of a case in which a treatment tool 80 appears from a lower right position in an endoscopic image I, and is moved along a direction (forceps direction) indicated by an arrow Ar.

The bendable portion 21B is a portion that is bent according to an operation of an angle knob 22A of the operation part 22. The bendable portion 21B is bent in four directions of up, down, left, and right.

The soft portion 21C is an elongated portion provided between the bendable portion 21B and the operation part 22. The soft portion 21C has flexibility.

The operation part 22 is a part that is held by an operator to perform various operations. The operation part 22 includes various operation members. As an example, the operation part 22 includes the angle knob 22A for a bending operation of the bendable portion 21B, an air/water supply button 22B for performing an air/water supply operation, and a suction button 22C for performing a suction operation. In addition, the operation part 22 includes an operation member (shutter button) for imaging a static image, an operation member for switching an observation mode, an operation member for switching on and off of various support functions, and the like. Further, the operation part 22 includes a forceps insertion port 22D for inserting a treatment tool such as forceps. The treatment tool inserted from the forceps insertion port 22D is drawn out from the forceps outlet 21*d* (refer to FIG. 4) on the distal end of the insertion part 21. As an example, the treatment tool includes biopsy forceps, snares, and the like.

The connection part 23 is a part for connecting the endoscope 20 to the light source device 30, the processor device 40, and the like. The connection part 23 includes a cord 23A extending from the operation part 22, and a light guide connector 23B and a video connector 23C that are provided on the distal end of the cord 23A. The light guide connector 23B is a connector for connecting the endoscope 20 to the light source device 30. The video connector 23C is a connector for connecting the endoscope 20 to the processor device 40.

[Light Source Device]

The light source device 30 generates illumination light. As described above, the endoscope system 10 of the present embodiment is configured as a system capable of the special light observation in addition to the normal white light observation. Therefore, the light source device 30 is configured to be capable of generating light (for example, narrow-band light) corresponding to the special light observation in addition to the normal white light. Note that, as described above, the special light observation itself is a well-known technique, so the description for the light generation will be omitted.

[Processor Device]

The processor device 40 integrally controls the operation of the entire endoscope system. The processor device 40 includes, as a hardware configuration, a processor, a main storage unit, an auxiliary storage unit, a communication unit, and the like. That is, the processor device 40 has a so-called computer configuration as the hardware configuration. For example, the processor is configured by a central processing unit (CPU) and the like. For example, the main storage unit is configured by a random-access memory (RAM) and the like. For example, the auxiliary storage unit is configured by a flash memory and the like.

Figure 6:
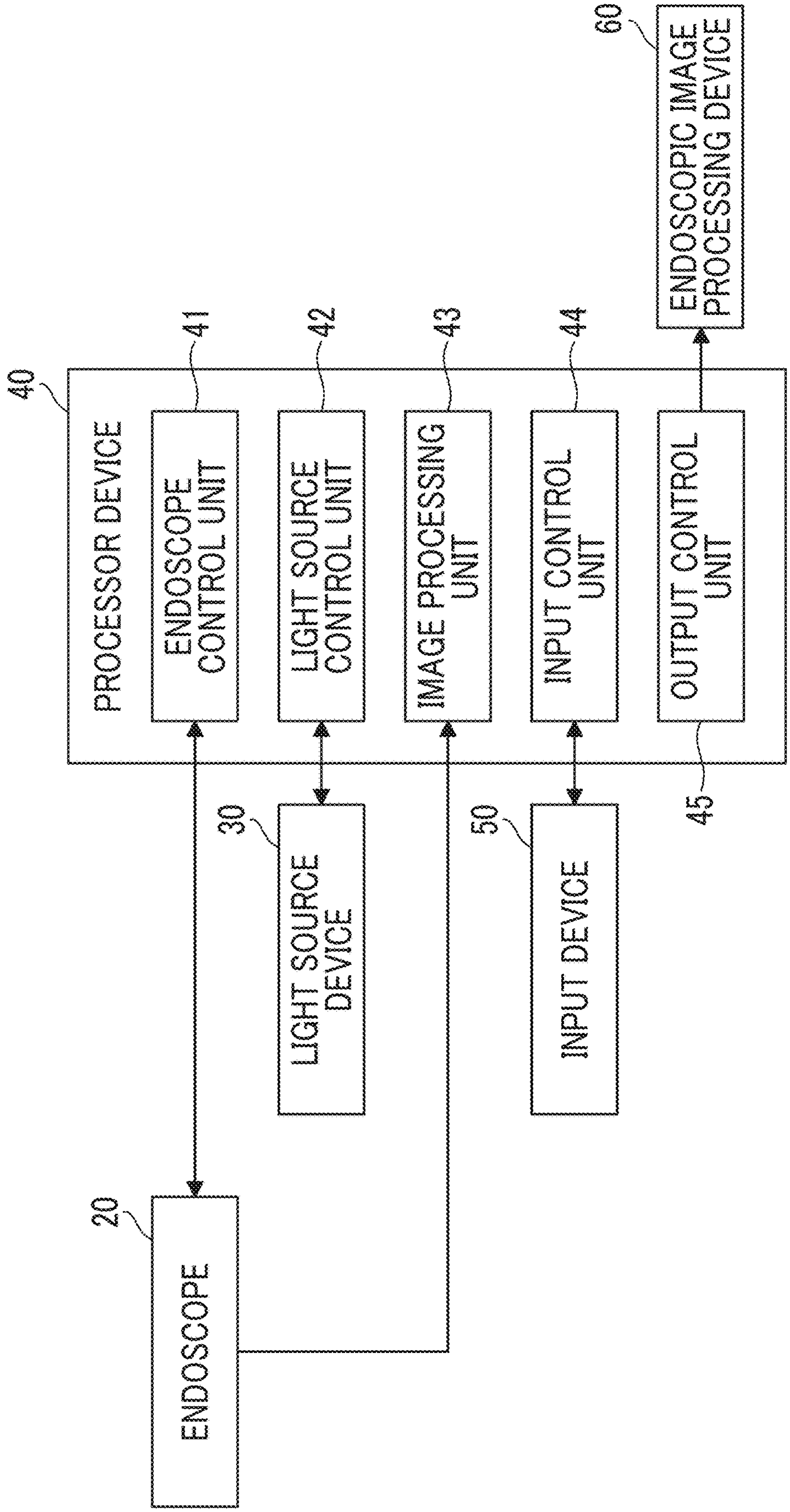
FIG. 6 is a block diagram of main functions of a processor device.

FIG. 6 is a block diagram of main functions of the processor device.

As illustrated in the figure, the processor device 40 has functions of an endoscope control unit 41, a light source control unit 42, an image processing unit 43, an input control unit 44, an output control unit 45, and the like. Each function is realized by the processor executing a predetermined program. The auxiliary storage unit stores various programs executed by the processor, various kinds of data necessary for control, and the like.

The endoscope control unit 41 controls the endoscope 20. The control for the endoscope 20 includes image sensor drive control, air/water supply control, suction control, and the like.

The light source control unit 42 controls the light source device 30. The control for the light source device 30 includes light emission control for a light source, and the like.

The image processing unit 43 performs various kinds of signal processing on signals output from the image sensor of the endoscope 20 to generate a captured image (endoscopic image).

The input control unit 44 accepts an input of an operation and an input of various kinds of information via the input device 50.

The output control unit 45 controls an output of information to the endoscopic image processing device 60. The information to be output to the endoscopic image processing device 60 includes various kinds of operation information input from the input device 50, and the like in addition to the endoscopic image obtained by imaging.

[Input Device]

The input device 50 constitutes a user interface in the endoscope system 10 together with the display device 70. For example, the input device 50 is configured by a keyboard, a mouse, a foot switch, and the like. The foot switch is an operation device that is placed at the feet of the operator and that is operated with the foot. The foot switch outputs a predetermined operation signal in a case of stepping on a pedal. In addition, the input device 50 can include a known input device such as a touch panel, an audio input device, and a gaze input device.

[Endoscopic Image Processing Device]

The endoscopic image processing device 60 performs processing of outputting the endoscopic image to the display device 70. Further, the endoscopic image processing device 60 performs various kinds of recognition processing on the endoscopic image as necessary, and performs processing of outputting the result to the display device 70. The recognition processing includes processing of detecting a lesion part or the like, discrimination processing for the detected lesion part or the like, processing of detecting a specific region in a hollow organ, processing of detecting a treatment tool, and the like. Moreover, the endoscopic image processing device 60 performs processing of supporting an input of information necessary for creating a report during the examination. Further, the endoscopic image processing device 60 performs processing of communicating with the endoscope information management system 100, and outputting examination information or the like to the endoscope information management system 100. The endoscopic image processing device 60 is an example of an information processing apparatus.

The endoscopic image processing device 60 includes, as a hardware configuration, a processor, a main storage unit, an auxiliary storage unit, a communication unit, and the like. That is, the endoscopic image processing device 60 has a so-called computer configuration as the hardware configuration. For example, the processor is configured by a CPU and the like. The processor of the endoscopic image processing device 60 is an example of a first processor. For example, the main storage unit is configured by a RAM and the like. For example, the auxiliary storage unit is configured by a flash memory and the like. For example, the communication unit is configured by a communication interface connectable to a network. The endoscopic image processing device 60 is communicably connected to the endoscope information management system 100 via the communication unit.

Figure 7:
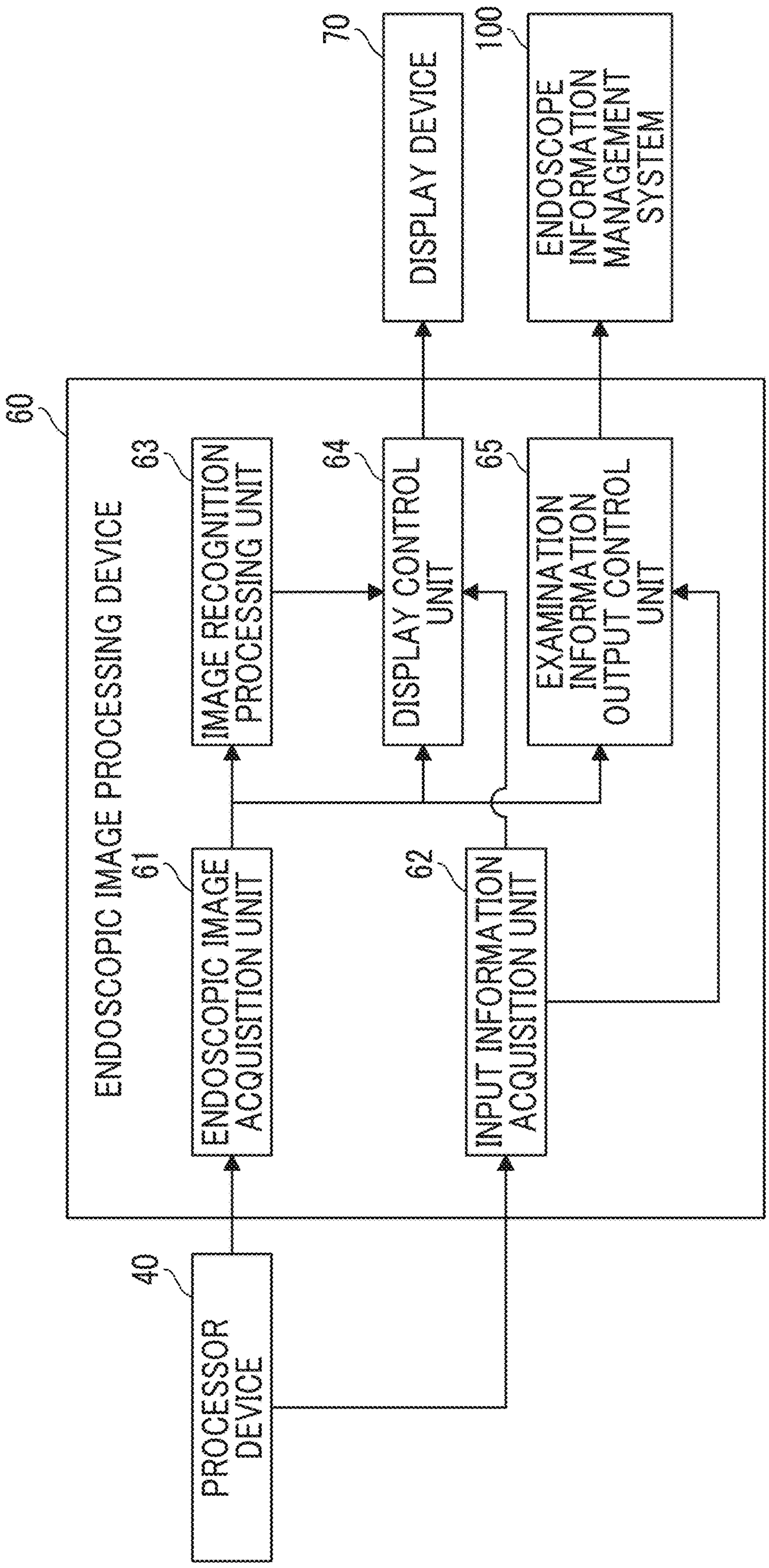
FIG. 7 is a block diagram of main functions of an endoscopic image processing device.

FIG. 7 is a block diagram of main functions of the endoscopic image processing device.

As illustrated in the figure, the endoscopic image processing device 60 mainly has functions of an endoscopic image acquisition unit 61, an input information acquisition unit 62, an image recognition processing unit 63, a display control unit 64, an examination information output control unit 65, and the like. Each function is realized by the processor executing a predetermined program. The auxiliary storage unit stores various programs executed by the processor, various kinds of data necessary for control, and the like.

[Endoscopic Image Acquisition Unit]

The endoscopic image acquisition unit 61 acquires an endoscopic image from the processor device 40. Acquisition of an image is performed in real time. That is, the image captured by the endoscope 20 is acquired in real time.

[Input Information Acquisition Unit]

The input information acquisition unit 62 acquires information input via the input device 50 or the endoscope 20. The information input via the input device 50 includes information input via a keyboard, a mouse, a foot switch, or the like. Further, the information input via the endoscope 20 includes information such as an imaging instruction for a static image. As described below, in the present embodiment, a selection operation of a site and a selection operation of a treatment name are performed via the foot switch. The input information acquisition unit 62 acquires operation information of the foot switch via the processor device 40.

[Image Recognition Processing Unit]

The image recognition processing unit 63 performs various kinds of recognition processing on the endoscopic image acquired by the endoscopic image acquisition unit 61. The recognition processing is performed in real time. That is, the recognition processing is performed in real time on the captured image.

Figure 8:
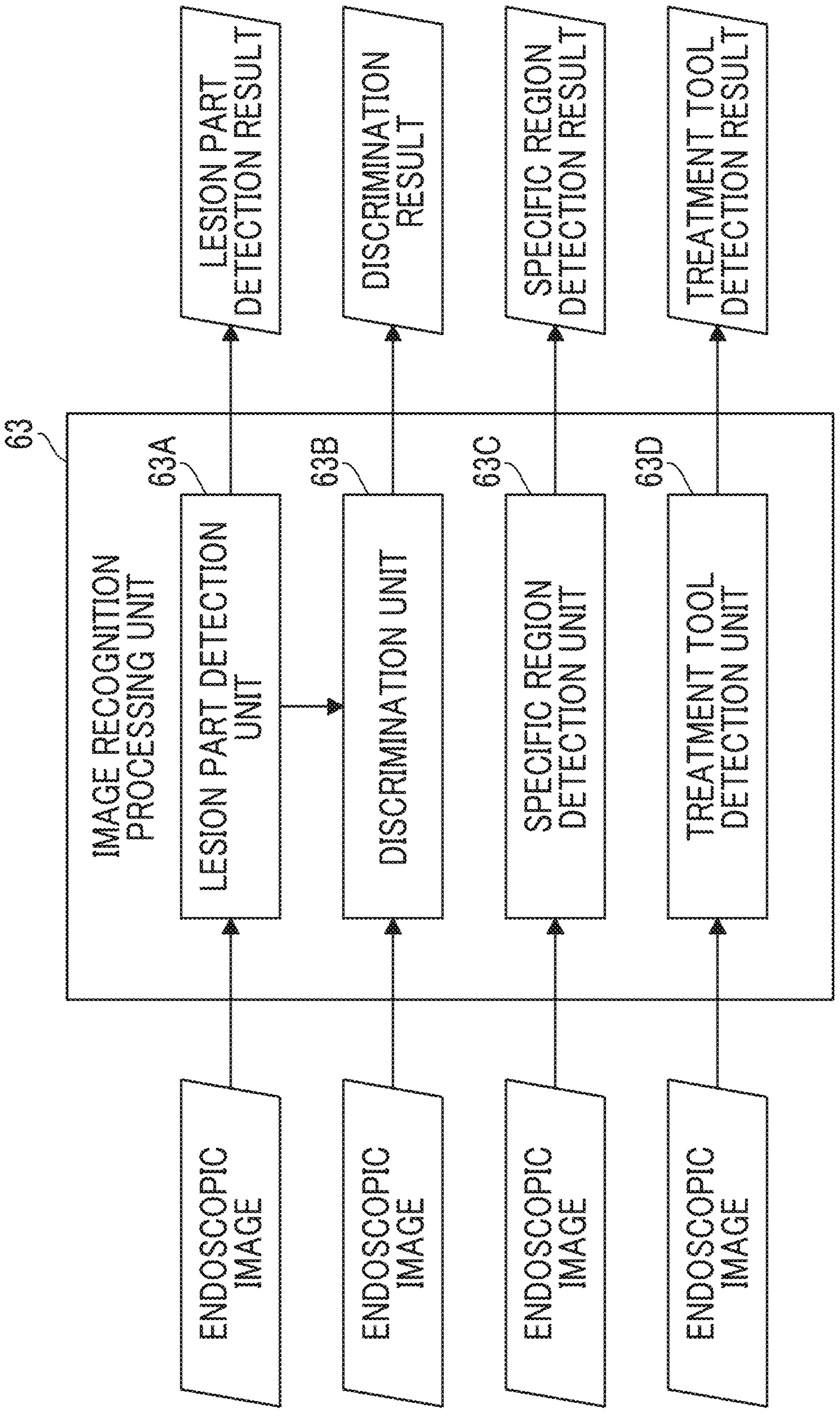
FIG. 8 is a block diagram of main functions of an image recognition processing unit.

FIG. 8 is a block diagram of main functions of the image recognition processing unit.

As illustrated in the figure, the image recognition processing unit 63 has functions of a lesion part detection unit 63A, a discrimination unit 63B, a specific region detection unit 63C, a treatment tool detection unit 63D, and the like.

The lesion part detection unit 63A detects a lesion part such as a polyp from the endoscopic image. The processing of detecting the lesion part includes processing of detecting a part with a possibility of a lesion (benign tumor, dysplasia, or the like), processing of recognizing a part with features that may be directly or indirectly associated with a lesion (erythema or the like), and the like in addition to processing of detecting a part that is definitely a lesion part.

The discrimination unit 63B performs the discrimination processing on the lesion part detected by the lesion part detection unit 63A. As an example, in the present embodiment, neoplastic or non-neoplastic (hyperplastic) discrimination processing is performed on the lesion part such as a polyp detected by the lesion part detection unit 63A.

The specific region detection unit 63C performs processing of detecting a specific region in the hollow organ from the endoscopic image. For example, processing of detecting an ileocecum of the large intestine or the like is performed. The large intestine is an example of the hollow organ. The ileocecum is an example of the specific region. The specific region detection unit 63C may detect, as the specific region, a hepatic flexure (right colon), a splenic flexure (left colon), a rectosigmoid, and the like in addition to the ileocecum. Further, the specific region detection unit 63C may detect a plurality of specific regions.

The treatment tool detection unit 63D performs processing of detecting a treatment tool appearing in the image from the endoscopic image, and discriminating the type of the treatment tool. The treatment tool detection unit 63D can be configured to detect a plurality types of treatment tools such as biopsy forceps, snares, and hemostatic clips.

Each unit (the lesion part detection unit 63A, the discrimination unit 63B, the specific region detection unit 63C, the treatment tool detection unit 63D, and the like) constituting the image recognition processing unit 63 is configured by, for example, artificial intelligence (AI) having a learning function. Specifically, each unit is configured by AI or a trained model trained using deep learning or a machine learning algorithm such as a neural network (NN), a convolutional neural network (CNN), AdaBoost, and random forest.

Note that a part or all of the units constituting the image recognition processing unit 63 can be configured to calculate a feature amount from the image and to perform detection or the like using the calculated feature amount, instead of being configured by AI or the trained model.

[Display Control Unit]

The display control unit 64 controls display of the display device 70. In the following, main display control performed by the display control unit 64 will be described.

Figure 9:
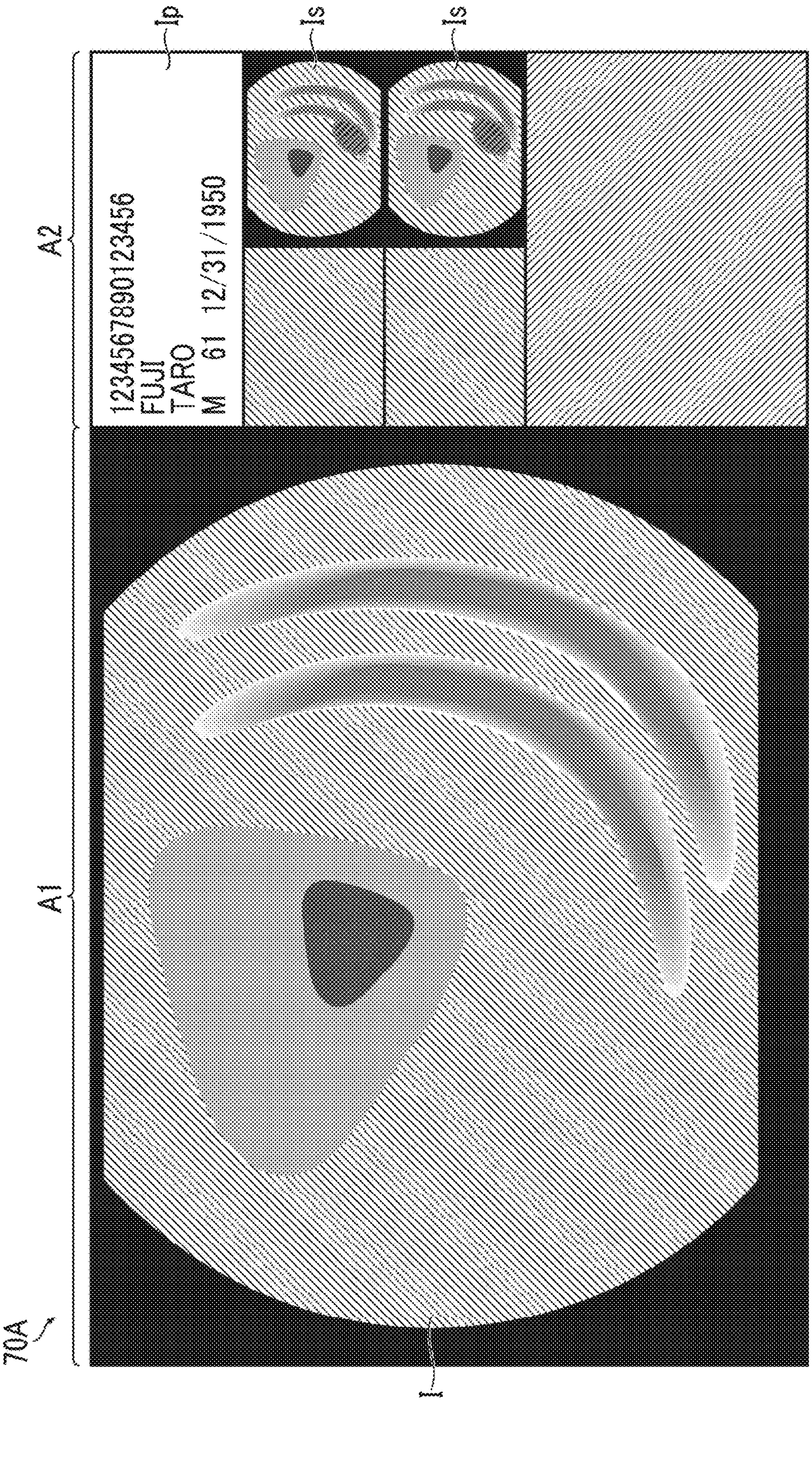
FIG. 9 is a diagram illustrating an example of display of a screen during an examination.

The display control unit 64 displays the image (endoscopic image) captured by the endoscope 20 on the display device 70 in real time during the examination. FIG. 9 is a diagram illustrating an example of display of a screen during the examination. As illustrated in the figure, the endoscopic image I (live view) is displayed in a main display region A1 set on a screen 70A. The main display region A1 is an example of a first region. A secondary display region A2 is further set on the screen 70A, and various kinds of information regarding the examination are displayed. In the example illustrated in FIG. 9, a case where information Ip regarding a patient and a static image Is of the endoscopic image captured during the examination are displayed in the secondary display region A2 is illustrated. For example, the static images Is are displayed in the captured order from top to bottom of the screen 70A.

Figure 10:
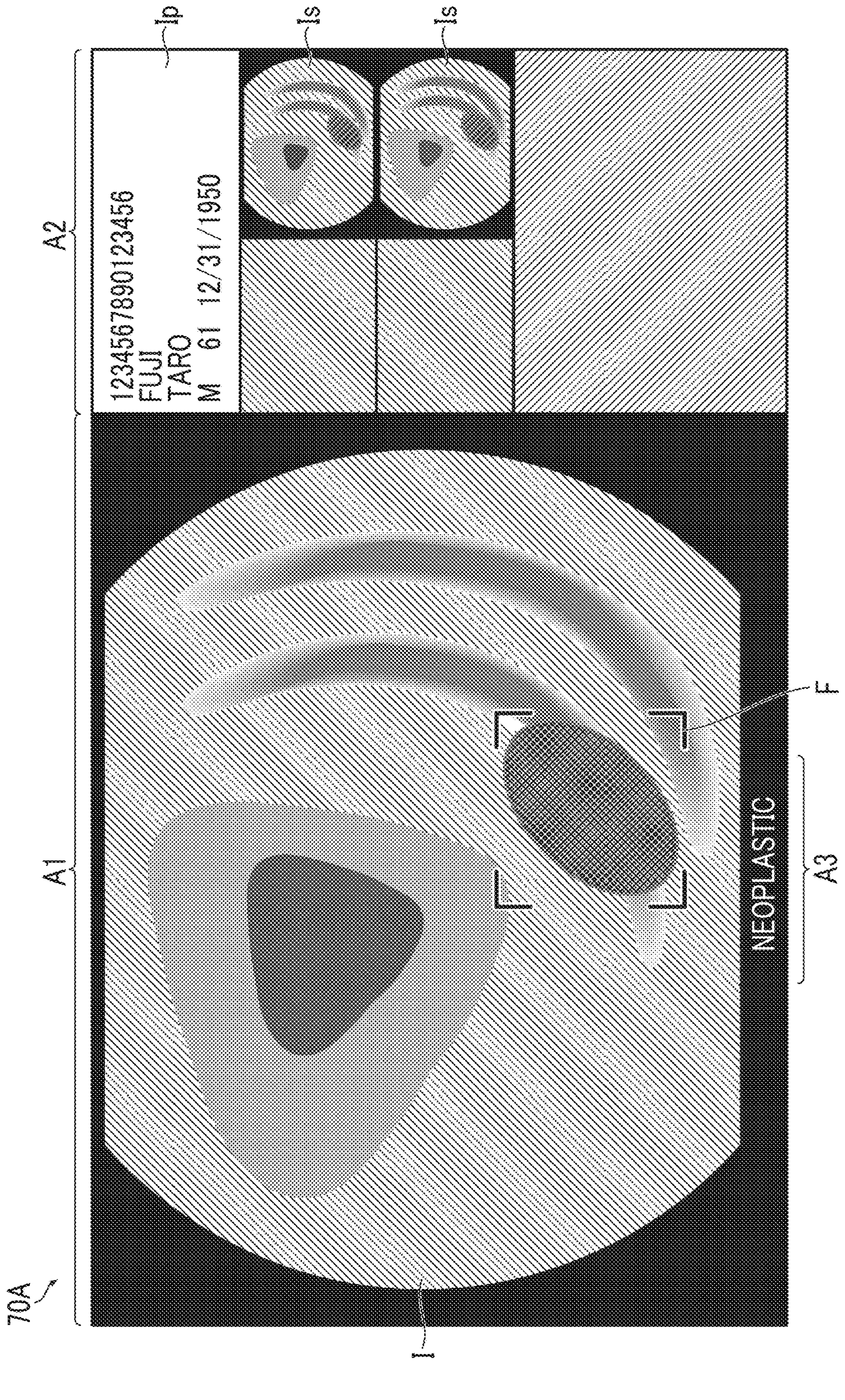
FIG. 10 is a diagram illustrating another example of display of a screen during an examination.

FIG. 10 is a diagram illustrating another example of display of the screen during the examination. The figure illustrates an example of display of a screen in a case where a detection support function for a lesion part is ON.

As illustrated in the figure, in a case where the detection support function for a lesion part is ON, in a case where a lesion part P is detected from the endoscopic image I being displayed, the display control unit 64 displays the endoscopic image I on the screen 70A by enclosing a target region (region of the lesion part P) with a frame F. Moreover, in a case where a discrimination support function is ON, the display control unit 64 displays a discrimination result in a discrimination result display region A3 set on the screen 70A in advance. In the example illustrated in FIG. 10, a case where the discrimination result is "NEOPLASTIC" is illustrated.

Figure 11:
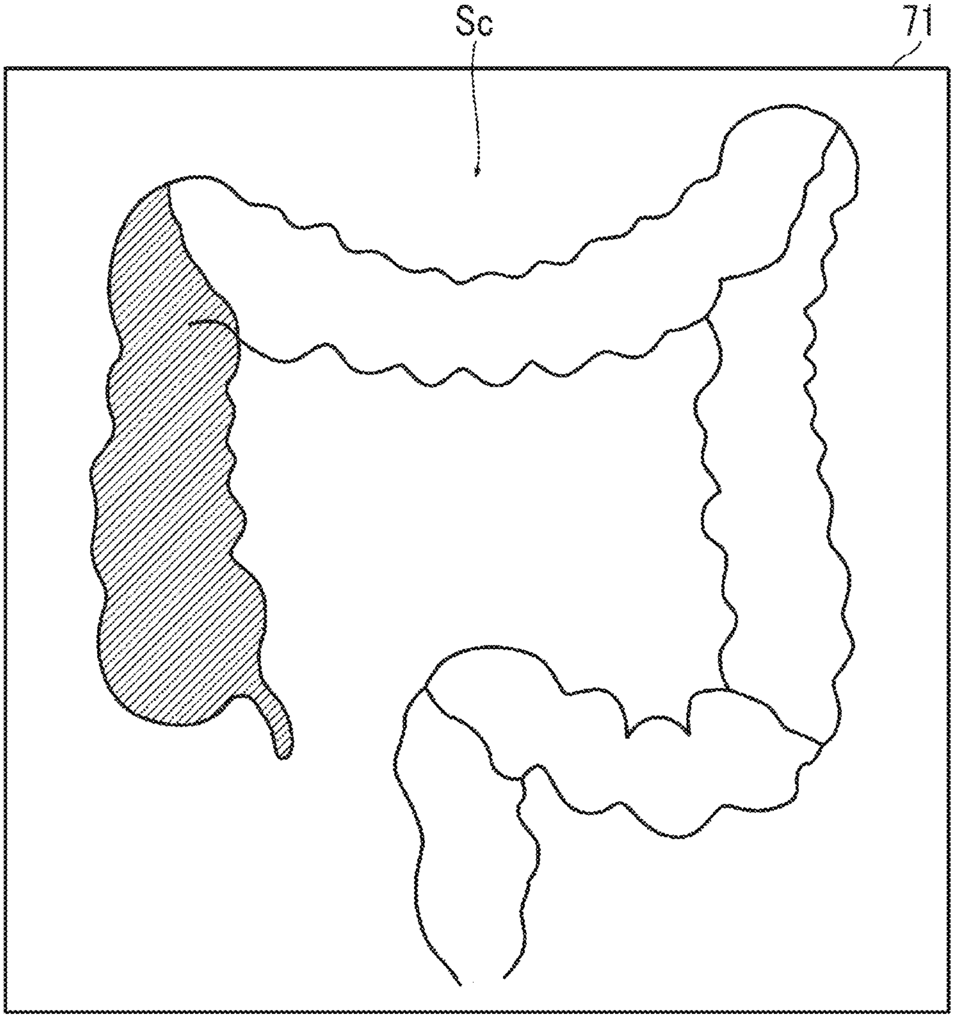
FIG. 11 is a diagram illustrating an example of a site selection box.

Further, in a case where a specific condition is satisfied, the display control unit 64 displays a site selection box 71 on the screen 70A. The site selection box 71 is a region for selecting a site of the hollow organ under examination, on the screen. The operator can select the site being imaged via the observation window 21*a* of the distal end portion 21A of the endoscope, using the site selection box 71. The site selection box 71 constitutes an interface for inputting a site on the screen. In the present embodiment, as the site selection box, a box for selecting a site of the large intestine is displayed on the screen 70A. FIG. 11 is a diagram illustrating an example of the site selection box. As illustrated in the figure, in the present embodiment, a schema diagram Sc of the large intestine is displayed in a box defined by a frame with a rectangular outer shape, and the selection of a site is accepted on the schema diagram Sc. In the example illustrated in FIG. 11, a case where the large intestine is selected from three sites is illustrated. Specifically, a case where the large intestine is selected from three sites of "ASCENDING COLON", "TRANSVERSE COLON", and "DESCENDING COLON" is illustrated. Note that FIG. 11 is an example of division of sites, and it is also possible to divide and select the sites in more detail.

Figure 12C:
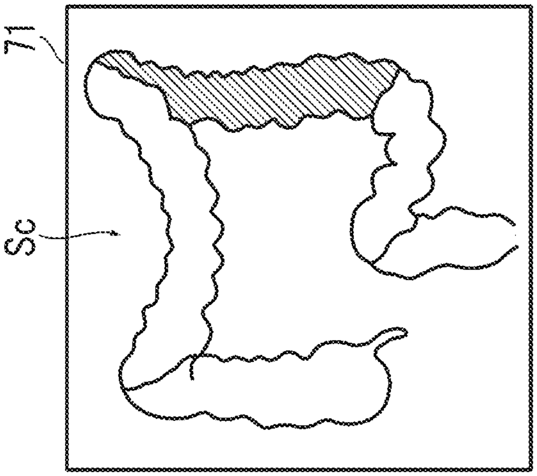
FIGS. 12A to 12C are diagrams illustrating examples of display of a site being selected.
Figure 12B:
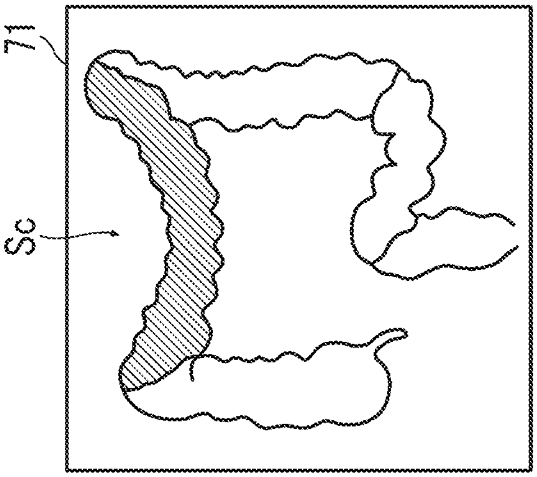
Figure 12A:
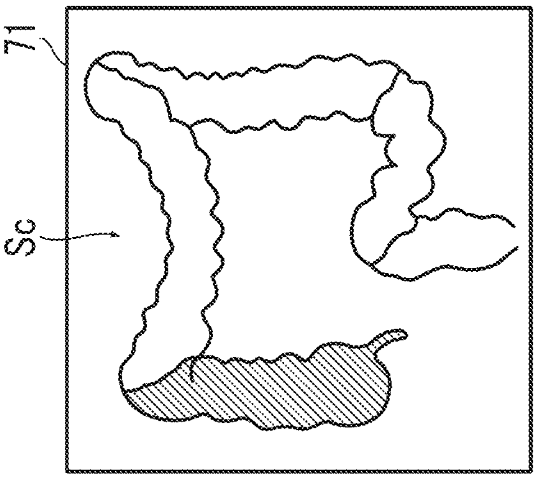

FIGS. 12A to 12C are diagrams illustrating examples of display of the site being selected. FIG. 12A illustrates an example of a case in which the "ascending colon" is selected. FIG. 12B illustrates an example of a case in which the "transverse colon" is selected. FIG. 12C illustrates an example of a case in which the "descending colon" is selected. As illustrated in each diagram of FIGS. 12A to 12C, in the schema diagram Sc, the selected site is displayed to be distinguishable from the other sites. In the example illustrated in FIGS. 12A to 12C, the selected site is displayed to be distinguishable from the other sites by changing the color of the selected site. In addition, the selected site may be distinguished from the other sites by making the selected site blink or the like.

Figure 13:
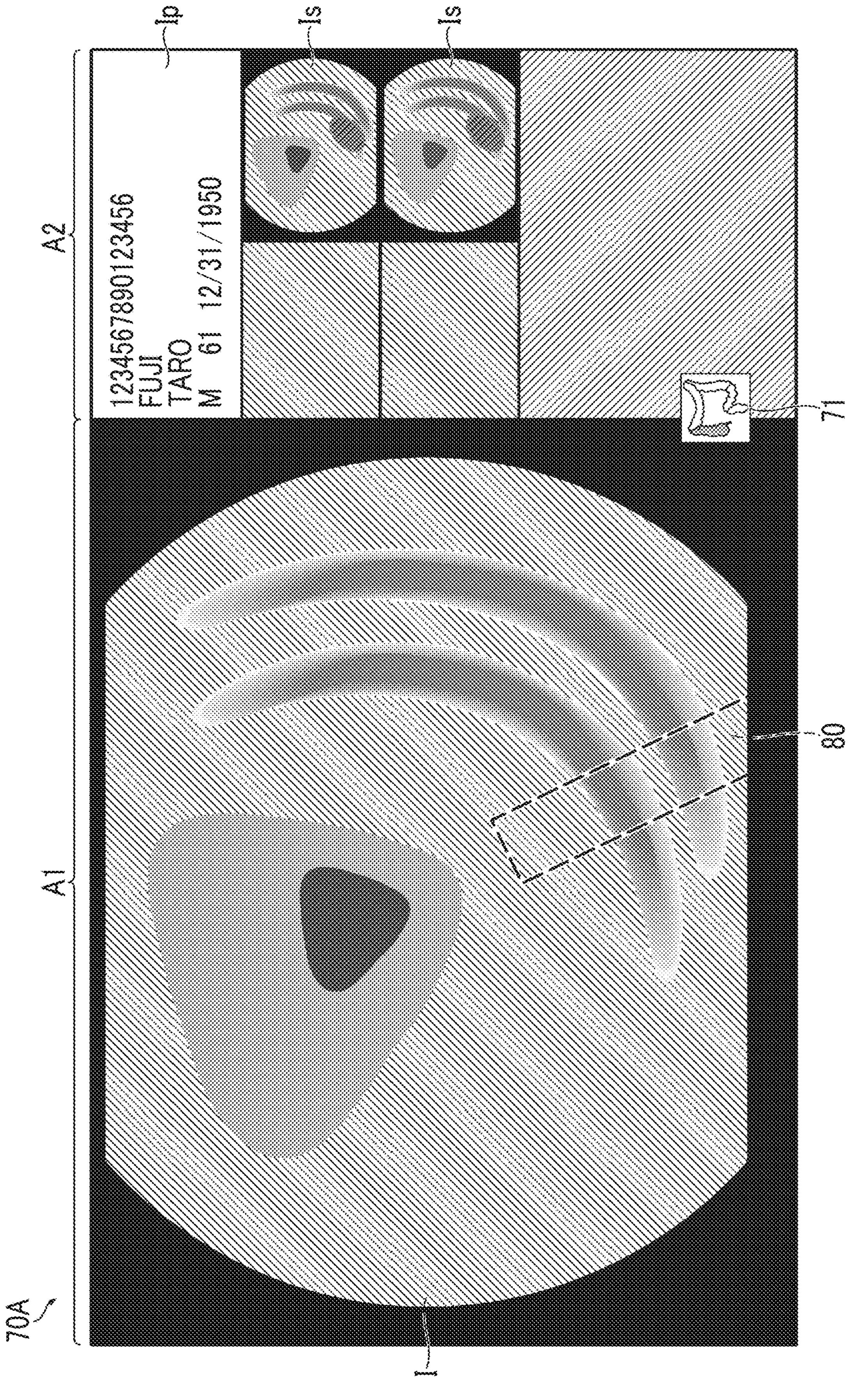
FIG. 13 is a diagram illustrating an example of a display position of a site selection box.

FIG. 13 is a diagram illustrating an example of a display position of the site selection box. The site selection box 71 is displayed at a fixed position on the screen 70A. The position where the site selection box 71 is displayed is set in the vicinity of the position where the treatment tool 80 appears in the endoscopic image displayed in the main display region A1. As an example, the position is set to a position that does not overlap the endoscopic image I displayed in the main display region A1 and that is adjacent to the position where the treatment tool 80 appears. The position is a position in substantially the same direction as the direction in which the treatment tool 80 appears, with respect to a center of the endoscopic image I displayed in the main display region A1. In the present embodiment, as illustrated in FIG. 13, the treatment tool 80 is displayed from the lower right position of the endoscopic image I displayed in the main display region A1. Thus, the position where the site selection box 71 is displayed is set to the lower right position with respect to the center of the endoscopic image I displayed in the main display region A1.

Figure 14:
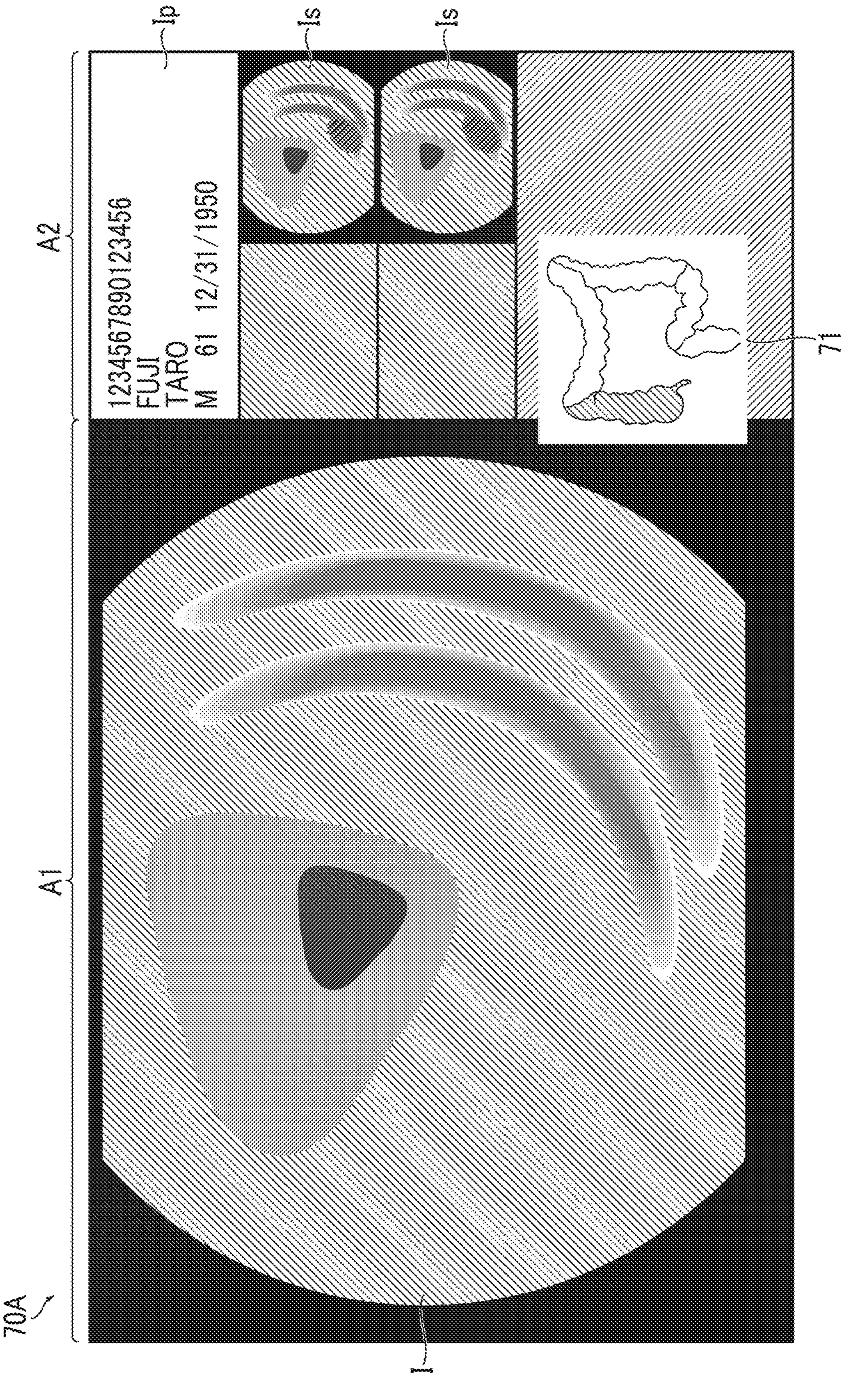
FIG. 14 is a diagram illustrating an example of emphasized display of a site selection box.

In a case where the site is selected, the display control unit 64 displays the site selection box 71 in an emphasized manner for a fixed time (time T1). FIG. 14 is a diagram illustrating an example of emphasized display of the site selection box. As illustrated in the figure, in the present embodiment, the site selection box 71 is displayed in an emphasized manner by being enlarged. In addition, as the emphasizing method, methods such as changing a color from a normal display form, enclosing with a frame, and blinking, and a method of a combination thereof can be adopted. The method of selecting the site will be described below.

Note that, in the endoscope system 10 of the present embodiment, in a case where the site selection box 71 is first displayed on the screen 70A, the site selection box 71 is displayed on the screen 70A in a state where one site is selected in advance.

Here, in the present embodiment, the condition for displaying the site selection box 71 on the screen 70A is a case where the specific region is detected by the specific region detection unit 63C. In the present embodiment, in a case where the ileocecum is detected as the specific region, the site selection box 71 is displayed on the screen 70A. In this case, the display control unit 64 displays the site selection box 71 on the screen 70A in a state where a site to which the specific region belongs is selected in advance. For example, in a case where the specific region is the ileocecum, the site selection box 71 is displayed on the screen in a state where the ascending colon is selected (refer to FIG. 12A). Further, for example, in a case where the specific region is the hepatic flexure, the site selection box 71 may be displayed on the screen in a state where the transverse colon is selected, and in a case where the specific region is the splenic flexure, the site selection box 71 may be displayed on the screen in a state where the descending colon is selected.

In this manner, in a case where the site selection box 71 is displayed on the screen 70A with the detection of the specific region as a trigger, by displaying the site selection box 71 on the screen 70A in a state where the site to which the specific region belongs is selected in advance, it is possible to save time and effort for selecting a site. Accordingly, it is possible to efficiently input information on the site.

In general, the operator ascertains the position of the distal end portion 21A of the endoscope during the examination from an insertion length of the endoscope, the image during the examination, the feel during operation in the endoscope operation, and the like. With the endoscope system 10 of the present embodiment, in a case where the operator determines that the site selected in advance is different from the actual site, the operator can correct the selected site. On the other hand, in a case where the operator determines that the site selected in advance is correct, the selection operation by the operator is not necessary. Accordingly, it is possible to save the operator's time and effort, and to accurately input information on the site. Further, information on an appropriate site can be associated with the endoscopic image, the lesion information acquired during the examination, treatment information during the examination, and the like.

Moreover, it is possible to save the operator's time and effort and to input information on an appropriate site by adopting a configuration in which, for a site including a region (for example, ileocecum) that can be detected with high accuracy by the specific region detection unit 63C, the site is selected in advance, and for a site (for example, transverse colon) not including a region that can be detected with high accuracy by the specific region detection unit 63C, the selection from the operator is accepted without selecting the site in advance.

Note that, in a case where the site selection box 71 is displayed on the screen 70A in a state where a specific site is selected in advance, in a case where the site selection box 71 is first displayed on the screen 70A, the display control unit 64 displays the site selection box 71 in an emphasized manner for a fixed time (time T1) (refer to FIG. 14).

Time T1 for which the site selection box 71 is displayed in an emphasized manner is determined in advance. Time T1 may be arbitrarily set by the user.

Figure 15B:
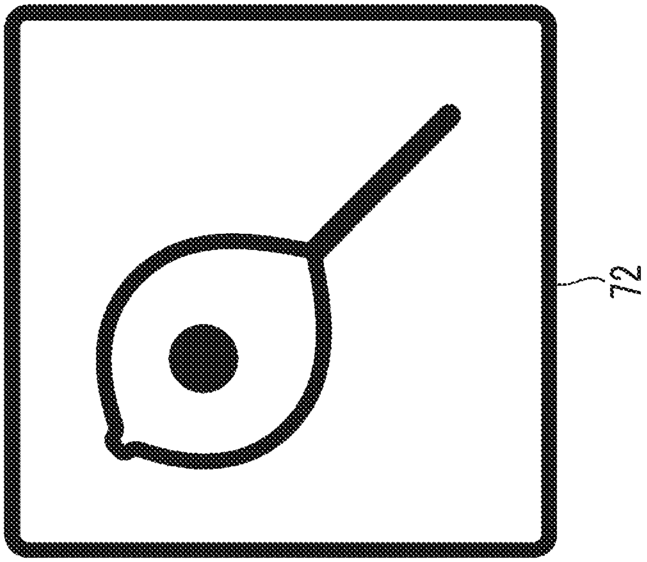
FIGS. 15A and 15B are diagrams illustrating examples of a treatment tool detection mark.
Figure 15A:
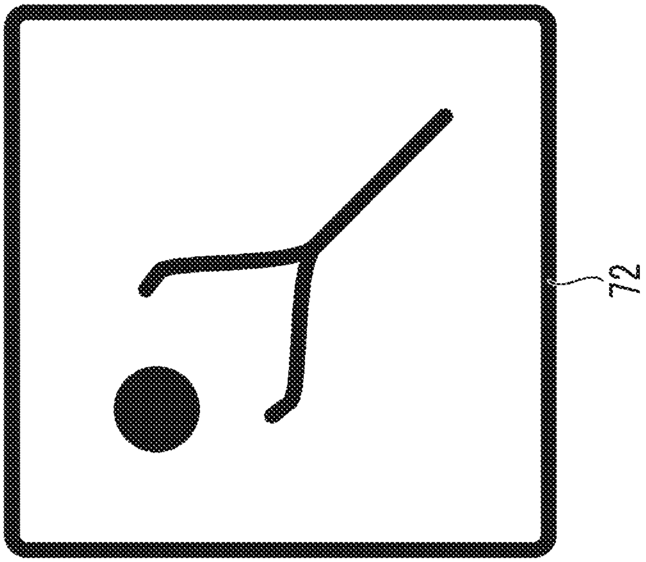

In a case where the treatment tool is detected, the display control unit 64 displays a mark indicating detection of the treatment tool (treatment tool detection mark) on the screen 70A. FIGS. 15A and 15B are diagrams illustrating examples of the treatment tool detection mark. As illustrated in the figures, different marks are used for detected treatment tools, respectively. FIG. 15A is a diagram illustrating an example of a treatment tool detection mark 72 displayed in a case where biopsy forceps are detected. FIG. 15B is a diagram illustrating an example of the treatment tool detection mark 72 displayed in a case where a snare is detected. A symbol depicting the corresponding treatment tool is used as the treatment tool detection mark in each figure. In addition, the treatment tool detection mark can be represented graphically.

Figure 16:
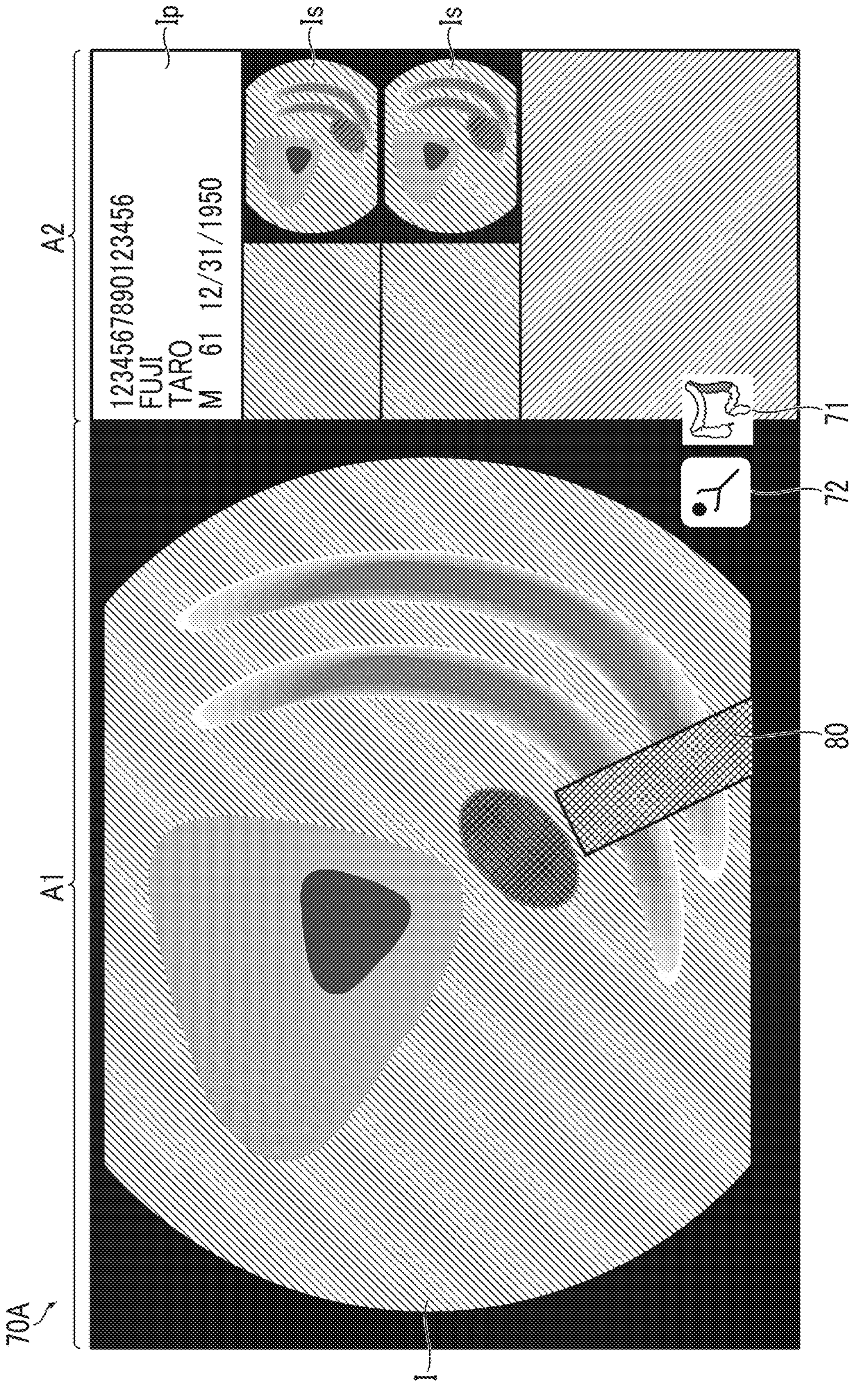
FIG. 16 is a diagram illustrating an example of a display position of a treatment tool detection mark.

FIG. 16 is a diagram illustrating an example of the display position of the treatment tool detection mark. The treatment tool detection mark 72 is displayed at a fixed position on the screen 70A. The position where the treatment tool detection mark 72 is displayed is set in the vicinity of the position where the treatment tool 80 appears in the endoscopic image I displayed in the main display region A1. As an example, the position is set to a position that does not overlap the endoscopic image I displayed in the main display region A1 and that is adjacent to the position where the treatment tool 80 appears. The position is a position in substantially the same direction as the direction in which the treatment tool 80 appears, with respect to the center of the endoscopic image I displayed in the main display region A1. In the present embodiment, as illustrated in FIG. 16, the treatment tool 80 is displayed from the lower right position of the endoscopic image I displayed in the main display region A1. Thus, the position where the treatment tool detection mark 72 is displayed is set to the lower right position with respect to the center of the endoscopic image I displayed in the main display region A1. In a case where the site selection box 71 is simultaneously displayed, the treatment tool detection mark 72 is displayed side by side with the site selection box 71. In this case, the treatment tool detection mark 72 is displayed at a position closer to the treatment tool 80 than the site selection box 71.

In this manner, by displaying the treatment tool detection mark 72 in the vicinity of the position where the treatment tool 80 appears in the endoscopic image I, the user can easily recognize that the treatment tool 80 has been detected (recognized) from the endoscopic image I. That is, it is possible to improve visibility. The region where the treatment tool detection mark 72 is displayed on the screen 70A is an example of a fourth region.

Moreover, in a case where a specific condition is satisfied, the display control unit 64 displays a treatment name selection box 73 on the screen 70A. The treatment name selection box 73 is a region for selecting one treatment name from among a plurality of treatment names (specimen collection methods in a case of specimen collection) on the screen. The treatment name selection box 73 constitutes an interface for inputting the treatment name on the screen. In the present embodiment, the treatment name selection box 73 is displayed after the treatment has ended. The end of the treatment is determined on the basis of the detection result of the treatment tool detection unit 63D. Specifically, in a case where the treatment tool 80 appearing in the endoscopic image I disappears from the endoscopic image I, and a fixed time (time T2) has elapsed from the disappearance, it is determined that the treatment has ended. For example, time T2 is 15 seconds. Time T2 may be arbitrarily set by the user. Time T2 is an example of the first time. By displaying the treatment name selection box 73 on the screen 70A at a timing when it is determined that the treatment by the operator has ended, an input of the treatment name can be accepted without hindering the treatment work of the operator. The timing when the treatment name selection box 73 is displayed can be set to a timing when the treatment tool detection unit 63D has detected the treatment tool, a timing when a fixed time has elapsed after the treatment tool detection unit 63D has detected the treatment tool, and a timing when the end of the treatment name is determined by other image recognition. Further, the timing when the treatment name selection box 73 is displayed may be set according to the detected treatment tool.

Figure 17B:
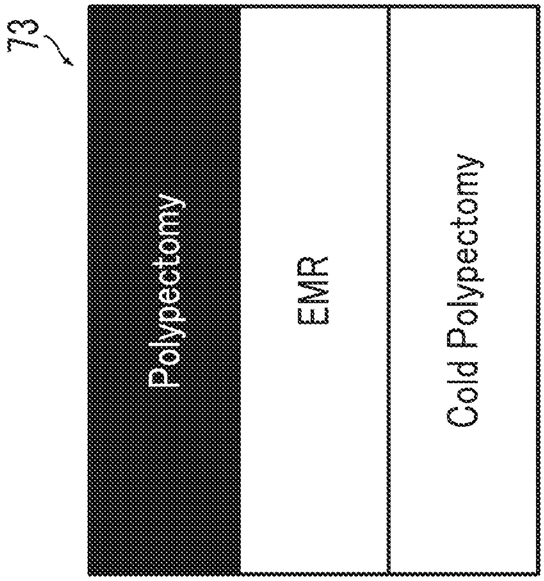
FIGS. 17A and 17B are diagrams illustrating examples of a treatment name selection box.
Figure 17A:
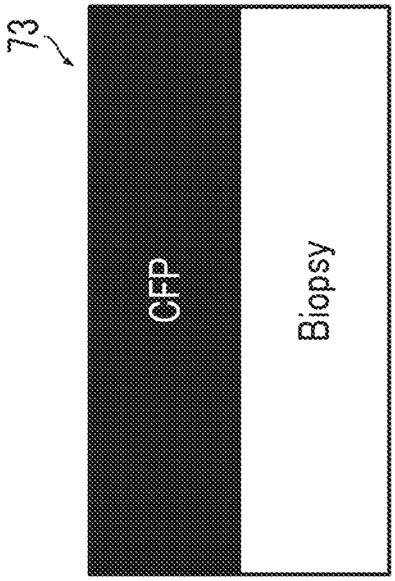

FIGS. 17A and 17B are diagrams illustrating examples of the treatment name selection box.

As illustrated in the figures, the treatment name selection box 73 is configured by a so-called list box, and selectable treatment names are displayed in a list. In the example illustrated in FIGS. 17A and 17B, a case in which a list of selectable treatment names is displayed in a vertical line is illustrated.

In the treatment name selection box 73, the name corresponding to the treatment tool 80 detected from the endoscopic image I is displayed. FIG. 17A illustrates an example of the treatment name selection box 73 displayed on the screen in a case where the treatment tool 80 detected from the endoscopic image I is the "biopsy forceps". As illustrated in the figure, in a case where the detected treatment tool is the "biopsy forceps", "cold forceps polypectomy (CFP)" and "Biopsy" are displayed as the selectable treatment names. FIG. 17B illustrates an example of the treatment name selection box 73 displayed on the screen in a case where the treatment tool 80 detected from the endoscopic image I is the "snare". As illustrated in the figure, in a case where the detected treatment tool is the "snare", "Polypectomy", "endoscopic mucosal resection (EMR)", and "Cold Polypectomy" are displayed as the selectable treatment names.

In FIGS. 17A and 17B, a treatment name displayed in white characters on a black background indicates the treatment name being selected. In the example illustrated in FIG. 17A, a case where "CFP" is selected is illustrated. Further, in the example illustrated in FIG. 17B, a case where "Polypectomy" is selected is illustrated.

In a case where the treatment name selection box 73 is displayed on the screen, the display control unit 64 displays the treatment name selection box 73 on the screen in a state where one treatment name is selected in advance. Further, in a case where the treatment name selection box 73 is displayed on the screen, the display control unit 64 displays the treatment names in a predetermined arrangement in the treatment name selection box 73. Therefore, the display control unit 64 controls the display of the treatment name selection box 73 by referring to the table.

FIG. 18 is a diagram illustrating an example of the table.

As illustrated in the figure, in the table, pieces of information on "treatment tool", "treatment name to be displayed", "display rank", and "default option" are registered in association with each other. Here, the "treatment tool" in the same table is the type of the treatment tool to be detected from the endoscopic image I. The "treatment name to be displayed" is the treatment name to be displayed corresponding to the treatment tool. The "display rank" is a display order of each treatment name to be displayed. In a case where the treatment names are displayed in a vertical line, the treatment names are ranked 1, 2, 3, and the like from the top. The "default option" is the treatment name that is first selected.

The "treatment name to be displayed" may not necessarily be the treatment names of all the treatments executable by the corresponding treatment tool. It is preferable to limit the number of treatment names to a smaller number. That is, it is preferable to limit the number to a specified number or less. In this case, in a case where the number of types of treatments executable by a certain treatment tool exceeds a specified number, the number of treatment names to be registered in the table (treatment names displayed in the treatment name selection box) is limited to a specified number or less.

In a case where the number of treatment names to be displayed is limited, a treatment name with a high execution frequency is chosen from among the treatment names of the executable treatments. For example, in a case where the "treatment tool" is the "snare", (1) "Polypectomy", (2) "EMR", (3) "Cold Polypectomy", (4) "EMR [en bloc]", (5) "EMR [piecemeal: <5 pieces]", (6) "EMR [piecemeal: ≥5 pieces]", (7) "endoscopic submucosal resection with a ligation device (ESMR-L)", (8) "endoscopic mucosal resection using a cap-fitted endoscope (EMR-C)", and the like are exemplified as the treatment names of executable treatments. It is assumed that (1) "Polypectomy", (2) "EMR", (3) "Cold Polypectomy", (4) "EMR [en bloc]", (5) "EMR [piecemeal: <5 pieces]", (6) "EMR [piecemeal: ≥5 pieces]", (7) "ESMR-L", and (8) "EMR-C" are arranged in the descending order of the execution frequency, and the specified number is three. In this case, three of (1) Polypectomy, (2) EMR, and (3) Cold Polypectomy are registered in the table as the "treatment name to be displayed". Note that each of (4) "EMR [en bloc]", (5) "EMR [piecemeal: <5 pieces]", and (6) "EMR [piecemeal: ≥5 pieces]" is a treatment name in a case of inputting a detailed treatment name by EMR. (4) EMR [en bloc] is a treatment name in a case of the en bloc resection by EMR. (5) EMR [piecemeal: <5 pieces] is a treatment name in a case of the piecemeal resection by EMR with less than 5 pieces. (6) EMR [piecemeal: ≥5 pieces] is a treatment name in a case of the piecemeal resection by EMR with 5 pieces or more.

The specified number can be determined for each treatment tool. For example, the number (specified number) of treatment names to be displayed for each treatment tool can be determined such that the specified number is two for the "biopsy forceps" and the specified number is three for the "snare". For the "biopsy forceps", for example, "Hot Biopsy" is exemplified as the executable treatment in addition to the "CFP" and the "Biopsy".

In this manner, by narrowing down the treatment names with a high execution frequency (treatment names having a high probability of being selected) and displaying the options (selectable treatment names) in the treatment name selection box 73, the user can efficiently select the treatment name. In a case where a plurality of treatments can be executed by the same treatment tool, the detection of the treatment (treatment name) executed by the treatment tool may be more difficult than the detection of the type of the treatment tool (image recognition). By associating the treatment name that may be executed with the treatment tool in advance and allowing the operator to select the treatment name, it is possible to select an appropriate treatment name with a small number of operations.

The "display rank" is ranked 1, 2, 3, and the like in the descending order of the execution frequency. Normally, the higher the execution frequency is, the higher the selection frequency is, so the descending order of the execution frequency is synonymous with the descending order of the selection frequency.

In the "default option", the treatment name with the highest execution frequency among the treatment names to be displayed is selected. The highest execution frequency is synonymous with the highest selection frequency.

In the example illustrated in FIG. 18, in a case where the "treatment tool" is the "biopsy forceps", the "treatment name to be displayed" is "CFP" and "Biopsy". Then, the "display rank" is in the order of "CFP" and "Biopsy" from the top, and the "default option" is "CFP" (refer to FIG. 17A).

Further, in a case where the "treatment tool" is the "snare", the "treatment name to be displayed" is "Polypectomy", "EMR", and "Cold Polypectomy". Then, the "display rank" is in the order of "Polypectomy", "EMR", and "Cold Polypectomy" from the top, and the "default option" is "Polypectomy" (refer to FIG. 17B).

The display control unit 64 chooses treatment names to be displayed in the treatment name selection box 73 by referring to the table on the basis of the information on the treatment tool detected by the treatment tool detection unit 63D. Then, the chosen treatment names are arranged according to the information on the display rank registered in the table, and the treatment name selection box 73 is displayed on the screen. The treatment name selection box 73 is displayed on the screen in a state where one treatment name is selected according to the information on the default option registered in the table. In this manner, by displaying the treatment name selection box 73 in a state where one treatment name is selected in advance, in a case where there is no need to change, it is possible to save time and effort for the selection, and to efficiently input the information on the treatment name. Further, by setting the treatment name selected in advance as the treatment name of the treatment with a high execution frequency (=treatment with a high selection frequency), it is possible to save time and effort for the change. Further, by arranging the treatment names to be displayed in the treatment name selection box 73 in the descending order of the execution frequency (=descending order of selection frequency), the user can efficiently select the treatment name. Moreover, by narrowing down and displaying the options, the user can efficiently select the treatment name. The display content and the display order of the treatment name can be set for each hospital (including examination facility) and for each device. Further, the default option may be set to the previously executed treatment name during the examination. Since the same treatment may be repeated during the examination, it is possible to save time and effort for the change by selecting the previous treatment name as the default.

Figure 19:
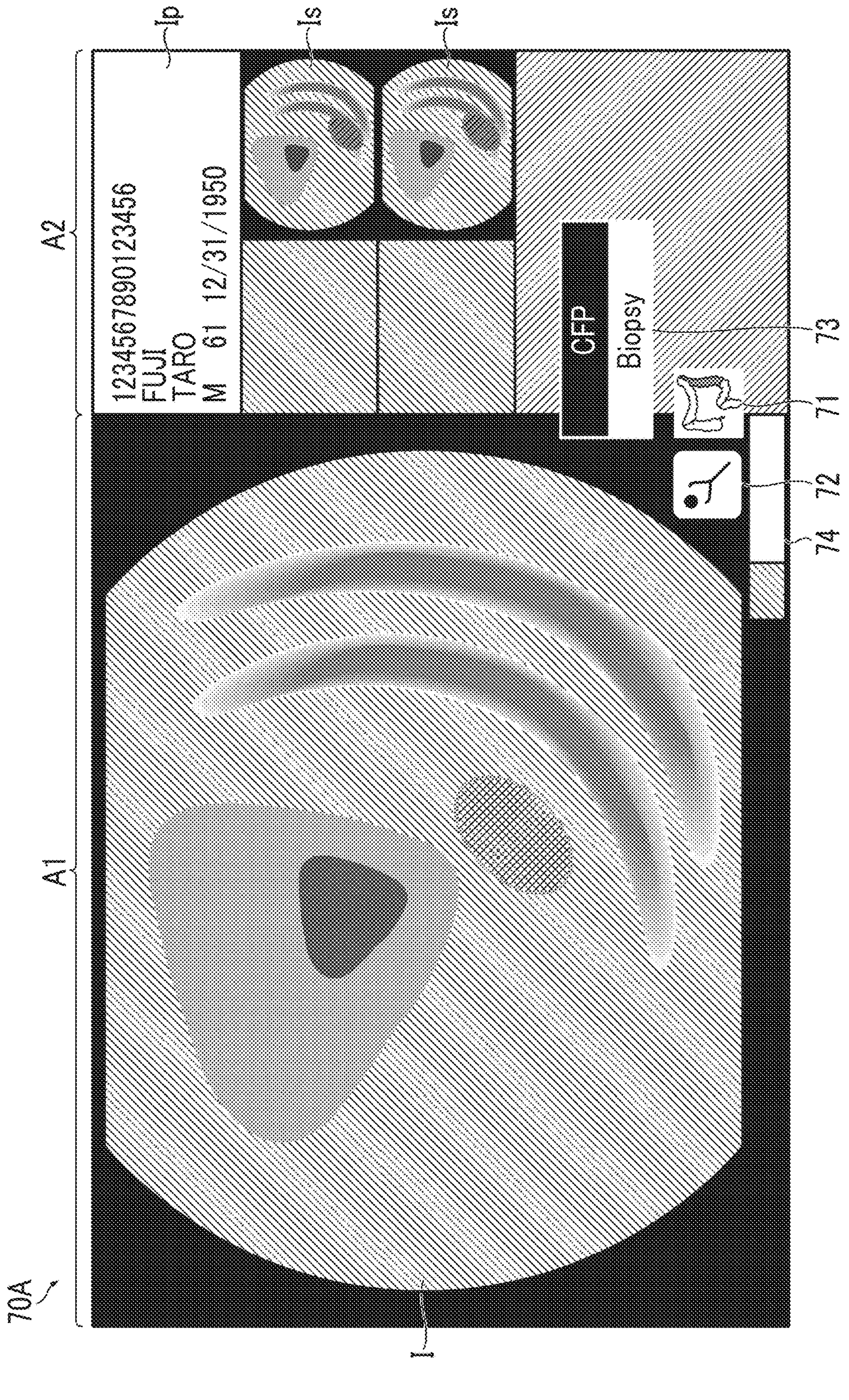
FIG. 19 is a diagram illustrating an example of a display position of a treatment name selection box.

FIG. 19 is a diagram illustrating an example of the display position of the treatment name selection box. The treatment name selection box 73 is displayed at a fixed position on the screen 70A. More specifically, the treatment name selection box 73 is displayed as a pop-up at a fixed position. In the present embodiment, the treatment name selection box 73 is displayed in the vicinity of the treatment tool detection mark 72. More specifically, the treatment name selection box 73 is displayed adjacent to the treatment tool detection mark 72. In the example illustrated in FIG. 19, a case in which the treatment name selection box 73 is displayed adjacent to an upper right portion of the treatment tool detection mark 72 is illustrated. Since the treatment name selection box 73 is displayed adjacent to the treatment tool detection mark 72, the treatment name selection box 73 is displayed in the vicinity of the position where the treatment tool appears in the endoscopic image I. In this manner, by displaying the treatment name selection box 73 in the vicinity of the position where the treatment tool 80 appears in the endoscopic image I, it is easier for the user to recognize the presence of the treatment name selection box 73. That is, it is possible to improve visibility. The region where the treatment name selection box 73 is displayed on the screen is an example of a second region.

Note that FIG. 19 illustrates a display example in a case where the "biopsy forceps" are detected as the treatment tool. In this case, the treatment name selection box 73 corresponding to the "biopsy forceps" is displayed (refer to FIG. 17A).

The display control unit 64 displays the treatment name selection box 73 on the screen 70A for a fixed time (time T3). For example, time T3 is 15 seconds. Time T3 may be arbitrarily set by the user. Time T3 is an example of a second time. The display time for the treatment name selection box 73 may be decided according to the detected treatment tool. Further, the display time for the treatment name selection box 73 may be set by the user.

The user can select the treatment name while the treatment name selection box 73 is displayed on the screen. The selection method will be described later.

As described above, the treatment name selection box 73 is displayed on the screen in a state where one treatment name is selected in advance. The user performs selection processing in a case where the treatment name selected by default is different from the actual treatment name. For example, in a case where the treatment tool used is the "biopsy forceps", the treatment name selection box 73 is displayed on the screen 70A in a state where "CFP" is selected, but in a case where the treatment actually performed is "Biopsy", the selection processing is performed.

In a case where a fixed time (time T3) has elapsed from the display start of the treatment name selection box 73, and the treatment name selection box 73 disappears from the screen 70A, the selection is confirmed. That is, in the endoscope system 10 of the present embodiment, the selection can be automatically confirmed without performing selection confirmation processing separately. Therefore, for example, in a case where the treatment name selected by default is correct, the treatment name can be input without performing any input operation. Accordingly, it is possible to greatly reduce time and effort for inputting the treatment name.

Figure 20:
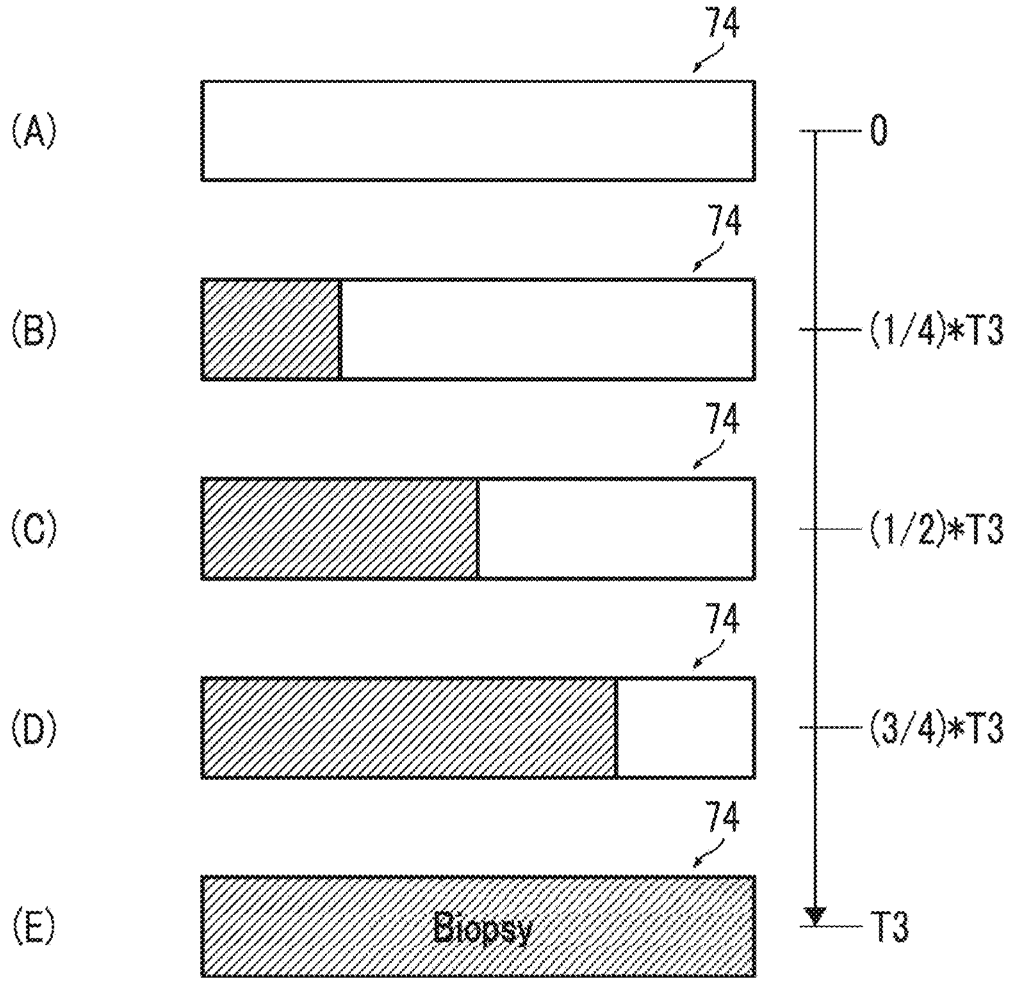
FIG. 20 is a diagram illustrating an example of a time bar.

Since the time for which the selection operation of the treatment name is possible is limited, in the endoscope system 10 of the present embodiment, the remaining time until the acceptance of the selection is ended is displayed on the screen. In the present embodiment, the remaining time until the acceptance of the selection is ended is displayed by displaying a time bar 74 at a fixed position on the screen. FIG. 20 is a diagram illustrating an example of the time bar. The figure illustrates a temporal change of the display of the time bar 74. (A) of FIG. 20 illustrates the display of the time bar 74 in a case where the display of the treatment name selection box 73 is started. Further, (B) to (D) of FIG. 20 respectively illustrate the display of the time bar 74 after a time of (¼)*T3 has elapsed from the start of the display of the treatment name selection box 73, after a time of (½)*T3 has elapsed from the start of the display of the treatment name selection box 73, and after a time of (¾)*T3 has elapsed from the start of the display of the treatment name selection box 73. Further, (E) of FIG. 20 illustrates the display of the time bar 74 in a case where a time of T3 has elapsed from the start of the display of the treatment name selection box 73. That is, the display of the time bar 74 in a case where the acceptance of the selection is ended is illustrated. As illustrated in the figure, in the time bar 74 in this example, the remaining time is indicated by a bar in a horizontal direction in which the bar is filled from left to right. In this case, a white portion indicates the remaining time. The display of the remaining time can be displayed by a numerical value instead of the time bar or in addition to the time bar. That is, the remaining time can also be counted down and displayed in seconds.

As described above, in the endoscope system 10 of the present embodiment, the selection is automatically confirmed by the end of the acceptance of the selection of the treatment name. In a case where the acceptance of the selection of the treatment name is ended, the treatment name for which the selection is confirmed is displayed at the display position of the time bar 74 as illustrated in (E) of FIG. 20. The user can check the treatment name selected by himself/herself by viewing the display of the time bar 74. (E) of FIG. 20 illustrates an example of a case where "Biopsy" is selected.

As illustrated in FIG. 19, the time bar 74 is displayed in the vicinity of the display position of the treatment tool detection mark 72. Specifically, the time bar 74 is displayed adjacent to the treatment tool detection mark 72. In the example illustrated in FIG. 19, a case in which the time bar 74 is displayed adjacently under the treatment tool detection mark 72 is illustrated. Since the time bar 74 is displayed adjacent to the treatment tool detection mark 72, the time bar 74 is displayed in the vicinity of the position where the treatment tool appears in the endoscopic image I. In this manner, by displaying the time bar 74 in the vicinity of the position where the treatment tool 80 appears in the endoscopic image I, it is easier for the user to recognize the presence of the time bar 74. The region where the time bar 74 is displayed on the screen is an example of a third region.

The time (time T3) for which the treatment name selection box 73 is displayed extends under certain conditions. Specifically, the time extends in a case where the selection processing of the treatment name is performed. The extension of the time is performed by resetting the countdown. Therefore, the display time extends by the difference between time T3 and the remaining time at a time point when the selection processing is performed. For example, in a case where the remaining time at the time point when the selection processing is performed is ΔT, the time extends by (T3−ΔT). In other words, the selection is possible again for time T3 from the time point when the selection processing is performed.

The extension of the display time is executed each time the selection processing is performed. That is, the countdown is reset each time the selection processing is performed, so that the display time extends. Further, accordingly, the period for the acceptance of the selection of the treatment name extends.

Figure 21:
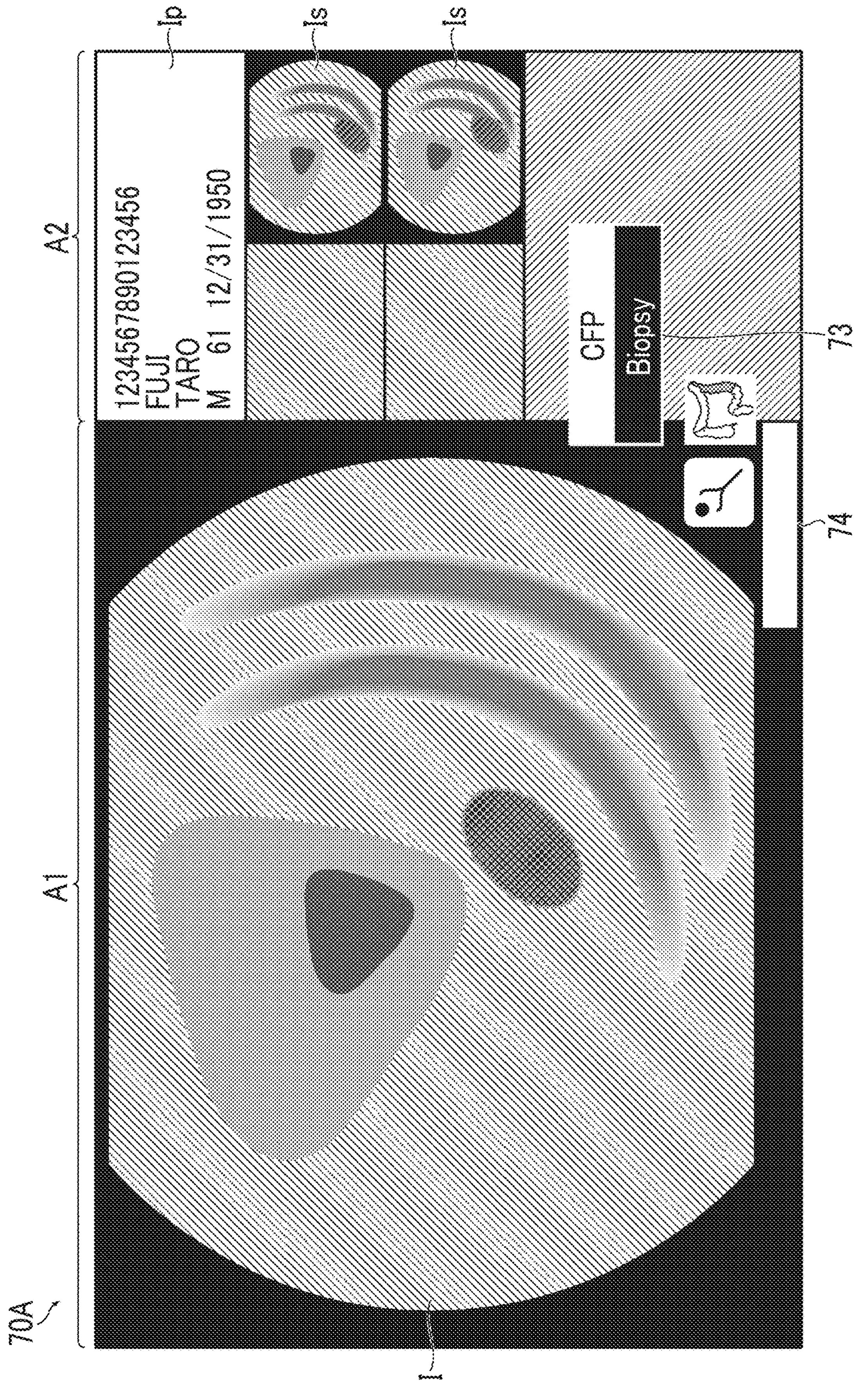
FIG. 21 is a diagram illustrating an example of display of a screen immediately after a user performs selection processing of a treatment name.

FIG. 21 is a diagram illustrating an example of display of a screen immediately after the user performs the selection processing of the treatment name.

As illustrated in the figure, in a case where the user performs the selection processing of the treatment name, the display of the time bar 74 is reset.

Figure 22:
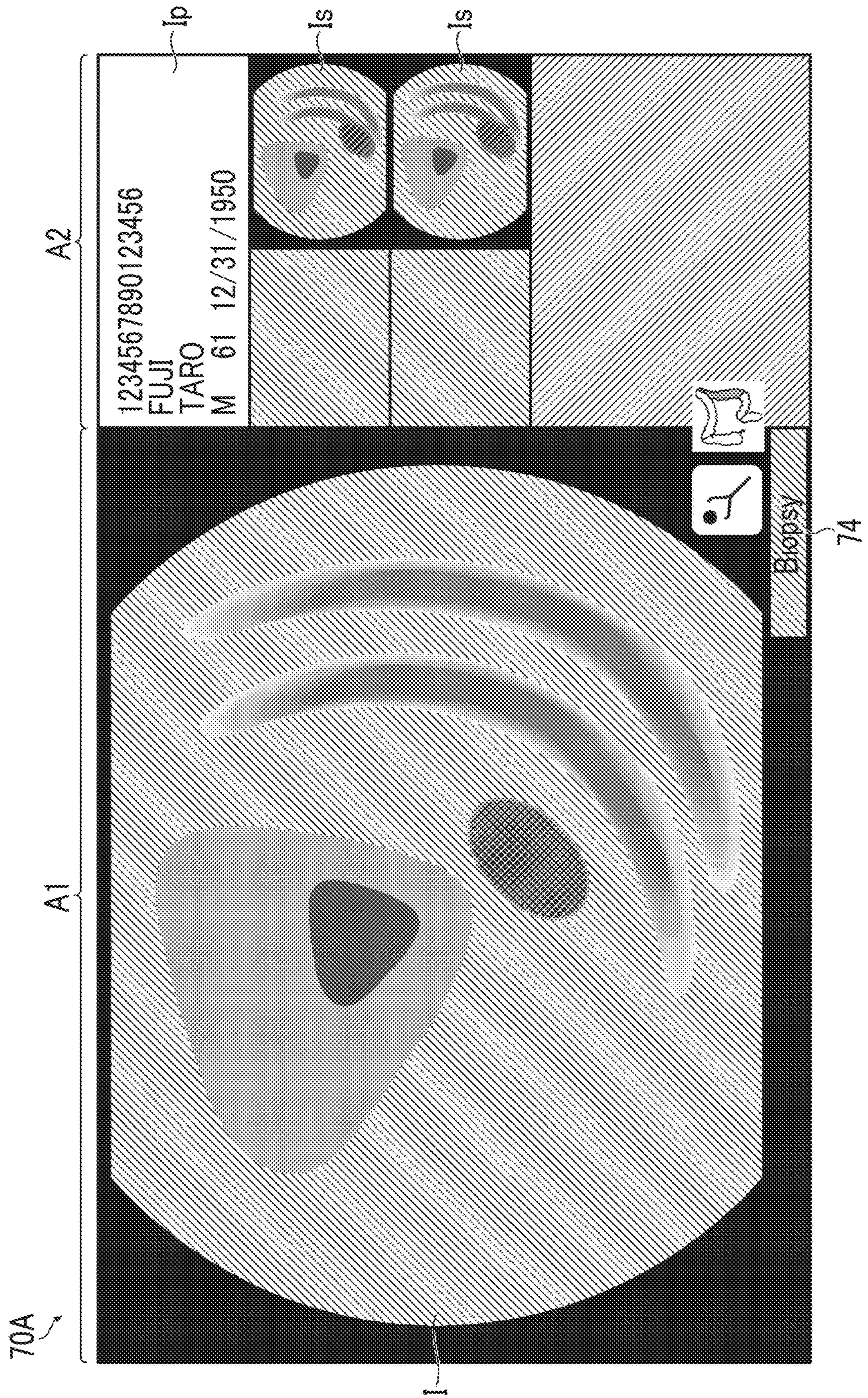
FIG. 22 is a diagram illustrating an example of display of a screen immediately after acceptance of selection of a treatment name is ended.

FIG. 22 is a diagram illustrating an example of the display of the screen immediately after the acceptance of the selection of the treatment name is ended.

As illustrated in the figure, in a case where the acceptance of the selection of the treatment name is ended, the display of the treatment name selection box 73 disappears. Meanwhile, the treatment name for which the selection is confirmed is displayed in the time bar 74. FIG. 22 illustrates an example of a case where "Biopsy" is selected.

Information on the treatment name for which the selection is confirmed is displayed at the display position of the time bar 74 for a fixed time (time T4). Then, after a fixed time has elapsed, the display disappears. In this case, the display of the treatment tool detection mark 72 also disappears.

Here, a method of selecting a site in a case where the site selection box 71 is displayed, and a method of selecting a treatment name in a case where the treatment name selection box 73 is displayed will be described.

The selection of the site and the selection of the treatment name are both performed using the input device 50. In particular, in the present embodiment, the selection is performed using the foot switch constituting the input device 50. Each time the foot switch is stepped on, the operation signal is output.

First, the method of selecting a site will be described. In principle, the selection of the site is always accepted after the start of the display of the site selection box 71 until the examination ends. As an exception, the acceptance of the selection of the site is stopped while the selection of the treatment name is being accepted. That is, the acceptance of the selection of the site is stopped while the treatment name selection box 73 is being displayed.

In a case where the foot switch is operated in a state where the selection of the site is being accepted, the site being selected is switched in order. In the present embodiment, (1) ascending colon, (2) transverse colon, and (3) descending colon are looped and switched in this order. Therefore, for example, in a case where the foot switch is operated once in a state where the "ascending colon" is being selected, the selected site is switched from the "ascending colon" to the "transverse colon". Similarly, in a case where the foot switch is operated once in a state where the "transverse colon" is being selected, the selected site is switched from the "transverse colon" to the "descending colon". Moreover, in a case where the foot switch is operated once in a state where the "descending colon" is being selected, the selected site is switched from the "descending colon" to the "ascending colon". In this manner, the selected site is switched in order each time the foot switch is operated once. The information on the selected site is stored in the main storage unit or the auxiliary storage unit. The information on the selected site can be used as information for specifying the site under observation. For example, in a case where the static image is captured during the examination, the site where the static image is captured can be specified after the examination by recording (storing) the captured static image and the information on the site being selected in association with each other. The information on the site being selected may be recorded in association with the time information during the examination or the elapsed time from the examination start. Accordingly, for example, in a case where the image captured by the endoscope is recorded as a video, the site can be specified from the time point or elapsed time. Further, the information on the site being selected may be recorded in association with the information on a lesion or the like detected by the image recognition processing unit 63. For example, in a case where the lesion part or the like is detected, the information on the lesion part or the like can be recorded in association with the information on the site being selected in a case where the lesion part or the like is detected.

Next, the method of selecting the treatment name will be described. As described above, the selection of the treatment name is accepted only while the treatment name selection box 73 is displayed. Similar to the case of the selection of the site, in a case where the foot switch is operated, the treatment name being selected is switched in order. The switching is performed according to the display rank. Therefore, the treatment names are switched in order from the top. Further, the treatment names are looped and switched. For example, in a case of the treatment name selection box 73 illustrated in FIG. 17A, a selection target is alternately switched between "CFP" and "Biopsy" each time the foot switch is operated once. That is, in a case where the foot switch is operated once in a state where "CFP" is being selected, the selection target is switched to "Biopsy", and in a case where the foot switch is operated once in a state where "Biopsy" is being selected, the selection target is switched to "CFP". Further, for example, in a case of the treatment name selection box 73 illustrated in FIG. 17B, the selection target is looped and switched in the order of (1) "Polypectomy", (2) "EMR", and (3) "Cold Polypectomy" each time the foot switch is operated once. Specifically, in a case where the foot switch is operated once in a state where the "Polypectomy" is being selected, the selection target is switched to "EMR". Further, in a case where the foot switch is operated once in a state where "EMR" is being selected, the selection target is switched to "Cold Polypectomy". Further, in a case where the foot switch is operated once in a state where the "Cold Polypectomy" is being selected, the selection target is switched to "Polypectomy". The information on the selected treatment name is stored together with the information on the detected treatment tool in the main storage unit or the auxiliary storage unit in association with the information on the site being selected.

[Examination Information Output Control Unit]

The examination information output control unit 65 outputs the examination information to the endoscope information management system 100. In the examination information, the endoscopic image captured during the examination, the information on the site input during the examination, the information on the treatment name input during the examination, the information on the treatment tool detected during the examination, and the like are included. For example, the examination information is output for each lesion or each time a specimen is collected. In this case, respective pieces of information are output in association with each other. For example, the endoscopic image in which the lesion part or the like is imaged is output in association with the information on the site being selected. Further, in a case where the treatment is performed, the information on the selected treatment name and the information on the detected treatment tool are output in association with the endoscopic image and the information on the site. Further, the endoscopic image captured separately from the lesion part or the like is always output to the endoscope information management system 100. The endoscopic image is output with the information of imaging date and time added.

[Display Device]

The display device 70 is an example of a display unit. For example, the display device 70 includes a liquid-crystal display (LCD), an organic electroluminescence (EL) display (OLED), or the like. In addition, the display device 70 includes a projector, a head-mounted display, and the like. The display device 70 is an example of a first display unit.

[Endoscope Information Management System]

Figure 23:
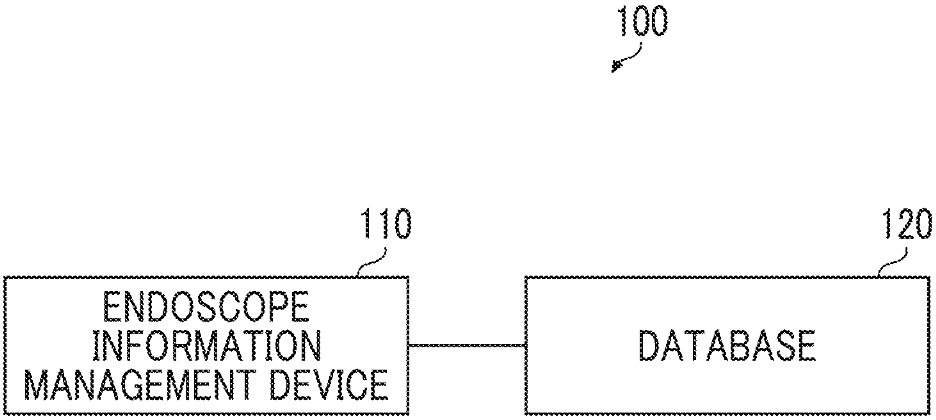
FIG. 23 is a block diagram illustrating an example of a system configuration of an endoscope information management system.

FIG. 23 is a block diagram illustrating an example of a system configuration of the endoscope information management system.

As illustrated in the figure, the endoscope information management system 100 mainly includes an endoscope information management device 110 and a database 120.

The endoscope information management device 110 collects a series of information (examination information) related to the endoscopy, and integrally manages the series of information. Further, the creation of an examination report is supported via the user terminal 200.

The endoscope information management device 110 includes, as a hardware configuration, a processor, a main storage unit, an auxiliary storage unit, a display unit, an operation unit, a communication unit, and the like. That is, the endoscope information management device 110 has a so-called computer configuration as the hardware configuration. For example, the processor is configured by a CPU. The processor of the endoscope information management device 110 is an example of a second processor. For example, the main storage unit is configured by a RAM. For example, the auxiliary storage unit is configured by a hard disk drive (HDD), a solid-state drive (SSD), a flash memory, or the like. The display unit is configured by a liquid-crystal display, an organic EL display, or the like. The operation unit is configured by a keyboard, a mouse, a touch panel, or the like. For example, the communication unit is configured by a communication interface connectable to a network. The endoscope information management device 110 is communicably connected to the endoscope system 10 via the communication unit. More specifically, the endoscope information management device 110 is communicably connected to the endoscopic image processing device 60.

Figure 24:
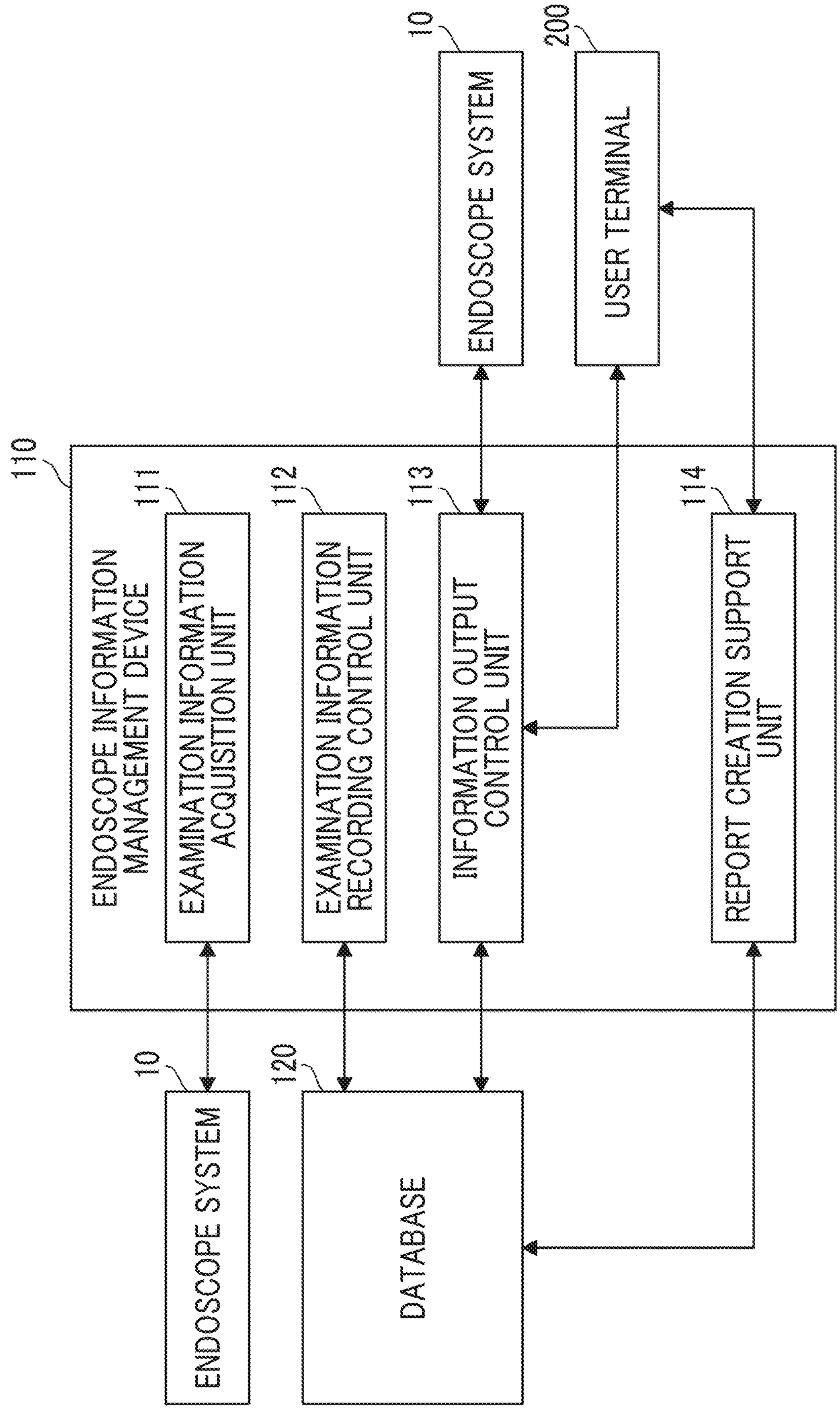
FIG. 24 is a block diagram of main functions of an endoscope information management device.

FIG. 24 is a block diagram of main functions of the endoscope information management device.

As illustrated in the figure, the endoscope information management device 110 has functions of an examination information acquisition unit 111, an examination information recording control unit 112, an information output control unit 113, a report creation support unit 114, and the like. Each function is realized by the processor executing a predetermined program. The auxiliary storage unit stores various programs executed by the processor, various kinds of data necessary for processing, and the like.

The examination information acquisition unit 111 acquires the series of information (examination information) related to the endoscopy from the endoscope system 10. In the information to be acquired, the endoscopic image captured during the examination, the information on the site input during the examination, the information on the treatment name, the information on the treatment tool, and the like are included. In the endoscopic image, a video and a static image are included.

The examination information recording control unit 112 records the examination information acquired from the endoscope system 10 in the database 120.

The information output control unit 113 controls the output of the information recorded in the database 120. For example, the information recorded in the database 120 is output to a request source in response to a request from the user terminal 200, the endoscope system 10, and the like.

The report creation support unit 114 supports the creation of the report on the endoscopy via the user terminal 200. Specifically, a report creation screen is provided to the user terminal 200 to support the input on the screen.

Figure 25:
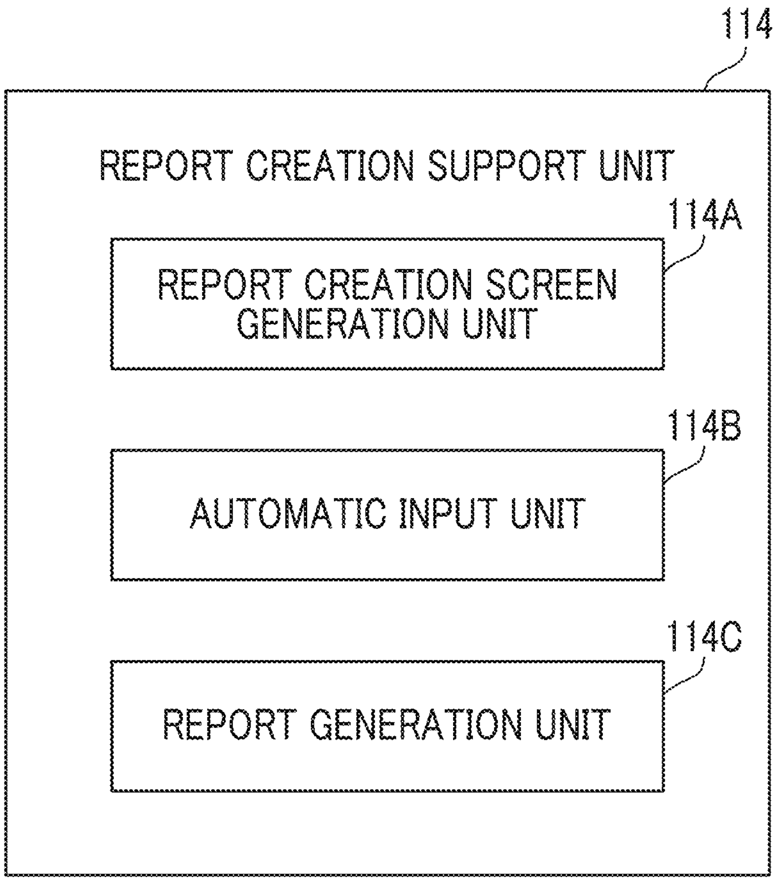
FIG. 25 is a block diagram of main functions of a report creation support unit.

FIG. 25 is a block diagram of main functions of the report creation support unit.

As illustrated in the figure, the report creation support unit 114 has functions of a report creation screen generation unit 114A, an automatic input unit 114B, a report generation unit 114C, and the like.

In response to the request from the user terminal 200, the report creation screen generation unit 114A generates a screen necessary for creating a report (report creation screen), and provides the screen to the user terminal 200.

Figure 26:
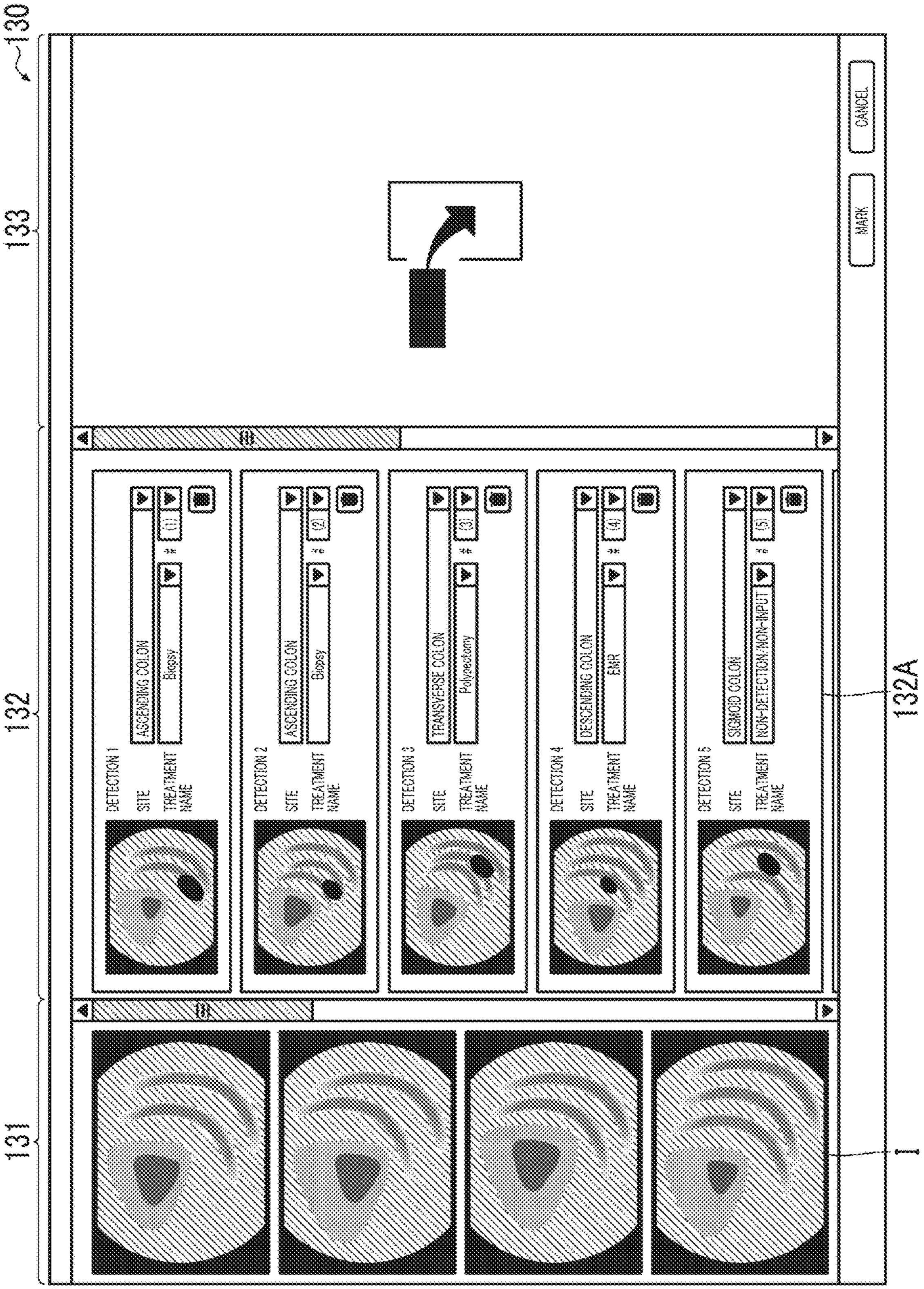
FIG. 26 is a diagram illustrating an example of a selection screen.

FIG. 26 is a diagram illustrating an example of a selection screen.

A selection screen 130 is one of the report creation screens, and is a screen for selecting a report creation target or the like. As illustrated in the figure, the selection screen 130 has a captured image display region 131, a detection list display region 132, a merge processing region 133, and the like.

The captured image display region 131 is a region in which the static images Is captured during the examination in one endoscopy are displayed. The captured static images Is are displayed in chronological order.

The detection list display region 132 is a region in which the detected lesion or the like is displayed in a list. The detected lesion or the like is displayed by a card 132A in a list in the detection list display region 132. On the card 132A, in addition to the endoscopic image in which the lesion or the like is imaged, the information on the site, the information on the treatment name (information on a specimen collection method in a case of specimen collection), and the like are displayed. The information on the site, the information on the treatment name, and the like can be corrected on the card. In the example illustrated in FIG. 26, by pressing a drop-down button provided in a display column of each piece of information, a drop-down list is displayed, and the information can be corrected. The card 132A is displayed in a detection order from top to bottom in the detection list display region 132.

The merge processing region 133 is a region in which merge processing is performed on the card 132A. The merge processing is performed by dragging the card 132A to be merged to the merge processing region 133.

On the selection screen 130, the user designates the card 132A displayed in the detection list display region 132, and selects the lesion or the like as the report creation target.

Figure 27:
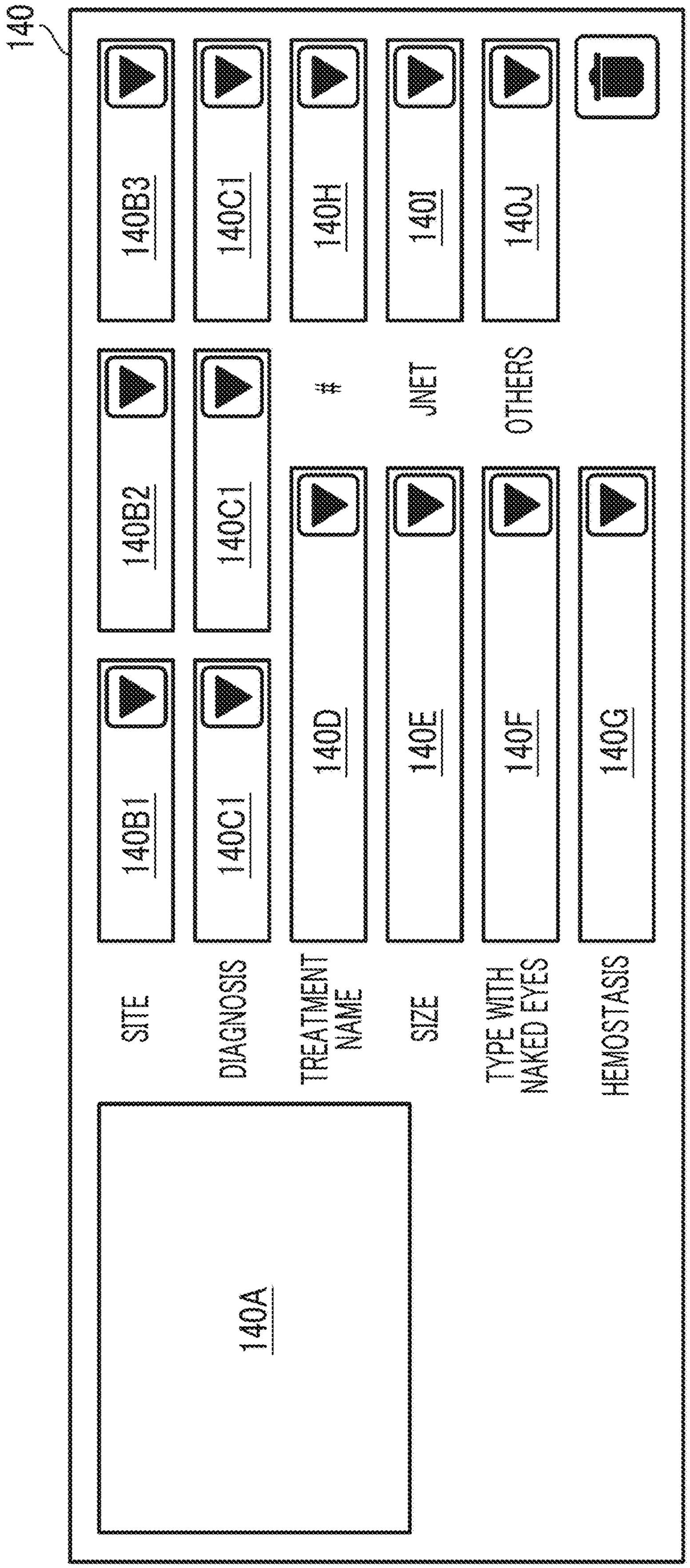
FIG. 27 is a diagram illustrating an example of a detailed input screen.

FIG. 27 is a diagram illustrating an example of a detailed input screen.

A detailed input screen 140 is one of the report creation screens, and is a screen for inputting various kinds of information necessary for generating a report. As illustrated in the figure, the detailed input screen 140 has a plurality of input fields 140A to 140J for inputting various kinds of information necessary for generating a report.

The input field 140A is an input field for an endoscopic image (static image). The endoscopic image (static image) to be attached to the report is input to the input field 140A.

The input fields 140B1 to 140B3 are input fields for information on a site. A plurality of input fields are prepared for the site so that the information thereof can be input hierarchically. In the example illustrated in FIG. 27, three input fields are prepared such that information on the site can be input in three hierarchies. The input is performed by selecting one option from the drop-down list. The drop-down list is displayed by pressing (clicking or touching) the drop-down button provided in each of the input fields 140B1 to 140B3.

Figure 28:
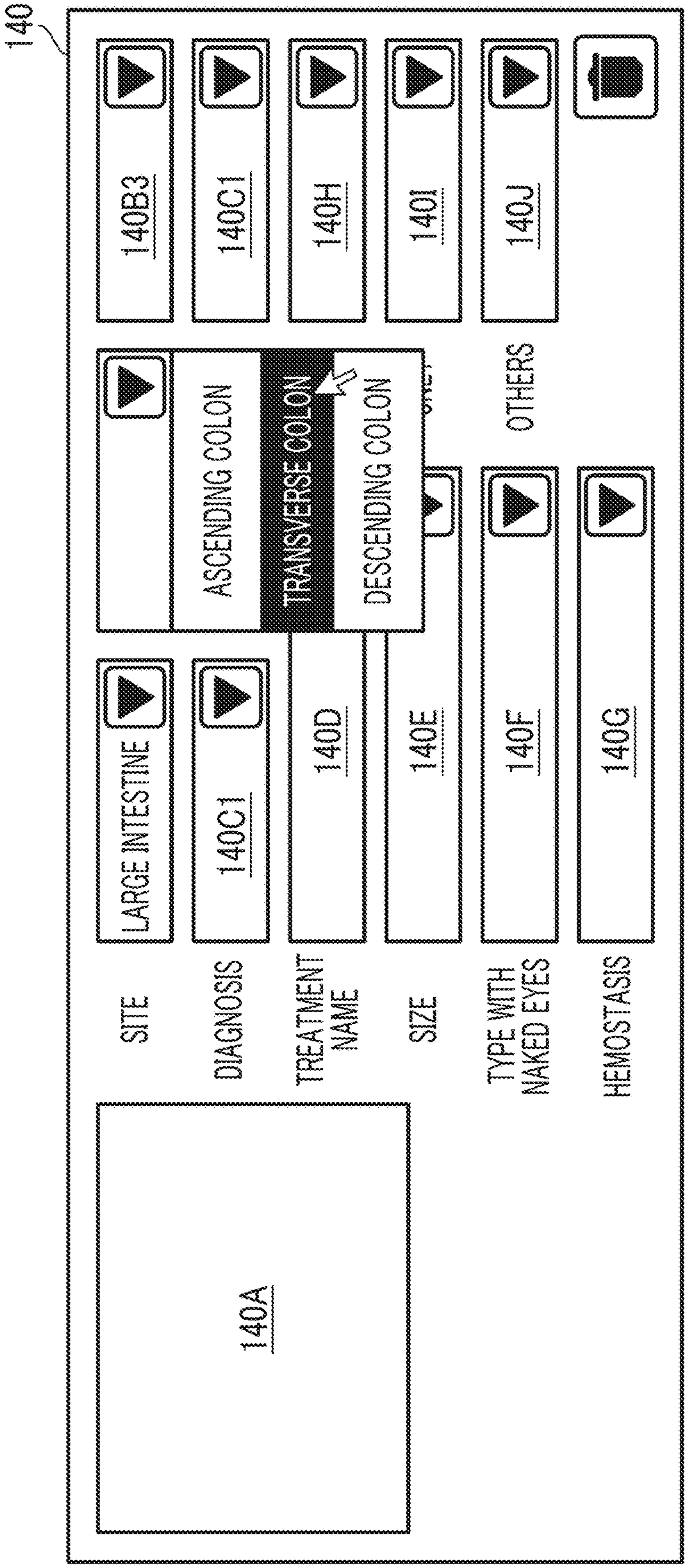
FIG. 28 is a diagram illustrating an example of display of a drop-down list.

FIG. 28 is a diagram illustrating an example of the display of the drop-down list. FIG. 28 illustrates an example of the drop-down list displayed in the input field 140B2 of the second hierarchy for a site.

As illustrated in the figure, in the drop-down list, options are displayed in a list for the designated input field. The user selects one option from the options displayed in a list, and inputs the one option in a target input field. In the example illustrated in the figure, a case where there are three options of "ascending colon", "transverse colon", and "descending colon" is illustrated.

The input fields 140C1 to 140C3 are input fields for information on the diagnosis result. Similarly, a plurality of input fields are prepared for the diagnosis result so that the information thereof can be input hierarchically. In the example illustrated in FIG. 28, three input fields are prepared such that information on the diagnosis result can be input in three hierarchies. The input is performed by selecting one option from the drop-down list. The drop-down list is displayed by pressing the drop-down button provided in each of the input fields 140C1 to 140C3. Selectable diagnosis names are displayed in a list in the drop-down list.

The input field 140D is an input field for information on the treatment name. The input is performed by selecting one option from the drop-down list. The drop-down list is displayed by pressing the drop-down button provided in the input field 140D. Selectable treatment names are displayed in a list in the drop-down list.

The input field 140E is an input field for information on the size of the lesion or the like. The input is performed by selecting one option from the drop-down list. The drop-down list is displayed by pressing the drop-down button provided in the input field 140E. Selectable numerical values are displayed in a list in the drop-down list.

The input field 140F is an input field for information on classification by a naked eye. The input is performed by selecting one option from the drop-down list. The drop-down list is displayed by pressing the drop-down button provided in the input field 140F. Selectable classifications are displayed in a list in the drop-down list.

The input field 140G is an input field for information on hemostatic methods. The input is performed by selecting one option from the drop-down list. The drop-down list is displayed by pressing the drop-down button provided in the input field 140G. Selectable hemostatic methods are displayed in a list in the drop-down list.

The input field 140H is an input field for information on specimen number. The input is performed by selecting one option from the drop-down list. The drop-down list is displayed by pressing the drop-down button provided in the input field 140H. Selectable numerical values are displayed in a list in the drop-down list.

The input field 140I is an input field for information on Japan NBI Expert Team (JNET) classification. The input is performed by selecting one option from the drop-down list. The drop-down list is displayed by pressing the drop-down button provided in the input field 140I. Selectable classifications are displayed in a list in the drop-down list.

The input field 140J is an input field for other information. The input is performed by selecting one option from the drop-down list. The drop-down list is displayed by pressing the drop-down button provided in the input field 140J. Pieces of information that can be input are displayed in a list in the drop-down list.

The automatic input unit 114B automatically inputs the information of the predetermined input fields of the detailed input screen 140 on the basis of the information recorded in the database 120. As described above, in the endoscope system 10 of the present embodiment, the information on the site and the information on the treatment name are input during the examination. The input information is recorded in the database 120. Thus, the information on the site and on the treatment name can be automatically input. The automatic input unit 114B acquires the information on the site and the information on the treatment name for the lesion or the like as the report creation target, from the database 120, and automatically inputs the information to the input fields 140B1 to 140B3 for the site and to the input field 140D for the treatment name of the detailed input screen 140. Further, the endoscopic image (static image) captured for the lesion or the like as the report creation target is acquired from the database 120, and is automatically input to the input field 140A for the image.

Figure 29:
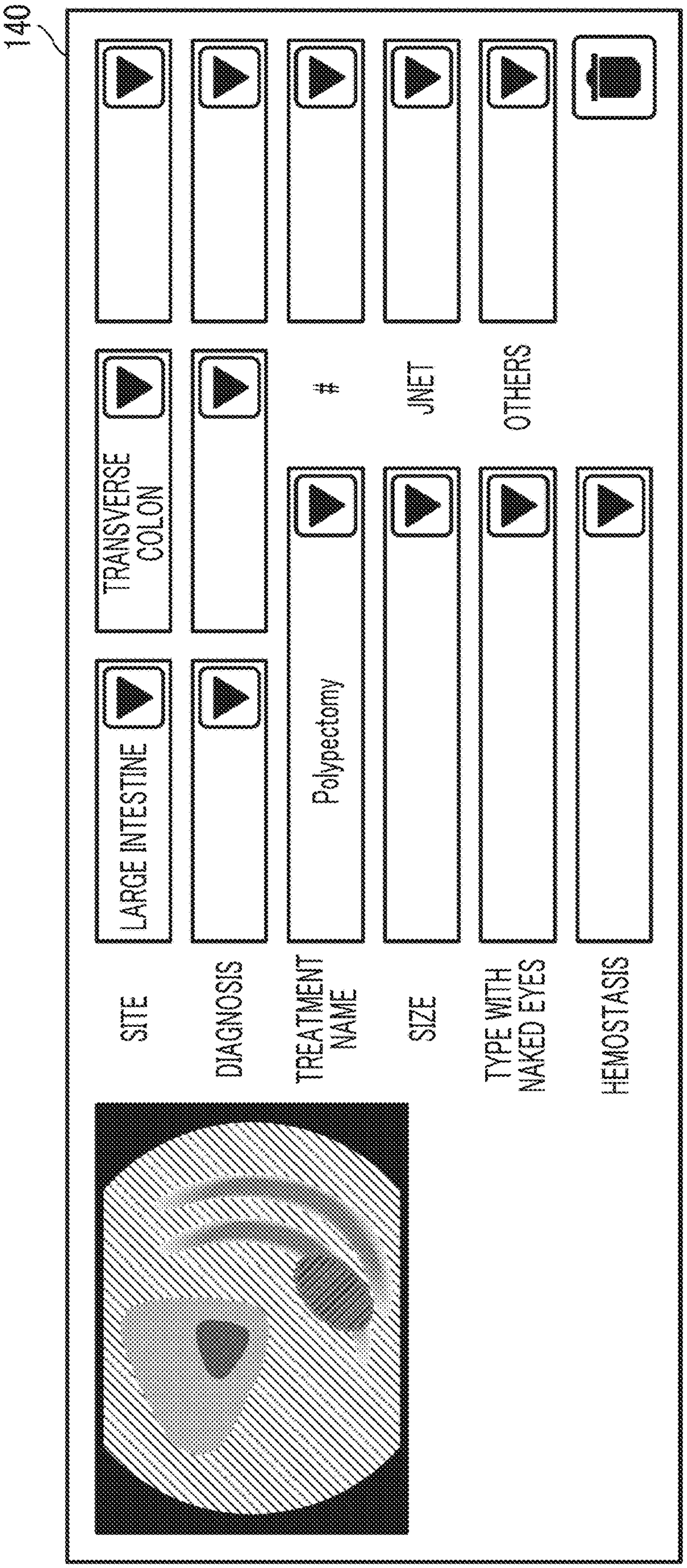
FIG. 29 is a diagram illustrating an example of a detailed input screen which is automatically filled.

FIG. 29 is a diagram illustrating an example of the detailed input screen which is automatically filled.

As illustrated in the figure, the input field for the endoscopic image, the input field for the information on the site, and the input field for the information on the treatment name are automatically filled. As an initial screen of the detailed input screen 140, a screen in which the input field for the endoscopic image, the input field for the information on the site, and the input field for the information on the treatment name are automatically filled is provided to the user terminal 200. The user corrects the input field that is automatically filled, as necessary. For other input fields, in a case where the information to be input can be acquired, it is preferable to automatically input the information.

For example, correcting the input field for the endoscopic image is performed by dragging a target thumbnail image to the input field 140A from a thumbnail list of endoscopic images opened in a separate window.

Correcting the input field for the information on the site and the input field for the information on the treatment name is performed by selecting one option from the drop-down list.

Figure 30:
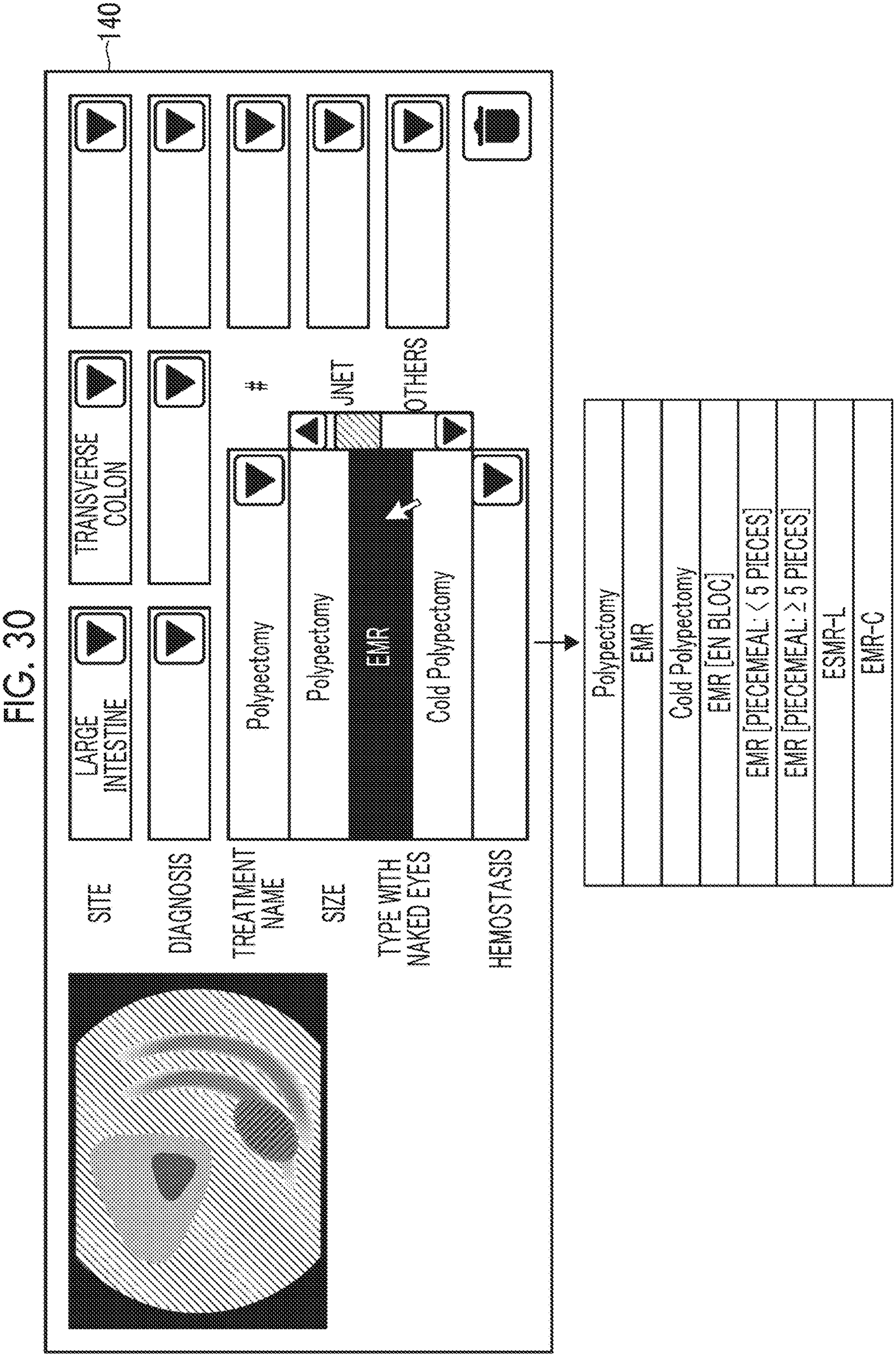
FIG. 30 is a diagram illustrating an example of a detailed input screen during correction.

FIG. 30 is a diagram illustrating an example of the detailed input screen during correction. FIG. 30 illustrates an example of a case where the information of the input field for the treatment name is corrected.

As illustrated in the figure, the correction of the information is performed by selecting one option from the options displayed in the drop-down list.

Here, it is preferable that the number of options displayed in the drop-down list is set to be larger than the number of options displayed during the examination. For example, in a case where the treatment tool is the snare, the options of the treatment name displayed during the examination are three of "Polypectomy", "EMR", and "Cold Polypectomy", as illustrated in FIG. 17B. On the other hand, the treatment names selectable in the detailed input screen 140 are eight of "Polypectomy", "EMR", "Cold Polypectomy", "EMR [en bloc]", "EMR [piecemeal: <5 pieces]", "EMR [piecemeal: ≥5 pieces]", "ESMR-L", and "EMR-C", as illustrated in FIG. 30. In this manner, in a case of creating a report, it is possible to easily correct target information by presenting more options. Meanwhile, during the examination, by narrowing down the options, it is possible for the user to efficiently select the treatment name.

Figure 31:
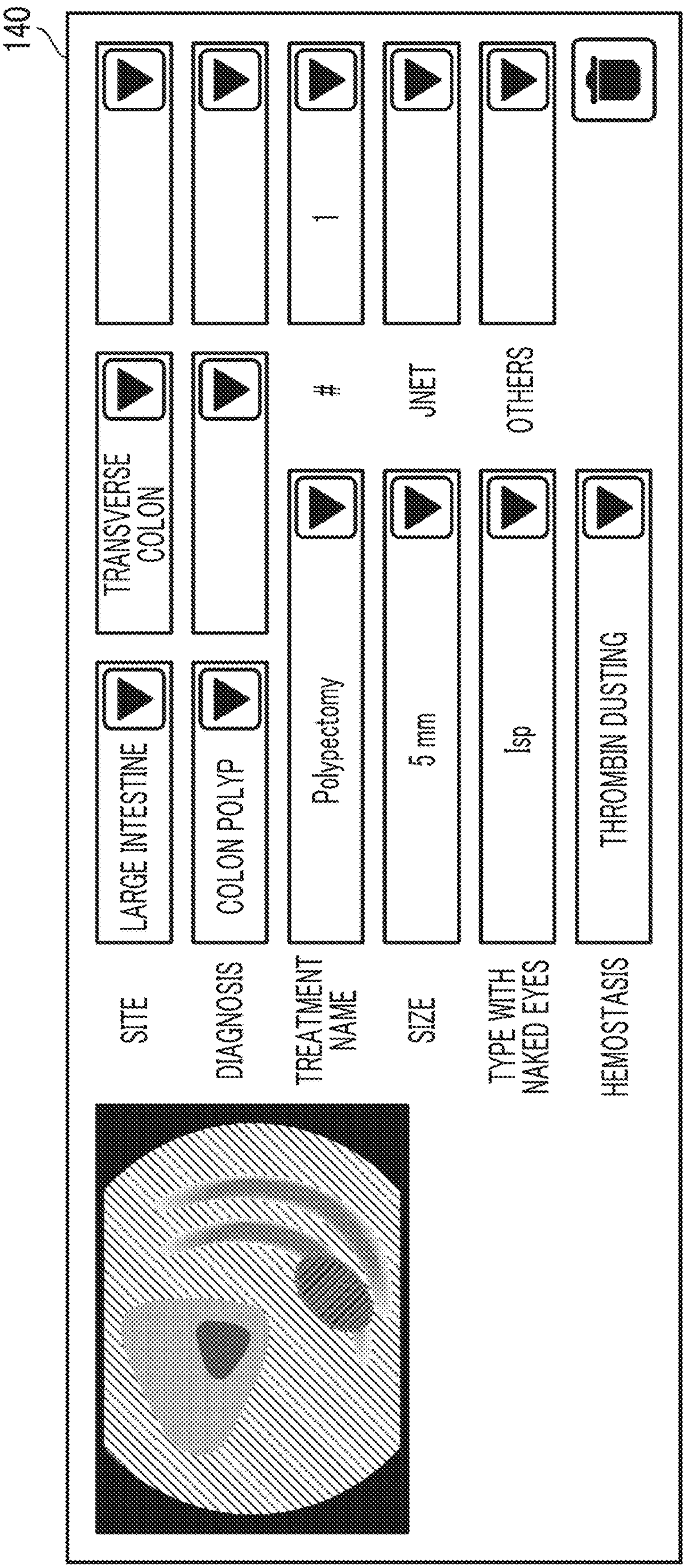
FIG. 31 is a diagram illustrating an example of a detailed input screen after an input is completed.

FIG. 31 is a diagram illustrating an example of the detailed input screen after the input is completed. As illustrated in the figure, the information to be entered in the report is input to each input field.

The report generation unit 114C automatically generates the report in a predetermined format, for the lesion or the like selected as the report creation target, on the basis of the information input on the detailed input screen 140. The generated report is presented on the user terminal 200.

[User Terminal]

The user terminal 200 is used for viewing various kinds of information related to the endoscopy, creating a report, and the like. The user terminal 200 includes, as a hardware configuration, a processor, a main storage unit, an auxiliary storage unit, a display unit, an operation unit, a communication unit, and the like. That is, the user terminal 200 has a so-called computer (for example, personal computer, tablet computer, or the like) configuration as the hardware configuration. For example, the processor is configured by a CPU. For example, the main storage unit is configured by a RAM. For example, the auxiliary storage unit is configured by a hard disk drive, a solid-state drive, a flash memory, or the like. The display unit is configured by a liquid-crystal display, an organic EL display, or the like. The operation unit is configured by a keyboard, a mouse, a touch panel, or the like. For example, the communication unit is configured by a communication interface connectable to a network. The user terminal 200 is communicably connected to the endoscope information management system 100 via the communication unit. More specifically, the user terminal 200 is communicably connected to the endoscope information management device 110.

In the endoscopic image diagnosis support system 1 of the present embodiment, the user terminal 200 constitutes the report creation support device together with the endoscope information management system 100. The display unit of the user terminal 200 is an example of a second display unit.

[Operation of Endoscopic Image Diagnosis Support System]

[Operation of Endoscope System During Examination]

In the following, the operation (information processing method) of the endoscope system 10 during the examination will be described focusing on an input operation of a site and an input operation of a treatment name during the examination.

[Input Operation of Site]

Figure 32:
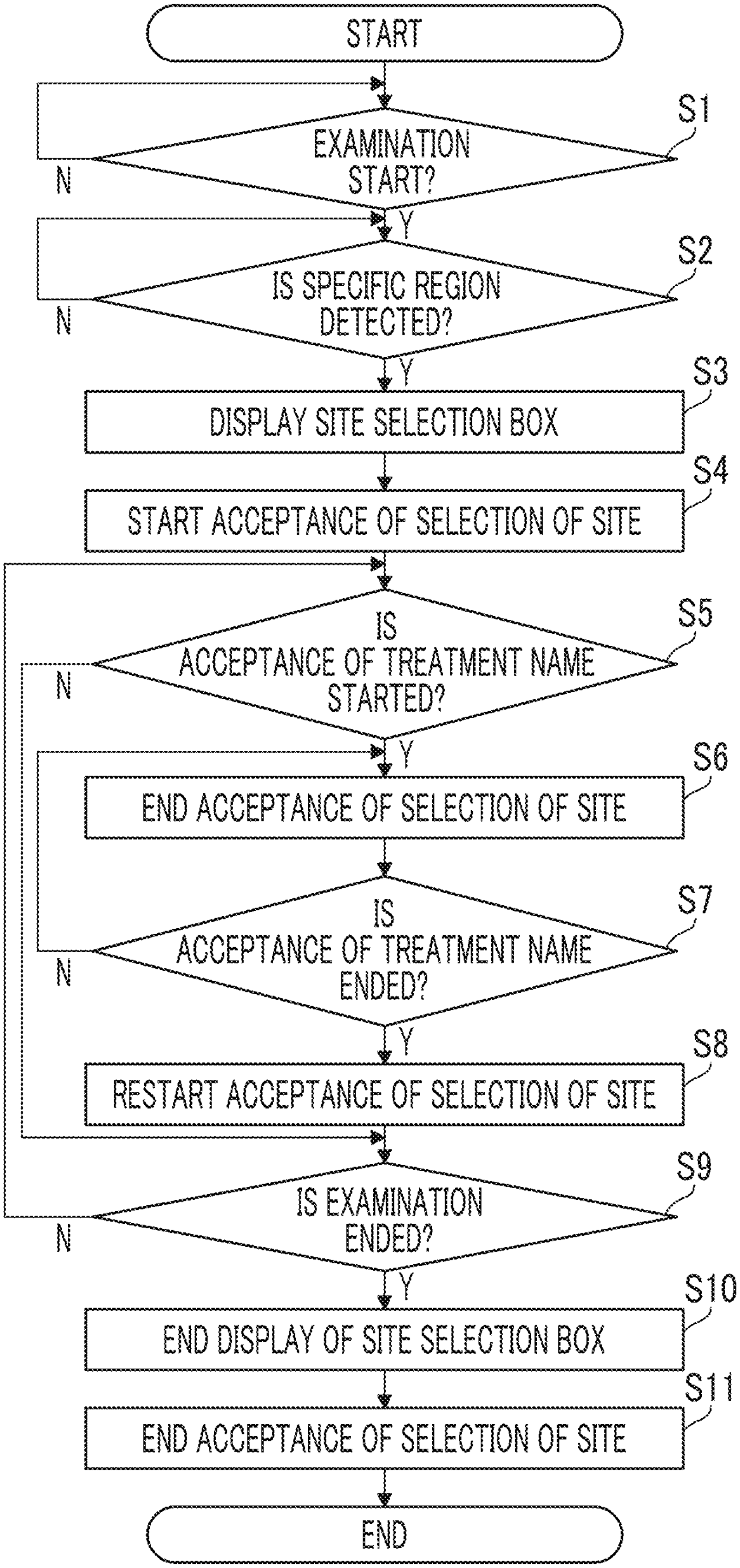
FIG. 32 is a flowchart illustrating a procedure of processing of accepting an input of a site.

FIG. 32 is a flowchart illustrating a procedure of processing of accepting an input of a site.

First, it is determined whether or not the examination has started (Step S1). In a case where the examination has started, it is determined whether or not a specific region is detected from an image (endoscopic image) captured by the endoscope (Step S2). In the present embodiment, it is determined whether or not the ileocecum is detected as the specific region.

In a case where the specific region is detected from the endoscopic image, the site selection box 71 is displayed on the screen 70A of the display device 70 where the endoscopic image is being displayed (refer to FIG. 14) (Step S3). Further, the acceptance of the selection of the site is started (Step S4).

Here, the site selection box 71 is displayed in a state where a specific site is automatically selected in advance. Specifically, the site selection box 71 is displayed in a state where the site to which the specific region belongs is selected. In the present embodiment, the site selection box 71 is displayed in a state where the ascending colon is selected. In this manner, by displaying the site selection box 71 in a state where the site to which the specific region belongs is selected, it is possible to omit the user's initial selection operation. Accordingly, it is possible to efficiently input the information on the site. Further, accordingly, the user can concentrate on the examination.

In a case of starting the display, the site selection box 71 is displayed in an emphasized manner for a fixed time (time T1). In the present embodiment, as illustrated in FIG. 14, the site selection box 71 is displayed by being enlarged. In this manner, by displaying the site selection box 71 in an emphasized manner in a case of starting the display, it is easier for the user to recognize that the acceptance of the selection of the site is started. Further, it is easier for the user to recognize the site being selected.

In a case where a fixed time has elapsed from the start of the display, the site selection box 71 is displayed in a normal display state (refer to FIG. 13). Note that the acceptance of the selection is continued even in the normal display state.

Here, the selection of the site is performed by the foot switch. Specifically, the site being selected is switched in order each time the user operates the foot switch. Then, the display of the site selection box 71 is also switched according to the switching operation. That is, the display of the site being selected is switched.

Further, in a case where the selection operation of the site is performed, the site selection box 71 is displayed in an emphasized manner for a fixed time (time T1).

The information on the selected site is stored in the main storage unit or the auxiliary storage unit. Therefore, in the initial state, the ascending colon is stored as the information on the site being selected.

In a case where the site selection box 71 is displayed on the screen, and the acceptance of the selection of the site is started, it is determined whether or not the acceptance of the treatment name is started (Step S5).

In a case where it is determined that the acceptance of the selection of the treatment name is started, the acceptance of the selection of the site is stopped (Step S6). Note that the display of the site selection box 71 is continued. After that, it is determined whether or not the acceptance of the selection of the treatment name is ended (Step S7). In a case where it is determined that the acceptance of the selection of the treatment name is ended, the acceptance of the selection of the site is restarted (Step S8).

In a case where the acceptance of the selection of the site is restarted, it is determined whether or not the examination has ended (Step S9). Also in a case where it is determined in Step S5 that the acceptance of the treatment name is not started, it is determined whether or not the examination has ended (Step S9). The end of the examination is performed by the user inputting an instruction to end the examination. In addition, for example, the end of the examination can be detected from the image by using the AI or the trained model. For example, the end of the examination can be detected by detecting from the image that the endoscope is pulled out of the body. Further, for example, the end of the examination can be detected by detecting an anus from the image.

In a case where it is determined that the examination has ended, the display of the site selection box 71 is ended (Step S10). That is, the display of the site selection box 71 disappears from the screen. Further, the acceptance of the selection of the site is ended (Step S11). Accordingly, the processing of accepting the input of the site is ended.

On the other hand, in a case where it is determined that the examination has not ended, the processing returns to Step S5, and processing of Step S5 and subsequent steps is executed again.

As described above, in the endoscope system 10 of the present embodiment, in a case where the specific region is detected from the endoscopic image, the site selection box 71 is displayed on the screen 70A, and the selection of the site is possible. The site selection box 71 is displayed on the screen 70A in a state where the site to which the specific region belongs is selected in advance. Accordingly, it is possible to omit the user's initial selection operation.

In principle, in a case where the site selection box 71 is displayed, the acceptance of the selection of the site is continued until the examination ends. However, in a case where the acceptance of the selection of the treatment name is started during the acceptance of the selection of the site, the acceptance of the site is stopped. Accordingly, it is possible to prevent the confliction of the input operations. The stopped acceptance of the selection of the site is restarted in a case where the acceptance of the selection of the treatment name is ended.

[Input Operation of Treatment Name]

Figure 33:
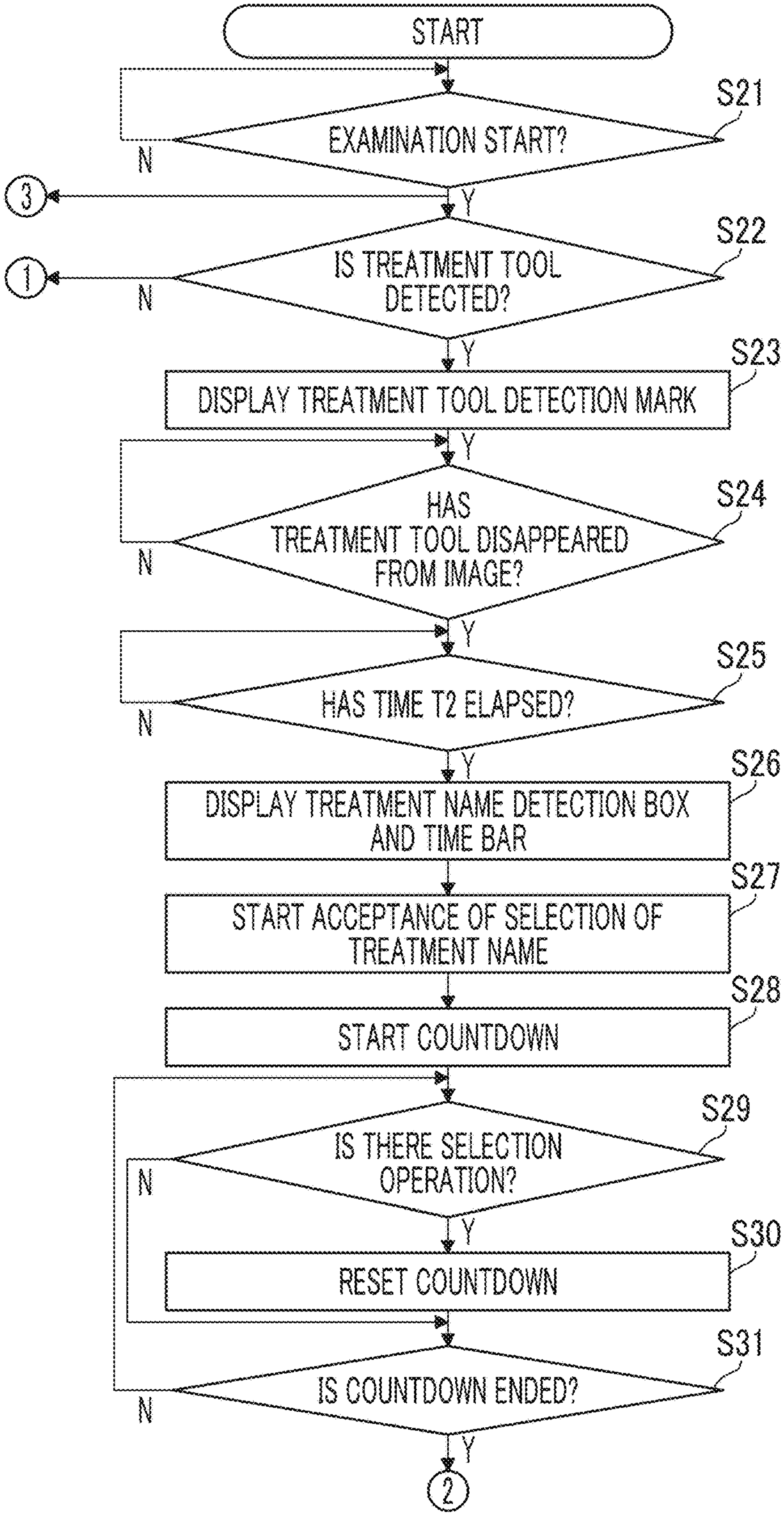
FIG. 33 is a flowchart illustrating a procedure of processing of accepting an input of a treatment name.
Figure 34:
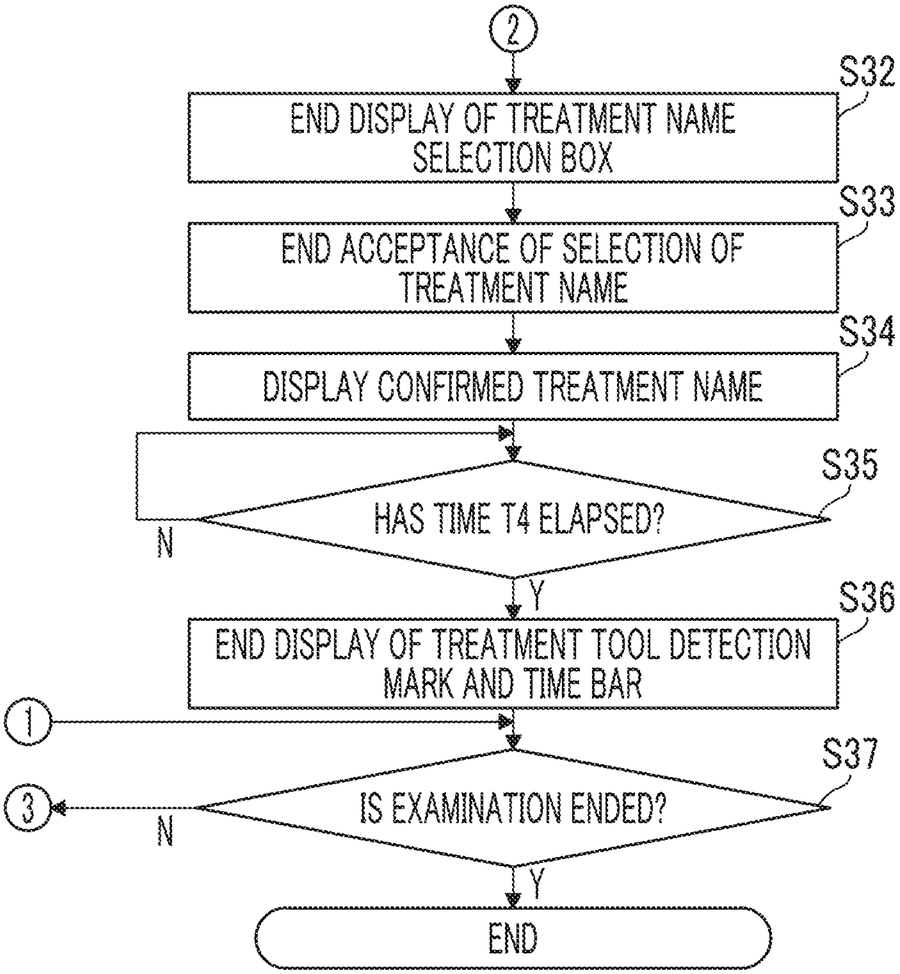
FIG. 34 is a flowchart illustrating a procedure of processing of accepting an input of a treatment name.

FIGS. 33 and 34 are flowcharts illustrating a procedure of processing of accepting an input of the treatment name.

First, it is determined whether or not the examination has started (Step S21). In a case where the examination has started, it is determined whether or not a treatment tool is detected from an image (endoscopic image) captured by the endoscope (Step S22).

In a case where the treatment tool is detected, the treatment tool detection mark 72 is displayed on the screen 70A of the display device 70 where the endoscopic image is being displayed (refer to FIG. 16) (Step S23). Thereafter, it is determined whether or not the treatment tool has disappeared from the endoscopic image (Step S24).

In a case where it is determined that the treatment tool has disappeared from the endoscopic image, it is determined whether or not a fixed time (time T2) has elapsed from the disappearance of the treatment tool (Step S25). In a case where a fixed time has elapsed from the disappearance of the treatment tool, the treatment is considered to have ended, and thus, the treatment name selection box 73 is displayed on the screen 70A of the display device 70. Further, at the same time, the time bar 74 is displayed on the screen 70A of the display device 70 (refer to FIG. 19) (Step S26). In the treatment name selection box 73, the name corresponding to the detected treatment tool is displayed. For example, in a case where the detected treatment tool is the biopsy forceps, the treatment name selection box 73 for biopsy forceps is displayed (refer to FIG. 17A). Further, for example, in a case where the detected treatment tool is the snare, the treatment name selection box 73 for snare is displayed (refer to FIG. 17B). Further, the treatment names as the options to be displayed in the treatment name selection box 73 are displayed in a predetermined arrangement. Moreover, the treatment name selection box 73 is displayed in a state where one treatment name is automatically selected in advance. In this manner, by displaying the treatment name selection box 73 in a state where one treatment name is automatically selected in advance, it is possible to omit the user's initial selection operation in a case where the automatically selected treatment name is correct. Accordingly, it is possible to efficiently input the treatment name. Further, accordingly, the user can concentrate on the examination. The automatically selected treatment name is a treatment name with high execution frequency (treatment name with high selection frequency).

In a case where the treatment name selection box 73 is displayed on the screen 70A, the acceptance of the selection of the treatment name is started (Step S27). Further, the countdown of the display of the treatment name selection box 73 is started (Step S28).

As described above, in a case where the acceptance of the selection of the treatment name is started, the acceptance of the selection of the site is stopped. The acceptance of the selection of the site is stopped until the acceptance of the selection of the treatment name is ended.

In a case where the acceptance of the selection of the treatment name is started, it is determined whether or not there is a selection operation (Step S29). Here, the selection of the treatment name is performed by the foot switch. Specifically, the treatment name being selected is switched in order each time the user operates the foot switch. Then, the display of the treatment name selection box 73 is also switched according to the switching operation. That is, the display of the treatment name being selected is switched.

In a case where the selection operation of the treatment name is performed, the countdown of the display of the treatment name selection box 73 is reset (Step S30). Accordingly, the time for which the selection operation can be performed extends.

After that, it is determined whether or not the countdown has ended (Step S31). Also in a case where it is determined in Step S29 that there is no selection operation, it is determined whether or not the countdown has ended (Step S31).

In a case where the countdown has ended, the selected treatment name is confirmed. In a case where the user does not perform the selection operation of the treatment name during the countdown, the treatment name selected by default is confirmed. In this manner, since the treatment name is confirmed when the countdown has ended, it is possible to eliminate the need for a separate confirmation operation. Accordingly, it is possible to efficiently input information on the treatment name. Further, accordingly, the user can concentrate on the examination.

In a case where it is determined that the countdown has ended, the display of the treatment name selection box 73 is ended (Step S32). That is, the display of the treatment name selection box 73 disappears from the screen. Further, the acceptance of the selection of the treatment name is ended (Step S33).

Meanwhile, when the countdown has ended, the information on the confirmed treatment name is displayed at the display position of the time bar 74 (refer to FIG. 22) (Step S34). The information on the confirmed treatment name is continuously displayed on the screen 70A for a fixed time (time T4). Therefore, in a case where the information on the confirmed treatment name is displayed at the display position of the time bar 74, it is determined whether or not time T4 has elapsed from the start of the display (Step S35). In a case where it is determined that time T4 has elapsed, the display of the treatment tool detection mark 72 and of the time bar 74 is ended (Step S36). That is, the display of the treatment tool detection mark 72 and of the time bar 74 disappears from the screen 70A. The information on the confirmed treatment name also disappears with the disappearance of the display of the time bar 74.

After that, it is determined whether or not the examination has ended (Step S37). The processing of accepting the input of the treatment name is ended by the end of the examination.

On the other hand, in a case where it is determined that the examination has not ended, the processing returns to Step S22, and processing of Step S22 and subsequent steps is executed again.

As described above, in the endoscope system 10 of the present embodiment, in a case where the treatment tool detected from the endoscopic image disappears from the endoscopic image, after a fixed time has elapsed, the display of the treatment name selection box 73 is displayed on the screen 70A, and thus, the selection of the treatment name is possible. The treatment name selection box 73 is displayed on the screen 70A in a state where one treatment name is selected in advance. Accordingly, it is possible to omit the user's initial selection operation.

In principle, the treatment name selection box 73 displayed on the screen 70A disappears from the screen 70A after a fixed time elapses. Then, the selection of the treatment name is confirmed when the treatment name selection box 73 disappears from the screen 70A. Accordingly, a separate operation of confirming the selection is not required, and thus, it is possible to efficiently input information on the treatment name.

[Report Creation Support]

Creating a report is performed using the user terminal 200. In a case where the report creation support is requested from the user terminal 200 to the endoscope information management system 100, processing of supporting the report creation is started.

First, the examination as the report creation target is selected. The examination as the report creation target is selected on the basis of patient information or the like.

In a case where the examination as the report creation target is selected, the lesion or the like as the report creation target is selected. In this case, the selection screen 130 is provided to the user terminal 200 (refer to FIG. 26). On the selection screen 130, the user designates the card 132A displayed in the detection list display region 132, and selects the lesion or the like as the report creation target.

In a case where the lesion or the like as the report creation target is selected, the detailed input screen 140 is provided to the user terminal 200 (refer to FIG. 27). In this case, the detailed input screen 140 is provided to the user terminal 200 in a state where information is automatically input to the predetermined input fields in advance. Specifically, the detailed input screen 140 is provided in a state where information acquired during the examination is input to the input field for the endoscopic image, the input field for the site, and the input field for the treatment name in advance (refer to FIG. 29). These pieces of information are automatically input on the basis of the information recorded in the database 120. The user corrects the automatically input information as necessary. Further, the user inputs information to other input fields.

In a case where predetermined information is input and the generation of the report is requested, the report is generated in a predetermined format on the basis of the input information. The report generation unit 114C automatically generates the report in a predetermined format, for the lesion or the like selected as the report creation target, on the basis of the information input on the detailed input screen 140. The generated report is provided to the user terminal 200.

Modification Examples

[Modification Example of Site Selection Box]

In the embodiment described above, the site is selected by displaying the schema diagram of the hollow organ as the examination target, but the method of selecting the site in the site selection box 71 is not limited thereto. In addition, for example, options written in text may be displayed in a list, and the user may select the option. For example, in the example of the embodiment described above, a configuration can be adopted in which three of "ascending colon", "transverse colon", and "descending colon" are written in text, and are displayed in the site selection box 71 in a list, and the user selects one. Further, for example, a configuration can be adopted in which the text notation and the schema diagram are combined and displayed. Moreover, the site being selected may be separately displayed as text. Accordingly, it is possible to clarify the site being selected.

Further, the method of dividing the sites as the options can be appropriately set according to the type of the hollow organ as the examination target, the purpose of the examination, and the like. For example, in the embodiment described above, the large intestine is divided into three sites, but can be divided into more detailed sites. For example, in addition to "ascending colon", "transverse colon", and "descending colon", "sigmoid colon" and "rectum" can be added as the options. Moreover, each of "ascending colon", "transverse colon", and "descending colon" may be classified in more detail, and a more detailed site can be selected.

[Emphasized Display]

It is preferable that the emphasized display of the site selection box 71 is executed at a timing when it is necessary to input the information on the site. For example, as described above, the information on the site is recorded in association with the treatment name. Therefore, it is preferable to select the site according to the input of the treatment name. As described above, the acceptance of the selection of the site is stopped while the selection of the treatment name is being accepted. Therefore, it is preferable that, before the selection of the treatment name is accepted or after the selection of the treatment name is accepted, the site selection box 71 is displayed in an emphasized manner to prompt the selection of the site. Note that, since a plurality of lesion parts are detected in the same site in some cases, it is more preferable to select the site in advance before the treatment. Therefore, for example, it is preferable that the site selection box 71 is displayed in an emphasized manner at a timing when the treatment tool is detected from the image or at a timing when the lesion part is detected from the image, to prompt the selection of the site. The treatment tool and the lesion part are examples of a detection target different from the specific region.

Further, the site selection box 71 may be displayed in an emphasized manner at the timing of switching the site to prompt the selection of the site. In this case, for example, the site switching is detected from the image by using the AI or the trained model. As in the embodiment described above, in the examination for the large intestine, in a case where the site is selected by divided the large intestine into the ascending colon, the transverse colon, and the descending colon, the site switching can be detected by detecting the hepatic flexure (right colon), the splenic flexure (left colon), and the like from the image. For example, switching from the ascending colon to the transverse colon or switching from the transverse colon to the ascending colon can be detected by detecting the hepatic flexure. Further, switching from the transverse colon to the descending colon or switching from the descending colon to the transverse colon can be detected by detecting the splenic flexure.

As described above, as the method of the emphasized display, in addition to the method of displaying the site selection box 71 in an enlarged manner, methods of changing a color from the normal display form, enclosing with a frame, blinking, and the like can be adopted. Further, a method of appropriately combining the methods can be adopted.

Further, instead of or in addition to the method of prompting the selection of the site via the emphasized display, processing of prompting the selection of the site may be performed using an audio guide or the like. Alternatively, the display of prompting the selection of the site on the screen (for example, message, icon, or the like) may be separately performed.

[Other Uses of Information on Site]

In the embodiment described above, a case where the information on the selected site is recorded in association with the information on the treatment name has been described, but the use of the information on the site is not limited thereto. For example, a configuration can be adopted in which the information on the site being selected is recorded in association with the captured endoscopic image. Accordingly, it can be easily discriminated from which site the acquired endoscopic image is captured. Further, classification or the like of the endoscopic image can be performed for each site by using the associated information on the site.

[Selection Operation of Site]

In the embodiment described above, the selection operation of the site is performed by the foot switch, but the selection operation of the site is not limited thereto. In addition, a configuration can be adopted in which the selection operation is performed by an audio input, a gaze input, a button operation, a touch operation on a touch panel, or the like.

[Modification Example of Treatment Name Selection Box]

The treatment names to be displayed as the selectable treatment names in the treatment name selection box 73 may be arbitrarily set by the user. That is, the user may arbitrarily set or edit the table. In this case, it is preferable that the user can arbitrarily set and edit the number, the order, and the default option of treatment names to be displayed. Accordingly, it is possible to build a user-friendly environment for each user.

Further, a selection history may be recorded, and the table may be automatically corrected on the basis of the recorded selection history. For example, on the basis of the history, the display order may be corrected to the descending order of the selection frequency, or the default option may be corrected. Further, for example, the display order may be corrected to an order of newest selection on the basis of the history. In this case, the display is made in the order of the last selected option (previous selected option) displayed at the top, followed by the second-to-last selected option, the third-to-last selected option, and so on. Similarly, on the basis of the history, the last selected option may be corrected to be the default option.

Further, in the options to be displayed in the treatment name selection box 73, items such as “no treatment” and/or “post-selection” can be included in addition to the treatment name. Accordingly, for example, even in a case where the treatment is not performed, information thereof can be recorded. Further, it is possible to cope with a case where an input of the treatment name is performed after the examination, a case where the performed treatment is not included in the options, or the like.

Further, in the embodiment described above, the treatment name selection box 73 is displayed by associating the treatment tools with the treatment name selection boxes in a one-to-one manner, but the treatment name selection box 73 may be displayed by associating one treatment name selection box with a plurality of treatment tools. That is, in a case where a plurality of treatment tools are detected from the image, the treatment name selection box 73 in which the option of the treatment name corresponding to the combination of the plurality of treatment names is displayed is displayed on the screen 70A.

[Display Timing of Treatment Name Selection Box]

In the embodiment described above, after a fixed time has elapsed from the detection of the disappearance of the treatment tool from the image, the treatment name selection box 73 is displayed on the screen 70A, but the timing when the treatment name selection box 73 is displayed is not limited thereto. For example, a configuration can be adopted in which the treatment name selection box 73 is displayed immediately after the disappearance of the treatment tool from the image is detected.

Further, for example, the end of the treatment is detected from the image by using the AI or the trained model, and the treatment name selection box 73 may be displayed on the screen 70A immediately after the detection or after a fixed time has elapsed from the detection.

By displaying the treatment name selection box 73 after treatment rather than during the treatment, it is possible to concentrate on the treatment during the treatment.

[Display of Treatment Name Selection Box]

There are a plurality of types of treatment tools, but it is preferable that, only in a case where a specific treatment tool is detected, the treatment name selection box 73 corresponding to the detected specific treatment tool is displayed on the screen to accept the selection.

For example, depending on the treatment tool, there may be only one executable treatment. For example, regarding a hemostatic pin as one of the treatment tools, there is no executable treatment other than the hemostasis. Therefore, in this case, since there is no room for selection, the display of the treatment name selection box is not necessary.

Note that, for the treatment tool for which there is only one executable treatment, the treatment name may be automatically input when the treatment tool is detected. In this case, instead of displaying the treatment name selection box 73, the treatment name corresponding to the detected treatment tool may be displayed on the screen 70A, and the display of the treatment name disappears after a fixed time has elapsed, thereby confirming the input. Alternatively, a configuration can be adopted in which the treatment name selection box 73 is displayed in combination with the items of "no treatment" and/or "post-selection" to prompt the user to perform the selection.

[Detailed Input Screen for Report Creation Support]

In the detailed input screen 140 for the report creation support, it is preferable that the automatically filled input fields is distinguishable from other input fields. For example, the automatically filled input fields is distinguishable from other input fields by being displayed in an emphasized manner. Accordingly, it is possible to clarify that the items are automatically filled, and to call attention to the user.

Figure 35:
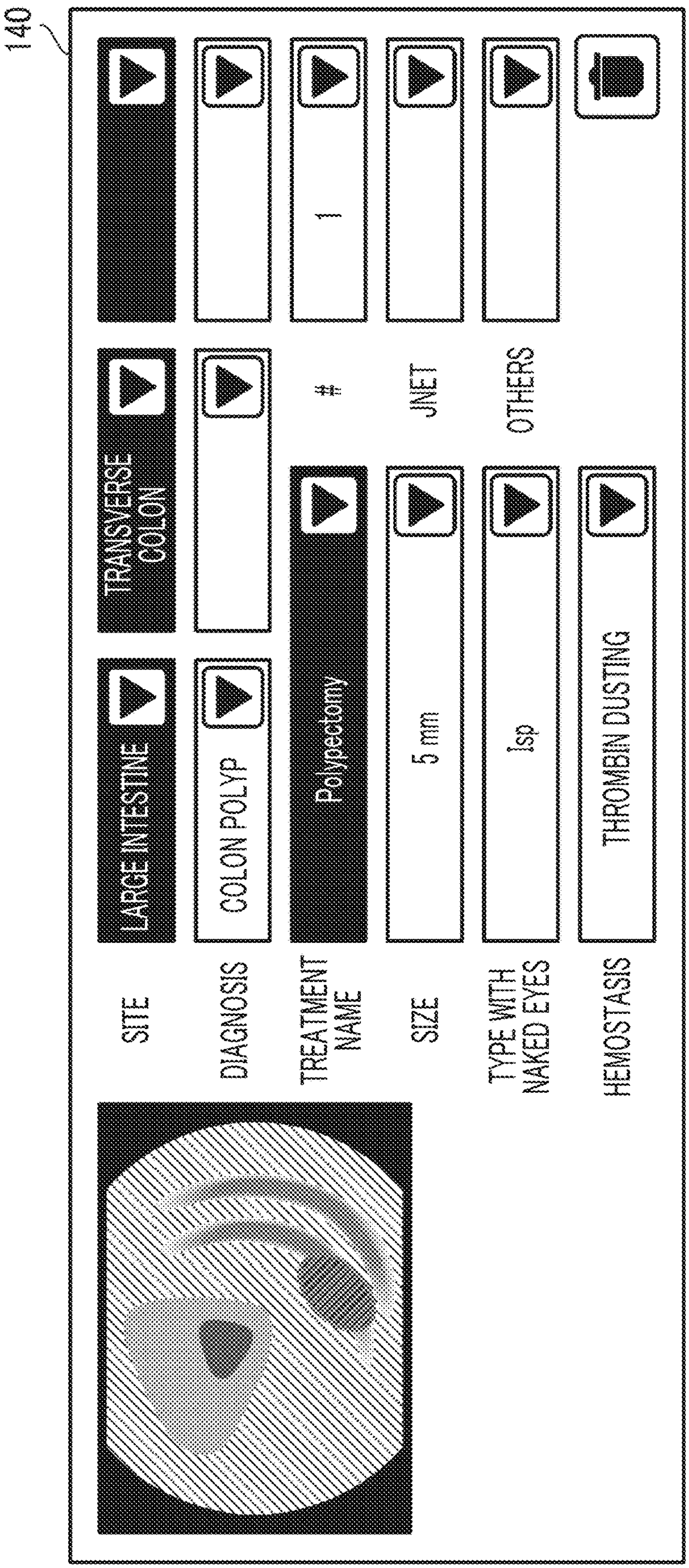
FIG. 35 is a diagram illustrating a modification example of a detailed input screen.

FIG. 35 is a diagram illustrating a modification example of the detailed input screen.

In the example illustrated in the figure, the input field for the site and the input field for the treatment name are displayed in a reversed manner so that the input fields is distinguishable from other input fields. More specifically, a background color and a character color are displayed in a reversed manner so that the input fields is distinguishable from other input fields.

In addition, by making the automatically filled input fields blink, enclosing the automatically filled input fields with a frame, or attaching a caution symbol to the automatically filled input fields, it may be possible to make the automatically filled input fields distinguishable from other input fields.

[Automatic Input]

In the embodiment described above, the information on the site and the information on the treatment name for the lesion or the like as the report creation target are acquired from the database 120, and corresponding input fields are automatically filled, but the method of automatic input is not limited thereto. For example, during the examination, a method can be adopted which records information on the selected site and on the selected treatment name over time (a so-called time log) during the examination, and automatically inputs information on the site, the treatment name, the endoscopic image, and the like by checking with the imaging date and time of the endoscopic image (static image) acquired during the examination. Alternatively, a method can be adopted which records the information on the site and the information on the treatment name in association with the endoscopic image, and automatically inputs the information on the site, the treatment name, the endoscopic image, and the like. In addition, in a case where the endoscopic image is recorded as a video, a method can be adopted which automatically inputs information on the site and on the treatment name from the time information of the video and the information on the time log of the site and the treatment name.

Second Embodiment

As described above, it is preferable that items to be entered in the report can be input without any time and effort during the examination. The endoscopic image diagnosis support system of the present embodiment is configured such that the information regarding a treatment target (lesion part or the like) can be input during the examination. Specifically, the endoscopic image diagnosis support system is configured such that a specific event related to the treatment is detected, a predetermined selection box is displayed on the screen, and information on a detailed site (position) of the treatment target, information on a size of the treatment target, and the like can be input.

Note that the functions are provided as functions of the endoscopic image processing device. Thus, only the functions in the endoscopic image processing device will be described here.

[Endoscopic Image Processing Device]

As described above, the endoscopic image processing device of the present embodiment is configured such that a specific event is detected, a predetermined selection box is displayed on the screen, and information on a detailed site of the treatment target, information on a size of the treatment target (lesion part or the like), and the like can be input. For example, the specific event is an end of the treatment, a detection of the treatment tool, or the like. In the present embodiment, the detailed site selection box is displayed on the screen in accordance with the detection of the treatment tool. Further, the size selection box is displayed on the screen after the detailed site is selected using the detailed site selection box.

[Detailed Site Selection Box]

The display control unit 64 displays a detailed site selection box 90 on the screen in a case where the treatment tool is detected from the endoscopic image by the treatment tool detection unit 63D.

Figure 36:
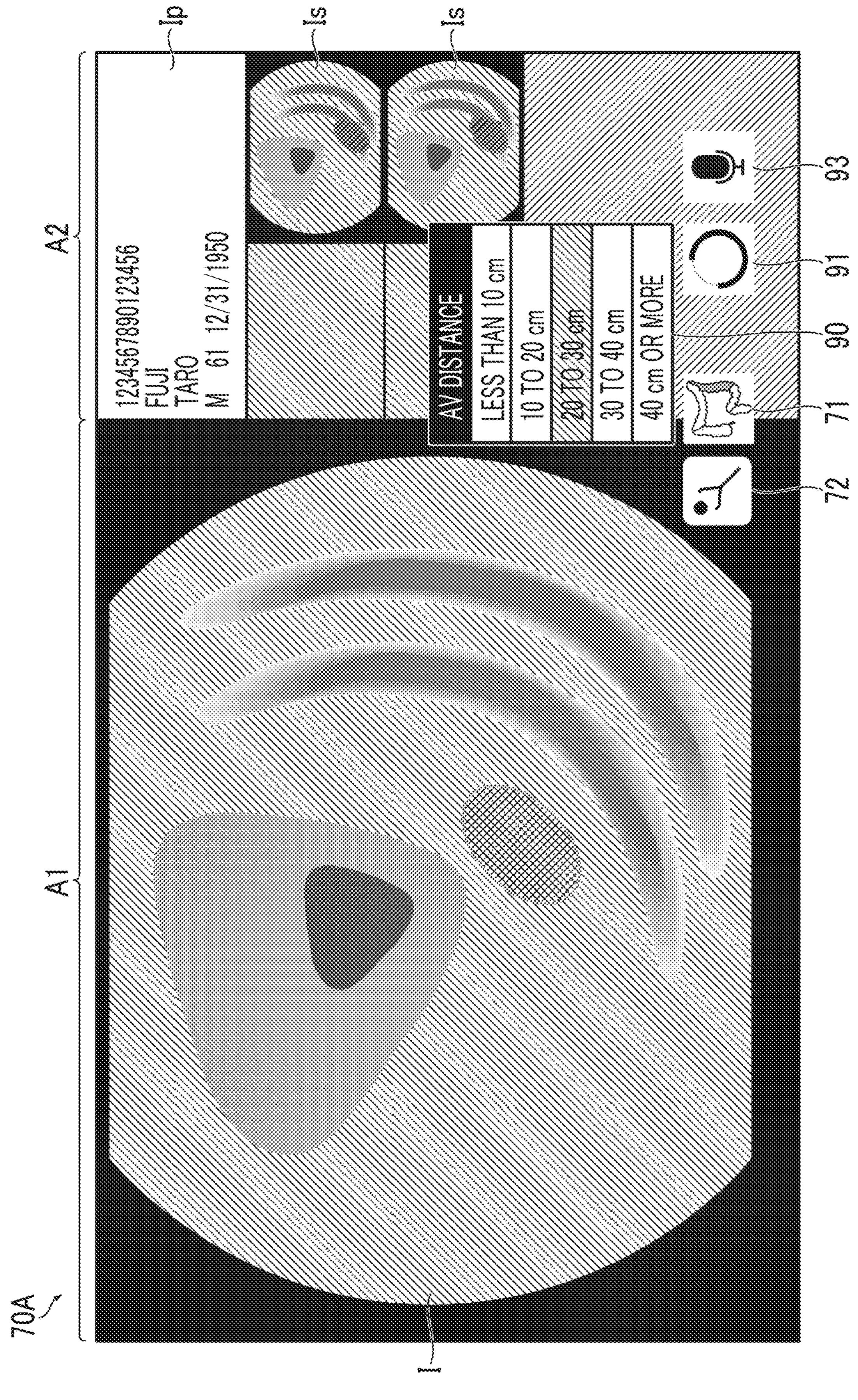
FIG. 36 is a diagram illustrating an example of display of a detailed site selection box.

FIG. 36 is a diagram illustrating an example of display of the detailed site selection box.

The detailed site selection box 90 is a region for selecting a detailed site of the treatment target on the screen. The detailed site selection box 90 constitutes an interface for inputting the detailed site of the treatment target on the screen. In the present embodiment, the detailed site selection box 90 is displayed at a predetermined position on the screen 70A in accordance with the detection of the treatment tool. The display position is preferably in the vicinity of the treatment tool detection mark 72. The display control unit 64 displays the detailed site selection box 90 in a pop-up. The region where the detailed site selection box 90 is displayed on the screen is an example of a fifth region.

For example, the detailed site is specified by a distance from an insertion end. Therefore, for example, in a case where the hollow organ of the examination target is the large intestine, the detailed site is specified by a distance from an anal verge. The distance from the anal verge is referred to as an "AV distance". The AV distance is essentially synonymous with the insertion length.

FIG. 37 is a diagram illustrating an example of the detailed site selection box.

As illustrated in the figure, the detailed site selection box 90 is configured by a so-called list box, and selectable AV distances are displayed in a list. In the example illustrated in FIG. 37, a case in which a list of selectable AV distances is displayed in a vertical line is illustrated. A plurality of options regarding the AV distances of the processing target are examples of a plurality of options regarding the treatment target.

For example, the selectable AV distances are displayed in predetermined distance divisions. In the example illustrated in FIG. 37, a case of selecting one option from five distance divisions is illustrated. Specifically, a case of selecting one option from five distance divisions of "less than 10 cm", "10 to 20 cm (10 cm or more and less than 20 cm)", "20 to 30 cm (20 cm or more and less than 30 cm)", "30 to 40 cm (30 cm or more and less than 40 cm)", and "40 cm or more" is illustrated.

In FIG. 37, an option with a hatched background portion indicates the option being selected. In the example illustrated in FIG. 37, a case where "20 to 30 cm" is selected is illustrated.

In a case where the detailed site selection box 90 is displayed on the screen, the display control unit 64 displays the detailed site selection box 90 on the screen in a state where one option is selected in advance. In the present embodiment, the detailed site selection box is displayed in a state where the option positioned at the top of the list is selected in advance. That is, the option positioned at the top of the list is selected and displayed as the default option. In the example illustrated in FIG. 37, "less than 10 cm" is the default option.

Selection is performed using the input device 50. In the present embodiment, the selection is performed using the foot switch. The selection target is switched in order from the top to the bottom of the list each time the user steps on the foot switch. Moreover, in a case where the foot switch is stepped on after the selection target has reached the bottom of the list, the selection target returns to the top of the list again.

Selection is accepted for a fixed time (T5) from the start of the display of the detailed site selection box 90. In a case where the selection operation (operation of foot switch) is performed within a fixed time from the start of the display, selection is further accepted for a fixed time (T5). That is, the time for which the selection is possible extends. In a case where a state of no operation is continued for a fixed time (T5), the selection is confirmed. That is, the option that is selected at a stage where a fixed time (T5) has elapsed in the state of no operation is confirmed as the option selected by the user. Therefore, for example, in a case where a fixed time (T5) has elapsed in a state of no operation (no selection) after the start of the display of the detailed site selection box 90, the option selected by default is confirmed as the option selected by the user.

As illustrated in FIG. 36, a countdown timer 91 is displayed on the screen 70A such that the remaining time for the selection operation can be known. In FIG. 36, as an example, a case where the countdown timer 91 is displayed as a circle is illustrated. In this case, the color of the circumference is changed over time. The countdown is ended at a stage where the color change has completed one cycle. FIG. 36 illustrates a state where the remaining time is ¼ of time T5. The countdown timer 91 is displayed adjacent to the detailed site selection box 90. The form of the countdown timer 91 is not limited thereto, and may be configured such that, for example, seconds of the remaining time are displayed in numerical values.

The information on the selected (input) detailed site (information on the AV distance) is stored in association with the information on the site being selected, the information on the treatment name to be input (selected) later, and the like. The stored information is used for creating a report. For example, in a case where a report is created by the report creation support unit 114, corresponding input fields are automatically filled.

[Size Selection Box]

In a case where the selection of the detailed site is confirmed, the display control unit 64 displays a size selection box 92 instead of the detailed site selection box 90 on the screen. The region where the size selection box 92 is displayed on the screen is an example of the fifth region. The size selection box 92 is a region for selecting a size of the treatment target (lesion part or the like) on the screen. The size selection box 92 constitutes an interface for inputting the size of the treatment target on the screen.

FIG. 38 is a diagram illustrating an example of the size selection box.

As illustrated in the figure, the size selection box 92 is configured by a so-called list box, and selectable sizes are displayed in a list. In the example illustrated in FIG. 38, a case in which a list of selectable sizes is displayed in a vertical line is illustrated. A plurality of options regarding the size of the processing target are other examples of a plurality of options regarding the treatment target.

For example, the selectable sizes are displayed in predetermined size divisions. In the example illustrated in FIG. 38, a case of selecting one option from five size divisions is illustrated. Specifically, a case of selecting one option from five size divisions of "0 to 5 mm (0 mm or more and less than 5 mm)", "5 to 10 mm (5 mm or more and less than 10 mm)", "10 to 15 mm (10 mm or more and less than 15 mm)", "15 to 20 mm (15 mm or more and less than 20 mm)", and "20 mm or more" is illustrated.

In FIG. 38, an option with a hatched background portion indicates the option being selected. In the example illustrated in FIG. 38, a case where "10 to 15 mm" is selected is illustrated.

In a case where the size selection box 92 is displayed on the screen, the display control unit 64 displays the size selection box 92 on the screen in a state where one option is selected in advance. In the present embodiment, the detailed site selection box is displayed in a state where the option positioned at the top of the list is selected in advance. That is, the option positioned at the top of the list is selected and displayed as the default option. In the example illustrated in FIG. 38, "0 to 5 mm" is the default option.

Selection is performed using the input device 50. In the present embodiment, the selection is performed using the foot switch. The selection target is switched in order from the top to the bottom of the list each time the user steps on the foot switch. Moreover, in a case where the foot switch is stepped on after the selection target has reached the bottom of the list, the selection target returns to the top of the list again.

Selection is accepted for a fixed time (T6) from the start of the display of the size selection box 92. In a case where the selection operation (operation of foot switch) is performed within a fixed time from the start of the display, selection is further accepted for a fixed time (T6). In a case where a state of no operation is continued for a fixed time (T6), the selection is confirmed.

Similar to the selection of the detailed site, the countdown timer 91 is displayed on the screen 70A such that the remaining time for the selection operation can be known (refer to FIG. 36).

The information on the selected (input) detailed site (information on the AV distance) is stored in association with the information on the site being selected, the information of the detailed site previously input (selected), the information on the treatment name to be input (selected) later, and the like. The stored information is used for creating a report. For example, in a case where a report is created by the report creation support unit 114, corresponding input fields are automatically filled.

In this manner, with the endoscopic image processing device of the present embodiment, the detailed site selection box 90 and the size selection box 92 are displayed on the screen in accordance with a specific event (detection of treatment tool), and the information on the detailed site and the information on the size can be input for the treatment target. Accordingly, it is possible to save time and effort for creating a report.

Modification Example

[Display Condition]

In the embodiment described above, the detailed site selection box 90 is displayed on the screen with the detection of the treatment tool as a trigger, but the condition of a trigger for the display is not limited thereto. The detailed site selection box 90 may be displayed on the screen with the detection of the end of the treatment as a trigger. Further, the detailed site selection box 90 may be displayed on the screen after a fixed time has elapsed from the detection of the treatment tool or after a fixed time has elapsed from the detection of the end of the treatment.

Further, in the embodiment described above, the size selection box 92 is displayed after the detailed site selection box 90 is displayed, but the order of displaying selection boxes is not particularly limited.

Further, a configuration can be adopted in which the detailed site selection box 90, the size selection box 92, and the treatment name selection box 73 are consecutively displayed in a predetermined order. For example, a configuration can be adopted in which in a case where the treatment end is detected, or in a case where the treatment tool is detected, selection boxes are displayed in order of the detailed site selection box 90, the size selection box 92, and the treatment name selection box 73.

Further, a configuration can be adopted in which each selection box is displayed on the screen with a display instruction via an audio input as a trigger. In this case, a configuration can be adopted in which each selection box is displayed on the screen after waiting for the display instruction via an audio input after the treatment tool is detected. For example, a configuration can be adopted in which in a state where the treatment tool is detected in the image (during recognition of treatment tool), in a case where audio is input, a corresponding selection box is displayed. For example, a configuration can be adopted in which in a case where "AV" is input by audio in a state where the treatment tool is being detected, the detailed site selection box 90 is displayed on the screen, and in a case where "size" is input by audio, the size selection box 92 is displayed on the screen.

In the configuration in which audio can be input, for example, it is preferable that a predetermined icon is displayed on the screen to indicate to the user that audio can be input. Reference numeral 93 illustrated in FIG. 36 is an example of an icon. In a case where this icon (audio input icon) 93 is displayed on the screen, audio can be input. Therefore, for example, in the example described above, in a case where the treatment tool is detected, the audio input icon 93 is displayed on the screen.

Note that the audio input technique including audio recognition is a well-known technique, so detailed description thereof will be omitted.

[Default Option]

In the embodiment described above, the option position at the top of the list is used as the default option, but a configuration can be adopted in which the default option is dynamically changed on the basis of various kinds of information. For example, for the detailed site, the default option can be changed according to the site being selected. Further, for example, a configuration can be adopted in which in a case where an insertion length is separately measured, information on the measured insertion length is acquired, and the default option is set on the basis of the acquired information on the insertion length. In this case, a measurement unit for the insertion length is separately provided. Further, for the size, for example, a configuration can be adopted in which a size is measured by image measurement, information on the measured size is acquired, and the default option is set on the basis of the acquired information on the size. In this case, a function of an image measurement unit is separately provided.

[Selection Method]

In the embodiment described above, the option is selected using the foot switch, but the method of selecting the option is not limited thereto. For example, a configuration can be adopted in which the option is selected by an audio input device instead of the foot switch, or in combination with the foot switch.

In a case of the selection via the audio input, for example, the selection can be confirmed at the same time as the selection. That is, a configuration can be adopted in which the selection is confirmed without any waiting time. In this case, selection of an option via an audio input is confirmed at the same time as completion of the audio input.

Note that a configuration can be adopted in which in a case where selection via an audio input is adopted, the display of the selection box is performed by the audio input. In this case, a configuration can be adopted in which selection of the option is performed at the same time as a display instruction for each selection box. For example, a configuration can be adopted in which in a case where "AV 30 cm" is input by audio in a state where the treatment tool is being detected, the detailed site selection box 90 is displayed on the screen, and "30 to 40 cm" is selected as the option. Accordingly, the user can check the input information on the screen. In a case of correction, audio for the option to be corrected is input while the detailed site selection box 90 is displayed. Further, in a case of combination with the foot switch, the option can be switched by the foot switch.

Third Embodiment

In the second embodiment described above, a configuration is adopted in which an event regarding the treatment is detected, a predetermined selection box is displayed on the screen, and predetermined information regarding the treatment target can be input. It is preferable that, regardless of the presence or absence of the treatment, items to be entered in the report can be input without any time and effort during the examination. The endoscopic image diagnosis support system of the present embodiment is configured such that the information regarding a region of interest such as a lesion part can be appropriately input during the examination.

Note that the functions are provided as functions of the endoscopic image processing device. Thus, only the functions in the endoscopic image processing device will be described here.

[Endoscopic Image Processing Device]

The endoscopic image processing device of the present embodiment is configured such that, during the examination, a predetermined selection box is displayed on the screen with the detection of a specific event as a trigger, and information regarding a region of interest such as a lesion part can be selectively input. Specifically, the detailed site selection box or the size selection box is displayed on the screen according to the acquisition of a key image. Here, the key image is an image that can be used for diagnosis after examination, or an image that can be used (attached) for a report to be created after examination. That is, the key image is an image (candidate image) as a candidate for the image to be used in diagnosis, a report, or the like. Therefore, the endoscope information management device 110 acquires a static image regarded as a key image, as a static image to be used in a report. Therefore, the static image acquired as the key image is automatically input to the input field 140A (in a case of one key image). The static image acquired as the key image is recorded with predetermined identification information (information indicating that the static image is a key image) added thereto in order to distinguish the static image from other static images.

[Display of Detailed Site Selection Box and Size Selection Box]

As described above, in the endoscopic image processing device of the present embodiment, the detailed site selection box or the size selection box is displayed on the screen according to the acquisition of a key image.

In the present embodiment, in a case where "key image" is input by audio immediately after the static image is captured, the static image obtained by imaging is designated as the key image, and the key image is acquired.

In a case where the key image is acquired, the display control unit 64 displays the detailed site selection box 90 on the screen (refer to FIG. 36). The detailed site selection box 90 is displayed on the screen in a state where one option is selected in advance. The user performs a selection operation via the foot switch or the audio input. In a case where a state of no operation (no selection) is continued for a fixed time (T5), the selection is confirmed. Note that, in the present embodiment, a plurality of options for the AV distance displayed in the detailed site selection box 90 are examples of a plurality of options regarding a region of interest.

In a case where the selection of the detailed site is confirmed, the display control unit 64 displays a size selection box 92 instead of the detailed site selection box 90 on the screen. The size selection box 92 is displayed on the screen in a state where one option is selected in advance. The user performs a selection operation via the foot switch or the audio input. In a case where a state of no operation (no selection) is continued for a fixed time (T6), the selection is confirmed. Note that, in the present embodiment, a plurality of options for the size displayed in the size selection box 92 are examples of a plurality of options regarding a region of interest.

In this manner, with the endoscopic image processing device of the present embodiment, the detailed site selection box 90 and the size selection box 92 are displayed on the screen in accordance with the acquisition of the key image, and regardless of the presence or absence of the treatment, the information on the detailed site and the information on the size can be input for the region of interest such as a lesion part. Accordingly, it is possible to save time and effort for creating a report.

The information input (selected) using each selection box is stored in association with the information on the site being selected and the information on the key image. The stored information is used for creating a report. For example, in a case where a report is created by the report creation support unit 114, corresponding input fields are automatically filled.

Note that the modification example illustrated in the second embodiment is also applied to the present embodiment.

Modification Example

[Method of Acquiring Key Image]

In the embodiment described above, the key image is acquired in a case where "key image" is input by audio immediately after the static image is captured, but the method of acquiring the key image is not limited thereto.

For example, a configuration can be adopted in which a key image is acquired in a case where a static image is captured by performing a predetermined operation. For example, a configuration can be adopted in which a key image is acquired in a case where a static image is captured by pressing a specific button provided on the operation part 22 of the endoscope 20. Alternatively, a configuration can be adopted in which a key image is acquired in a case where a static image is captured by inputting a predetermined keyword using audio. For example, a configuration can be adopted in which a key image is acquired in a case where a static image is captured by inputting "key image" using audio before imaging.

Further, for example, a configuration can be adopted in which a key image is acquired by performing a predetermined operation after a static image is captured. For example, a configuration can be adopted in which a static image obtained by imaging is acquired as a key image by pressing a specific button provided on the operation part 22 of the endoscope 20 immediately after the static image is captured. Alternatively, a configuration can be adopted in which a static image obtained by imaging is acquired as a key image by an operation of stepping on the foot switch for a fixed time (pressing for a long time) immediately after the static image is captured. Alternatively, a configuration can be adopted in which a key image is acquired in a case where a predetermined keyword is input by audio after a static image is captured. For example, a configuration can be adopted in which in a case where "key image" is input by audio immediately after a static image is captured, the static image obtained by imaging is acquired as the key image.

Further, a configuration may be adopted in which, after a static image is captured, whether or not to adopt the captured image as a key image can be selected. For example, a configuration can be adopted in which in a case where a predetermined operation is performed after a static image is captured, a menu for selecting the use of the image is displayed on the screen, and a key image can be selected as one of options in the menu. As the predetermined operation, for example, an operation of stepping on the foot switch for a fixed time or longer is exemplified. In this case, in a case where the foot switch is stepped on for a fixed time or longer immediately after a static image is captured, a menu for the use of the image is displayed, and an option is displayed by the foot switch or the audio input. For example, a configuration can be adopted in which the menu is displayed each time the static image is captured. In this case, acceptance of selection is performed for a fixed time, and in a case where the selection operation is not performed, the display of the menu disappears.

The acquired key image is recorded in association with the information on the site being selected. Further, the key image acquired at the time of the treatment (key image acquired during the treatment, within a certain period before the treatment, or within a certain period after the treatment) is recorded in association with the input treatment name. In this case, the key image is also recorded in association with the information on the site being selected.

Further, a configuration can be adopted in which the key image is automatically acquired with a predetermined event as a trigger. For example, a configuration can be adopted in which a key image is automatically acquired in accordance with an input of a site and/or an input of a treatment name. Specifically, the key image is acquired as follows.

(1) Case of Acquiring Key Image According to Input of Site

In this case, the most recently captured static image is acquired as a key image according to an input of a site. That is, the most recent static image in terms of time is selected as a key image from among the static images captured before a time point when the site is input.

As another form, the oldest static image in terms of time can be selected as a key image from among the static images captured after a time point when the site is input. That is, the first captured static image after the site is input is selected as a key image.

As still another form, a configuration can be adopted in which an image (one frame of video) captured at a time point when an input of a site is performed is automatically acquired as a key image. In this case, a configuration can be adopted in which a plurality of frames before and after the time point when the input of the site is performed is acquired as a plurality of key images. Further, a configuration can be adopted in which an image with the best image quality from among the images is automatically extracted, and is automatically acquired as a key image. The image with a good image quality is an image with no blurriness and blurs and with proper exposure. Therefore, for example, an image with exposure in a proper range and with high sharpness (image with no blurriness and blurs) is automatically extracted as an image with good image quality.

The key image acquired according to the input of the site is recorded in association with the information on the site being selected.

(2) Case of Acquiring Key Image According to Input of Treatment Name

Also in this case, the most recently captured static image is acquired as a key image according to an input of a treatment name. That is, the most recent static image in terms of time is selected as a key image from among the static images captured before a time point when the treatment name is input.

As another form, the oldest static image in terms of time can be selected as a key image from among the static images captured after a time point when the treatment name is input. That is, the first captured static image after the treatment name is input is selected as a key image.

As still another form, a configuration can be adopted in which an image captured at a time point when an input of a treatment name is performed is automatically acquired as a key image. In this case, a configuration can be adopted in which a plurality of frames before and after the time point when the input of the treatment name is performed are acquired as a plurality of key images. Further, a configuration can be adopted in which an image with the best image quality from among the images is automatically extracted, and is automatically acquired as a key image.

The key image acquired according to the input of the treatment name is recorded in association with the information on the treatment name. In this case, the key image is also recorded in association with the information on the site being selected.

[Use of Key Image]

As described above, the report creation support unit 114 of the endoscope information management device 110 automatically inputs the key image to the input field 140A. Therefore, the key image is displayed on the report creation screen together with the site and treatment name input during the examination (for example, refer to FIG. 27).

Further, as described above, a plurality of key images may be acquired. That is, a plurality of key images may be acquired as candidates for use in the report. In this case, for example, the report creation support unit 114 displays a plurality of acquired key images in a list on the screen, and accepts selection of the key image to be used in the report. Then, the selected key image is automatically input to the input field 140A.

Further, a video may be attached to the report. In this case, for example, a static image (one frame) constituting one scene of the video can be used as a key image. As the scene (one frame) to be used as the key image, for example, the first scene (first frame) of the video can be used.

Further, in a case where a video is attached to the report, for example, a configuration can be adopted in which in a case where "key image" is input by audio immediately after the video is captured, a key image is automatically acquired from the video. In addition, for example, as described in the modification example, a configuration can be adopted in which in a case where a predetermined operation is performed before the start of the imaging or after the end of the imaging, a key image is automatically acquired from the video.

Other Embodiments

[Application to Other Medical Images]

In the embodiment described above, the image captured using a flexible endoscope (electronic endoscope) is used as the processing target image, but the application of the present invention is not limited thereto, and the present invention can be applied to a case where a medical image captured by other modalities such as an ultrasound diagnostic apparatus, X-ray equipment, digital mammography, a computed tomography (CT) device, and a magnetic resonance imaging (MM) device are used as the processing target. Further, the present invention can be applied to a case where an image captured by a rigid endoscope is used as a processing target.

[Hardware Configuration]

Further, the functions of the processor device 40 and of the endoscopic image processing device 60 in the endoscope system 10 are realized by various processors. Similarly, the functions of the endoscope information management device 110 in the endoscope information management system 100 can be realized by various processors.

The various processors include a CPU and/or a graphics processing unit (GPU) as a general-purpose processor executing a program and functioning as various processing units, a programmable logic device (PLD) as a processor of which the circuit configuration can be changed after manufacture, such as a field-programmable gate array (FPGA), and a dedicated electrical circuit as a processor having a circuit configuration designed exclusively for executing specific processing such as an application-specific integrated circuit (ASIC). The program is synonymous with software.

One processing unit may be configured by one processor among these various processors, or may be configured by two or more same or different kinds of processors. For example, one processing unit may be configured by a plurality of FPGAs, or by a combination of a CPU and an FPGA. Further, a plurality of processing units may be configured by one processor. As an example where a plurality of processing units are configured by one processor, first, there is a form where one processor is configured by a combination of one or more CPUs and software as typified by a computer used in a client, a server, or the like, and this processor functions as a plurality of processing units. Second, there is a form where a processor fulfilling the functions of the entire system including a plurality of processing units via one integrated circuit (IC) chip as typified by a system-on-chip (SoC) or the like is used. In this manner, various processing units are configured by using one or more of the above-described various processors as hardware structures.

Further, in the embodiment described above, the processor device 40 and the endoscopic image processing device 60 constituting the endoscope system 10 are separately configured, but the processor device 40 may have the function of the endoscopic image processing device 60. That is, the processor device 40 and the endoscopic image processing device 60 can be integrated. Similarly, the light source device 30 and the processor device 40 can be integrated.

[Examination Target]

In the embodiment described above, a case where the large intestine is examined is exemplified, but the application of the present invention is not limited thereto. The present invention can be similarly applied to a case where other hollow organs are examined. For example, the present invention can be similarly applied to a case where a stomach, a small intestine, or the like is examined.

[Treatment Tool]

In the embodiment described above, biopsy forceps and snares are exemplified as the treatment tool, but the treatment tool that can be used in the endoscope is not limited thereto.

Treatment tools can be used as appropriate depending on the hollow organ as the examination target, the content of the treatment, and the like.

[Additional Remarks]

The following additional remarks are further disclosed with respect to the embodiments described above.

(Additional Remark 1)

An information processing apparatus including:

a first processor, in which the first processor is configured to acquire an image captured using an endoscope, display the acquired image in a first region on a screen of a first display unit, detect a treatment tool from the acquired image, choose a plurality of treatment names corresponding to the detected treatment tool, display the plurality of chosen treatment names in a second region on the screen of the first display unit, and accept selection of one treatment name from among the plurality of displayed treatment names.

(Additional Remark 2)

The information processing apparatus described in Additional Remark 1, in which the first processor displays the plurality of treatment names in the second region in a state where one treatment name is selected in advance.

(Additional Remark 3)

The information processing apparatus described in Additional Remark 2, in which the first processor chooses the plurality of treatment names by referring to a table in which the plurality of treatment names are associated for each treatment tool.

(Additional Remark 4)

The information processing apparatus described in Additional Remark 3, in which, in the table, information on the treatment name to be selected by default is further associated for each treatment tool, and the first processor displays the plurality of treatment names in the second region in a state where one treatment name is selected in advance by referring to the table.

(Additional Remark 5)

The information processing apparatus described in Additional Remark 3 or 4, in which, in the table, information on a display order of the plurality of treatment names is further associated for each treatment tool, and the first processor displays the plurality of treatment names in the display order corresponding to the detected treatment tool in the second region by referring to the table.

(Additional Remark 6)

The information processing apparatus described in Additional Remark 5, in which the first processor is configured to record a history of selection of the treatment name, and correct the information on the display order of the treatment names registered in the table in a descending order of selection frequency on the basis of the history of the selection of the treatment name.

(Additional Remark 7)

The information processing apparatus described in Additional Remark 5, in which the first processor corrects the information on the display order of the treatment names registered in the table in an order of newest selection.

(Additional Remark 8)

The information processing apparatus described in any one of Additional Remarks 3 to 7, in which, in a case where the number of the treatment names of treatments executable by the treatment tool exceeds a specified number, the treatment names corresponding to the specified number or less are registered in the table.

(Additional Remark 9)

The information processing apparatus described in Additional Remark 8, in which the specified number is set to a number smaller than the number of the treatment names selectable in an input field for the treatment name in a report creation support device that supports creation of a report in which at least the treatment name is to be entered.

(Additional Remark 10)

The information processing apparatus described in any one of Additional Remarks 1 to 9, in which the first processor is configured to detect a plurality of types of treatment tools, choose, in a case where a specific treatment tool among the plurality of types of the treatment tools is detected, a plurality of treatment names corresponding to the detected specific treatment tool, display the plurality of chosen treatment names in the second region, and accept selection of one treatment name from among the plurality of displayed treatment names.

(Additional Remark 11)

The information processing apparatus described in any one of Additional Remarks 1 to 10, in which the first processor displays items of no treatment and/or post-selection as selectable items in addition to the plurality of chosen treatment names, in the second region.

(Additional Remark 12)

The information processing apparatus described in any one of Additional Remarks 1 to 11, in which the first processor displays the plurality of treatment names in the second region after a first time has elapsed from disappearance of the treatment tool from the image.

(Additional Remark 13)

The information processing apparatus described in any one of Additional Remarks 1 to 12, in which the first processor is configured to accept selection until a second time elapses from start of display of the plurality of treatment names in the second region, and confirm the selection after the second time has elapsed.

(Additional Remark 14)

The information processing apparatus described in Additional Remark 13, in which, in a case where the selection is accepted until the second time elapses, the first processor extends a period for acceptance until the second time elapses from the acceptance of the selection.

(Additional Remark 15)

The information processing apparatus described in Additional Remark 13 or 14, in which, in a case where the acceptance of the selection is started, the first processor displays display indicating a remaining time until end of the acceptance, in a third region on the screen of the first display unit.

(Additional Remark 16)

The information processing apparatus described in Additional Remark 15, in which the first processor displays information on the treatment name of which the selection is confirmed, in the third region.

(Additional Remark 17)

The information processing apparatus described in any one of Additional Remarks 1 to 16, in which, in a case where the treatment tool is detected from the image, the first processor displays a figure or a symbol indicating detection of the treatment tool, in a fourth region on the screen of the first display unit.

(Additional Remark 18)

The information processing apparatus described in Additional Remark 17, in which the first processor displays the figure or the symbol corresponding to the detected treatment tool in the fourth region.

(Additional Remark 19)

The information processing apparatus described in any one of Additional Remarks 1 to 18, in which the second region is set in a vicinity of a position where the treatment tool appears within the image displayed in the first region.

(Additional Remark 20)

The information processing apparatus described in any one of Additional Remarks 1 to 19, in which the first processor is configured to acquire information on a site, and record information on the selected treatment name in association with the acquired information on the site.

(Additional Remark 21)

The information processing apparatus described in any one of Additional Remarks 1 to 20, in which the first processor displays a list box in which the plurality of treatment names are displayed in a list, in the second region.

(Additional Remark 22)

The information processing apparatus described in any one of Additional Remarks 1 to 21, in which the first processor records a static image captured during a treatment, in association with information on the selected treatment name.

(Additional Remark 23)

The information processing apparatus described in Additional Remark 22, in which the first processor records, as a candidate for an image to be used in a report or a diagnosis, the static image captured during the treatment, in association with the information on the selected treatment name.

(Additional Remark 24)

The information processing apparatus described in Additional Remark 23, in which the first processor acquires, as the candidate for the image to be used in the report or the diagnosis, a most recent static image in terms of time among static images captured before a time point when selection of the treatment name is accepted, or an oldest static image in terms of time among static images captured after the time point when the selection of the treatment name is accepted.

(Additional Remark 25)

The information processing apparatus described in any one of Additional Remarks 1 to 24, in which the first processor is configured to display the plurality of treatment names in the second region, display a plurality of options regarding a treatment target in a fifth region on the screen of the first display unit before selection of the treatment name is accepted or after the selection of the treatment name is accepted, and accept one selection from among the plurality of options displayed in the fifth region.

(Additional Remark 26)

The information processing apparatus described in Additional Remark 25, in which the plurality of options regarding the treatment target are a plurality of options for a detailed site or a size of the treatment target.

(Additional Remark 27)

A report creation support device that supports creation of a report, including:

a second processor, in which the second processor is configured to display a report creation screen with at least an input field for a treatment name, on a second display unit, acquire information on the treatment name selected in the information processing apparatus described in any one of Additional Remarks 1 to 25, automatically input the acquired information on the treatment name to the input field for the treatment name, and accept correction of the automatically input information of the input field for the treatment name.

(Additional Remark 28)

The report creation support device described in Additional Remark 27, in which, in a case where an instruction to correct the information on the treatment name is given, the second processor is configured to display the plurality of treatment names on the second display unit, and accept the correction of the information on the treatment name via selection.

(Additional Remark 29)

The report creation support device described in Additional Remark 28, in which the number of the selectable treatment names is greater than the number of the treatment names selectable in the information processing apparatus.

(Additional Remark 30)

The report creation support device described in any one of Additional Remarks 27 to 29, in which the second processor displays the input field for the treatment name such that the input field for the treatment name is distinguishable from other input fields on the report creation screen.

(Additional Remark 31)

A report creation support device that supports creation of a report, including:

a second processor, in which the second processor is configured to display a report creation screen with at least input fields for a treatment name and a static image, on a second display unit, acquire information on the treatment name and the static image selected in the information processing apparatus described in any one of Additional Remarks 22 to 24, automatically input the acquired information on the treatment name to the input field for the treatment name, automatically input the acquired static image to the input field for the static image, and accept correction of the automatically input information of the input field for the treatment name and the automatically input static image of the input field for the static image.

(Additional Remark 32)

An endoscope system including:

an endoscope;

the information processing apparatus described in any one of Additional Remarks 1 to 26; and an input device.

(Additional Remark 33)

An information processing method including:

a step of acquiring an image captured using an endoscope;

a step of displaying the acquired image in a first region on a screen of a first display unit;

a step of detecting a treatment tool from the acquired image;

a step of choosing a plurality of treatment names corresponding to the detected treatment tool;

a step of displaying the plurality of chosen treatment names in a second region on the screen of the first display unit; and a step of accepting selection of one treatment name from among the plurality of displayed treatment names.

(Additional Remark 34)

An information processing apparatus including:

a first processor, in which the first processor is configured to acquire an image captured using an endoscope, display the acquired image in a first region on a screen of a first display unit, display a plurality of sites of a hollow organ as an observation target in a second region on the screen of the first display unit, accept selection of one site from among the plurality of sites, detect a treatment tool from the acquired image, choose a plurality of treatment names corresponding to the detected treatment tool, display the plurality of chosen treatment names in a third region on the screen of the first display unit, and accept selection of one treatment name from among the plurality of treatment names from start of the display until a third time elapses.

(Additional Remark 35)

The information processing apparatus described in Additional Remark 34, in which the first processor records a captured static image in association with information on the selected treatment name and/or information on the selected site.

(Additional Remark 36)

The information processing apparatus described in Additional Remark 35, in which the first processor records, as a candidate for an image to be used in a report or a diagnosis, the static image captured during treatment in association with information on the selected treatment name and/or information on the selected site.

(Additional Remark 37)

The information processing apparatus described in Additional Remark 36, in which the first processor acquires, as the candidate for the image to be used in the report or the diagnosis, a most recent static image in terms of time among static images captured before a time point when selection of the treatment name is accepted, or an oldest static image in terms of time among static images captured after the time point when the selection of the treatment name is accepted.

(Additional Remark 38)

A report creation support device that supports creation of a report, including:

a second processor, in which the second processor is configured to display a report creation screen with at least input fields for a treatment name, a site, and a static image, on a second display unit, acquire information on the treatment name, information on the site, and the static image selected in the information processing apparatus described in any one of Additional Remarks 34 to 37, automatically input the acquired information on the treatment name to the input field for the treatment name, automatically input the acquired information on the site to the input field for the site, automatically input the acquired static image to the input field for the static image, and accept correction of the automatically input information of the input fields for the treatment name and the site, and the automatically input static image of the input field for the static image.

EXPLANATION OF REFERENCES

1: endoscopic image diagnosis support system
10: endoscope system
20: endoscope
21: insertion part of endoscope
21A: distal end portion of insertion part
21B: bendable portion of insertion part
21C: soft portion of insertion part
21*a*: observation window of distal end portion
21*b*: illumination window of distal end portion
21*c*: air/water supply nozzle of distal end portion
21*d*: forceps outlet of distal end portion
22: operation part of endoscope
22A: angle knob of operation part
22B: air/water supply button of operation part
22C: suction button of operation part
22D: forceps insertion port of operation part

23: connection part of endoscope
23A: cord of connection part
23B: light guide connector of connection part
23C: video connector of connection part
30: light source device
40: processor device
41: endoscope control unit of processor device
42: light source control unit of processor device
43: image processing unit of processor device
44: input control unit of processor device
45: output control unit of processor device
50: input device
60: endoscopic image processing device
61: endoscopic image acquisition unit of endoscopic image processing device
62: input information acquisition unit of endoscopic image processing device
63: image recognition processing unit of endoscopic image processing device
63A: lesion part detection unit of image recognition processing unit
63B: discrimination unit of image recognition processing unit
63C: specific region detection unit of image recognition processing unit
63D: treatment tool detection unit of image recognition processing unit
64: display control unit of endoscopic image processing device
65: examination information output control unit of endoscopic image processing device
70: display device
70A: screen of display device
71: site selection box displayed on screen of display device
72: treatment tool detection mark displayed on screen of display device
73: treatment name selection box displayed on screen of display device
74: time bar displayed on screen of display device
80: treatment tool
90: detailed site selection box
91: countdown timer
92: size selection box
93: audio input icon
100: endoscope information management system
110: endoscope information management device
111: examination information acquisition unit of endoscope information management device
112: examination information recording control unit of endoscope information management device
113: information output control unit of endoscope information management device
114: report creation support unit of endoscope information management device
114A: report creation screen generation unit of report creation support unit
114B: automatic input unit of report creation support unit
114C: report generation unit of report creation support unit
120: database
130: selection screen
131: captured image display region of selection screen
132: detection list display region of selection screen
132A: card displayed in detection list display region
133: merge processing region of selection screen
140: detailed input screen
140A: input field for endoscopic image (static image)
140B1: input field for information on site
140B2: input field for information on site
140B3: input field for information on site
140C1: input field for information on diagnosis result
140C2: input field for information on diagnosis result
140C3: input field for information on diagnosis result
140D: input field for information on treatment name
140E: input field for information on size of lesion
140F: input field for information on classification by naked eye
140G: input field for information on hemostatic method
140H: input field for information on specimen number
140I: input field for information on JNET classification
140J: input field for other information
200: user terminal
A1: main display region of screen during examination
A2: secondary display region of screen during examination
A3: discrimination result display region of screen during examination
Ar: forceps direction
F: frame surrounding lesion region in endoscopic image
I: endoscopic image
Ip: information regarding patient
Is: static image
P: lesion part
Sc: schema diagram
S1 to S11: procedure of processing of accepting input of site
S21 to S37: procedure of processing of accepting input of treatment name

What is claimed is:

1. An information processing apparatus comprising:
a first processor,
wherein the first processor is configured to
acquire an image captured using an endoscope,
display the acquired image in a first region on a screen of a first display unit,
detect a treatment tool from the acquired image,
choose a plurality of treatment names corresponding to the detected treatment tool,
display the plurality of chosen treatment names in a second region on the screen of the first display unit, and
accept selection of one treatment name from among the plurality of displayed treatment names,
wherein the first processor displays the plurality of treatment names in the second region after a first time has elapsed from disappearance of the treatment tool from the image.

2. The information processing apparatus according to claim 1,
wherein the first processor displays the plurality of treatment names in the second region in a state where one treatment name is selected in advance.

3. The information processing apparatus according to claim 2,
wherein the first processor chooses the plurality of treatment names by referring to a table in which the plurality of treatment names are associated for each treatment tool.

4. The information processing apparatus according to claim 3,
wherein, in the table, information on the treatment name to be selected by default is further associated for each treatment tool, and the first processor displays the plurality of treatment names in the second region in a state where one treatment name is selected in advance by referring to the table.

5. The information processing apparatus according to claim 3, wherein, in the table, information on a display order of the plurality of treatment names is further associated for each treatment tool, and the first processor displays the plurality of treatment names in the display order corresponding to the detected treatment tool in the second region by referring to the table.

6. The information processing apparatus according to claim 5, wherein the first processor is configured to record a history of selection of the treatment name, and correct the information on the display order of the treatment names registered in the table in a descending order of selection frequency on the basis of the history of the selection of the treatment name.

7. The information processing apparatus according to claim 5, wherein the first processor corrects the information on the display order of the treatment names registered in the table in an order of newest selection.

8. The information processing apparatus according to claim 3, wherein, in a case where the number of the treatment names of treatments executable by the treatment tool exceeds a specified number, the treatment names corresponding to the specified number or less are registered in the table.

9. The information processing apparatus according to claim 8, wherein the specified number is set to a number smaller than the number of the treatment names selectable in an input field for the treatment name in a report creation support device that supports creation of a report in which at least the treatment name is to be entered.

10. The information processing apparatus according to claim 1, wherein the first processor is configured to detect a plurality of types of treatment tools, choose, in a case where a specific treatment tool among the plurality of types of the treatment tools is detected, a plurality of treatment names corresponding to the detected specific treatment tool, display the plurality of chosen treatment names in the second region, and accept selection of one treatment name from among the plurality of displayed treatment names.

11. The information processing apparatus according to claim 1, wherein the first processor displays items of no treatment and/or post-selection as selectable items in addition to the plurality of chosen treatment names, in the second region.

12. The information processing apparatus according to claim 1, wherein, in a case where the treatment tool is detected from the image, the first processor displays a figure or a symbol indicating detection of the treatment tool, in a fourth region on the screen of the first display unit.

13. The information processing apparatus according to claim 12, wherein the first processor displays the figure or the symbol corresponding to the detected treatment tool in the fourth region.

14. The information processing apparatus according to claim 1, wherein the second region is set in a position that does not overlap where the treatment tool appears and is adjacent to where the treatment tool appears within the image displayed in the first region.

15. The information processing apparatus according to claim 1, wherein the first processor is configured to acquire information on a site, and record information on the selected treatment name in association with the acquired information on the site.

16. The information processing apparatus according to claim 1, wherein the first processor displays a list box in which the plurality of treatment names are displayed in a list, in the second region.

17. The information processing apparatus according to claim 1, wherein the first processor records a static image captured during a treatment, in association with information on the selected treatment name.

18. The information processing apparatus according to claim 17, wherein the first processor records, as a candidate for an image to be used in a report or a diagnosis, the static image captured during the treatment, in association with the information on the selected treatment name.

19. The information processing apparatus according to claim 18, wherein the first processor acquires, as the candidate for the image to be used in the report or the diagnosis, a most recent static image in terms of time among static images captured before a time point when selection of the treatment name is accepted, or an oldest static image in terms of time among static images captured after the time point when the selection of the treatment name is accepted.

20. The information processing apparatus according to claim 1, wherein the first processor is configured to display the plurality of treatment names in the second region, display a plurality of options regarding a treatment target in a fifth region on the screen of the first display unit before selection of the treatment name is accepted or after the selection of the treatment name is accepted, and accept one selection from among the plurality of options displayed in the fifth region.

21. The information processing apparatus according to claim 20, wherein the plurality of options regarding the treatment target are a plurality of options for a detailed site or a size of the treatment target.

22. A report creation support device that supports creation of a report, comprising:

a second processor, wherein the second processor is configured to display a report creation screen with at least an input field for a treatment name, on a second display unit, acquire information on the treatment name selected in the information processing apparatus according to claim 1, automatically input the acquired information on the treatment name to the input field for the treatment name, and accept correction of the automatically input information of the input field for the treatment name.

23. The report creation support device according to claim 22, wherein, in a case where an instruction to correct the information on the treatment name is given, the second processor is configured to display the plurality of treatment names on the second display unit, and accept the correction of the information on the treatment name via selection.

24. The report creation support device according to claim 23, wherein the number of the selectable treatment names is greater than the number of the treatment names selectable in the information processing apparatus.

25. The report creation support device according to claim 22, wherein the second processor displays the input field for the treatment name such that the input field for the treatment name is distinguishable from other input fields on the report creation screen.

26. A report creation support device that supports creation of a report, comprising:

a second processor, wherein the second processor is configured to display a report creation screen with at least input fields for a treatment name and a static image, on a second display unit, acquire information on the treatment name and the static image selected in the information processing apparatus according to claim 17, automatically input the acquired information on the treatment name to the input field for the treatment name, automatically input the acquired static image to the input field for the static image, and accept correction of the automatically input information of the input field for the treatment name and the automatically input static image of the input field for the static image.

27. An endoscope system comprising:

an endoscope;

the information processing apparatus according to claim 1; and an input device.

28. An information processing apparatus comprising:

a first processor, wherein the first processor is configured to acquire an image captured using an endoscope, display the acquired image in a first region on a screen of a first display unit, detect a treatment tool from the acquired image, choose a plurality of treatment names corresponding to the detected treatment tool, display the plurality of chosen treatment names in a second region on the screen of the first display unit, and accept selection of one treatment name from among the plurality of displayed treatment names, wherein the first processor is configured to accept selection until a second time elapses from start of display of the plurality of treatment names in the second region, and confirm the selection after the second time has elapsed.

29. The information processing apparatus according to claim 28, wherein, in a case where the selection is accepted until the second time elapses, the first processor extends a period for acceptance until the second time elapses from the acceptance of the selection.

30. The information processing apparatus according to claim 28, wherein, in a case where the acceptance of the selection is started, the first processor displays display indicating a remaining time until end of the acceptance, in a third region on the screen of the first display unit.

31. The information processing apparatus according to claim 30, wherein the first processor displays information on the treatment name of which the selection is confirmed, in the third region.

32. An information processing method comprising:

a step of acquiring an image captured using an endoscope;

a step of displaying the acquired image in a first region on a screen of a first display unit;

a step of detecting a treatment tool from the acquired image;

a step of choosing a plurality of treatment names corresponding to the detected treatment tool;

a step of displaying the plurality of chosen treatment names in a second region on the screen of the first display unit; and a step of accepting selection of one treatment name from among the plurality of displayed treatment names, wherein the plurality of treatment names is displayed in the second region after a first time has elapsed from disappearance of the treatment tool from the image.

* * * * *